US005814477A

United States Patent [19]
Williams et al.

[11] Patent Number: 5,814,477
[45] Date of Patent: Sep. 29, 1998

[54] RECOMBINANT CLOSTRIDIAL TOXIN PROTEIN

[75] Inventors: James A. Williams; John A. Kink; Christopher M. Clemens, all of Madison; Sean B. Carroll, Cottage Grove, all of Wis.

[73] Assignee: Ophidian Pharmaceuticals, Inc., Madison, Wis.

[21] Appl. No.: 457,048

[22] Filed: Jun. 1, 1995

Related U.S. Application Data

[60] Division of Ser. No. 161,907, Dec. 2, 1993, Pat. No. 5,601,823, which is a continuation-in-part of Ser. No. 985,321, Dec. 4, 1992, which is a continuation-in-part of Ser. No. 429,791, Oct. 31, 1989, Pat. No. 5,196,193.

[51] Int. Cl.$^6$ ............ C12N 15/31; C12N 15/00; C12N 15/09
[52] U.S. Cl. ........ 435/69.1; 435/70.1; 435/71.1; 435/71.2; 435/69.7; 435/252.33; 435/320.1; 536/23.7
[58] Field of Search .............. 435/69.1, 252.33; 536/23.7

[56] References Cited

U.S. PATENT DOCUMENTS 5,196,193  3/1993  Carroll .
5,268,295  12/1993  Serrero .

OTHER PUBLICATIONS

Lyerly et al., Current Microbiol., 21:29, 1990.
von Eichel–Streiber et al., J. Gen. Microbiol., 135:55, 1989.
Price et al., Current Microbiol., 16:55, 1987.
P.H.A. Sneath et al., "Clostridium," *Bergey's Manual® of Systematic Bacteriology*, vol. 2, pp. 1141–1200, Williams & Wilkins (1986).
P.G. Engelkirk et al., "Classification", *Principles and Practice of Clinical Anaerobic Bacteriology*, pp. 22–23, Star Publishing Co., Belmont, CA (1992).
J. Stephen and R.A. Petrowski, "Toxins Which Traverse Membranes and Deregulate Cells," *Bacterial Toxins*, 2d ed., pp. 66–67, American Society for Microbiology (1986).
R. Berkow and A.J. Fletcher (eds.), "Bacterial Dieases," *Merck Manual of Diagnosis and Therapy*, 16th ed., pp. 119–126, Merck Research Laboratories, Rahway, N.J. (1992).
O.H. Siegmund and C.M. Fraser (eds.), "Clostridial Infections," *Merck Veterinary Manual*, 5th ed., pp. 396–409, Merck & Co., Rahway, N.J. (1979).
C.L. Hatheway, "Toxigenic Clostridia," Clin. Microbiol. Rev. 3:66–98 (1990).
S. Arnon, "Infant Botulism: Anticipating the Second Decade," J. Infect. Dis. 154:201–206 (1986).
S. Arnon, "Infant Botulism," Ann. Rev. Med. 31:541 (1980).
K.L. MacDonald et al., "The Changing Epidemiology of Adult Botulism in the United States," Am. J. Epidemiol. 124:794 (1986).
C.O. Tacket et al., "Equine Antitoxin Use and Other Factors That Predict Outcome in Type A Foodborne Botulism,", Am. J. Med. 76:794 (1984).
M.N. Swartz, "Anaerobic Spore–Forming Bacilli: The Clostridia," pp. 633–646, in B.D. Davis et al., (eds.), *Microbiology*, 4th edition, J.B. Lippincott Co. (1990).
S. Arnon et al., "Infant Botulism: Epidemiology and Relation to Sudden Death Syndrome," Epidemiol. Rev. 3:45 (1981).
T.L. Frankovich and S. Arnon, "Clinical Trial of Botulism Immune Globulin for Infant Botulism," West J. Med. 154:103 (1991).
M. Balady, "Botulism Antitoxin Fielded for Operation Desert Storm," USAMRDC Newsletter, p. 6 (1991).
P.J. Schwarz and S.S. Arnon, "Botulism Immune Globulin for Infant Botulism Arrives–One Year and A Gulf War Later," Western J. Med. 156:197 (1992).
D.R. Peterson et al., "The Sudden Infant Death Syndrome and Infant Botulism," Rev. Infect. Dis. 1:630 (1979).
S. Arnon et al., "Intestinal Infection and Toxin Production by Clostridium Botulinum as One Cause of Sudden Infant Death Syndrome," Lancet, pp. 1273–1276, Jun. 17, 1978.
G.F. Brooks et al., (eds.) "Infections Caused by Anaerobic Bacteria," *Jawetz, Melnick, & Adelberg's Medical Microbiology*, 19th ed., pp. 257–262, Appleton & Lange, San Mateo, CA (1991).
P.G. Engelkirk et al., *Principles and Practice of Clinical Anaerobic Bacteriology*, pp. 64–67, Star Publishing Co., Belmont, CA (1992).
D.M. Lyerly et al., "Characterization of a Toxin A–Negative, Toxin B–Positive Strain of *Clostridium difficile*," Infect. Immun. 60:4633 (1992).
S.P. Borriello et al., "Virulence Factors of *Clostridium Difficile*," Rev. Infect. Dis. 12(suppl. 2):S185 (1990).
D.M. Lyerly et al., "Effects of *Clostridium difficile* Toxins Given Intragastrically to Animals," Infect. Immun., 47:349 (1985).
R.D. Rolfe, "Binding Kinetics of *Clostridium difficile* Toxins A and B to Intestinal Brush Border Membranes from Infant and Adult Hamsters," Infect. Immun., 59:1223 (1990).
Banno et al., "Biochemical Characterization and Biologic Actions of Two Toxins (D–1 and D–2) from *Clostridium difficile*," Rev. Infect. Dis., 6(Suppl. 1:S11–S20 (1984).
Rihn et al., "A New Purification Procedure for Clostridium Difficile Enterotoxin," Biochem. Biophys. Res. Comm., 124:690–695 (1984).
Justus et al., "Myoelectric Effects of *Clostridium difficile*: Motility–Altering Factors Distinct from its Cytotoxin and Enterotoxin in Rabbits," Gastroenterol., 83:836–843 (1982).

(List continued on next page.)

*Primary Examiner*—Frank C. Eisenschenk
*Attorney, Agent, or Firm*—Medlen & Carroll, LLP

[57] ABSTRACT

The present invention includes methods for the production and purification of recombinant clostridial toxin proteins.

5 Claims, 14 Drawing Sheets

OTHER PUBLICATIONS

S.M. Finegold et al., "Antimicrobial–Associated Pseudomembranous Colitis," *Clinical Guide to Anaerobic Infections*, pp. 88–89, Star Publishing Co., Belmont, CA (1992).

H.N. Benson et al., "Requirement of Avian C'1 for Fixation of Guinea Pig Complement by Avian Antibody–Antigen Complexes," J. Immunol. 87:616 (1961).

A.A. Benedict and K. Yamaga, "Immunoglobulins and Antibody Production in Avian Species," in *Comparative Immunology*(J.J. Marchaloni, ed.), pp. 335–375, Blackwell, Oxford (1966).

R. Patterson et al., "Antibody Production and Transfer to Egg Yolk in Chickens," J. Immunol. 89:272 (1962).

S.B. Carroll and B.D. Stollar, "Antibodies of Calf Thymus RNA Polymerase II from Egg Yolks of Immunized Hens," J. Biol. Chem. 258:24 (1983).

A. Polson et al., "Antibodies to Proteins from Yolk of Immunized Hens," Immunol. Comm. 9:495 (1980).

M. Delmée et al., "Characterization of Flagella of *Clostridium difficile* and Their Role in Serogrouping Reactions," J. Clin. Microbiol., 28(10):2210 (1990).

M. Delmée and V. Avesani, "Virulence of Ten Serogroups of *Clostridim difficile* in Hamsters," J. Med Microbiol., 33:85–90 (1990).

S. Toma et al., "Serotyping of *Clostridium difficile*," J. Clin. Microbiol., 26(3):426 (1988).

M. Delmée et al., "Serogrouping of *Clostridium difficile* Strains by Slide Agglutination," J. Clin. Microbiol., 21:323 (1985).

H.A. Davies and S.P. Boriello, "Detection of Capsule in Strains of *Clostriddium difficile* of Varying Virulence and Toxigenicity," Microbial Path., 9:141 (1990).

M.A.C. Edelstein, "Processing Clinical Specimens for Anaerobic Bacteria: Isolation and Identification Procedures," in S.M. Finegold et al (eds.)., *Bailey and Scott's Diagnostic Microbiology*, pp. 477–507, C.V. Mosby Co., (1990).

N.V. Padhye et al., "Production and Characterization of a Monoclonal Antibody Specific for Enterohemorrhagic *Escherichia coli* of Serotypes 0157:H7 and 026:H11," J. Clin. Microbiol. 29:99–103 (1990).

D.M. Lyerly et al., "Passive Immunization of Hamsters Against Disease Caused by *Clostridium difficile* by Use of Bovine Immunoglobulin G Concentrate," Infect. Immun., 59:2215–2218 (1991).

B.R. DasGupta & V. Sathyamoorthy, "Purification and Amino Acid Composition of Type A Botulinum Neurotoxin," Toxicon, 22:415 (1984).

B.R. Singh & B.R. DasGupta, "Molecular Differences Between Type A Botulinum Neurotoxin and Its Toxoid," Toxicon, 27:403 (1989).

H. Towbin et al., "Electrophoretic Transfer of Proteins from Polyacrylamide Gels to Nitrocellulose Sheets: Procedure and Some Applications," Proc. Nat'l Acad. Sci. USA, 76:4350 (1979).

K. Weber and M. Osborn, "Proteins and Sodium Dodecyl Sulfate: Molecular Weight Determination on Polyacrylamide Gels and Related Procedures," in *The Proteins*, 3d Edition (H. Neurath & R.L. Hill, eds), pp. 179–223, (Academic Press, NY, 1975).

S.B. Carroll and A. Laughon, "Production and Purification of Polyclonal Antibodies to the Foreign Segment of β–galactosidase Fusion Proteins," in *DNA Cloning: A Practical Approach*, vol. III, (D. Glover, ed.), pp. 89–111, IRL Press, Oxford, (1987).

B.S. Thalley and S.B. Carroll, "Rattlesnake and Scorpion Antivenoms From The Egg Yolks of Immunized Hens," Bio/Technology, 8:934–938 (1990).

I. Ohishi et al., "Oral Toxicities of *Clostridium botulinum* Toxins in Response to Molecular Size," Infect. Immun., 16:106 (1977).

B.W. Wren et al., "Antigenic Cross–Reactivity and Functional Inhibition by Antibodies to *Clostridium difficile* Toxin A, *Streptococcus mutans* Glucan–Binding Protein, and a Synthetic Peptide," Infect. Immun., 59:3151–3155 (1991).

M. Ehrich et al., "Production of *Clostridium difficile* Antitoxin," Infect. Immun. 28:1041–1043 (1980).

Z.A. McGee et al., "Local Induction of Tumor Necrosis Factor as a Molecular Mechanism of Mucosal Damage by Gonococci," Microb. Path. 12:333–341 (1992).

R. Fekety, "Animal Models of Antibiotic–Induced Colitis," in O. Zak and M. Sande (eds.), *Experimental Models in Antimicrobial Chemotherapy*, vol. 2, pp. 61–72, (1986).

S.P. Borriello et al., "*Clostridium difficile*—A Spectrum of Virulence and Analysis of Putative Virulence Determinants in the Hamster Model of Antibiotic–Associated Colitis," J. Med. Microbiol., 24:53–64 (1987).

P–H Kim et al., "Immunization of Adult Hamsters Against *Clostridium difficile*–Associated Ileocecitis and Transfer of Protection to Infant Hamsters," Infect. Immun., 55:2984–2992 (1987).

S.P. Borriello et al., "Mucosal Association by *Clostridium difficile* in The Hamster Gastrointestinal Tract," J. Med. Microbiol., 25:191–196 (1988).

C.H. Dove et al., "Molecular Characterization of the *Clostridium difficile* Toxin A Gene," Infect. Immun., 58:480–488 (1990).

J.A. Williams et al., "Preparation and Purification of Antibodies to Foreign Proteins Produced in *E. coli* Using Plasmid Expression Vectors," *DNA Cloning: Expression Systems*, in press.

C. von Eichel–Streiber and M. Sauerborn, "*Clostridium difficile* Toxin A Carries a C–Terminal Repetitive Structure Homologous to the Carbohydrate Binding Region of Streptococcal Glycosyltransferases," Gene 96:107–113 (1990).

D.M. Lyerly et al., "Nonspecific Binding of Mouse Monoclonal Antibodies to *Clostridium difficile* Toxins A and B," Curr. Microbiol., 19:303–306 (1989).

B.W. Wren and S. Tabaqchali, "Restriction Endonuclease DNA Analysis of *Clostridium difficile*," J Clin. Microbiol., 25:2402–2404 (1987).

Ausubel et al., *Current Protocols in Molecular Biology* (1989).

Sambrook et al., *Molecular Cloning, A Laboratory Manual* (1989).

Price et al., "Cloning of the Carbohydrate–binding Portion of the Toxin A Gene of *Clostridium difficile*," Curr. Microbiol., 16:55–60 (1987).

H.C. Krivan et al., "Cell Surface Binding Site for *Clostridium difficile* Enterotoxin: Evidence for a Glycoconjugate Containing the Sequence Galα1–3Galβ1–4GlcNAc," Infect. Immun., 53:573 (1986).

T.A. Mietzner et al., "A Conjugated Synthetic Peptide Corresponding to the C–terminal Region of *Clostridium perfringens* Type A Enterotoxin Elicits an Enterotoxin–Neutralizing Antibody Response in Mice," Infec. Immun., 60:3947–3951 (1992).

C. von Eichel–Streiber et al., "Cloning and Characterization of Overlapping DNA Fragments of the Toxin A Gene of *Clostridium difficile*," J. Gen. Microbiol., 135:55–64 (1989).

S. Kamiya et al., "Production of Monoclonal Antibody to *Clostridium difficile* Toxin A which Neutralises Enterotoxicity but not Haemagglutination Activity," FEMS Microbiology Lett., 81:311–316 (1991).

G.M. Thorne and S.L. Gorbach, "General Characteristics: Nomenclature of Microbial Toxins," in *Pharmacology of Bacterial Toxins, In: International Encyclopedia of Pharmacology and Therapeutics*, pp. 5–16, (Dorner and Drews, Eds.) (Pergamon Press, Oxford) (1986).

Lyerly, DM et al., "Vaccination Against Lethal *Clostridium difficile* Entrecolitis With A Nontoxic Recombinant Peptide Of Toxin A,"*Curr. Microbiol.* 21:29–32 (1990).

Phelps, CJ et al., "Construction And Expression Of The Complete *Clostridium difficile* Toxin A Gene In *Escherichia coli,"Infect. Immun.* 59:150–153 (1991).

Wren BW et al., "Molecular Cloning And Expression Of *Clostridium difficile* Toxin A In *Escherichia coli* K12," *FEBS Letters* 255:82–86 (1987).

Muldrow LL et al., "Molecular Cloning Of *Clostridium difficile* toxin A Gene Fragment In γgt11," *FEB Letters* 213:249–253 (1987).

Beitle, et al., "One–Step Purification Of A Model Periplasmic Protein From Inclusion Bodies By Its Fusion To An Effective Metal–Binding Peptide," *Biotechnol. Prog.* 9:64–69 (1993).

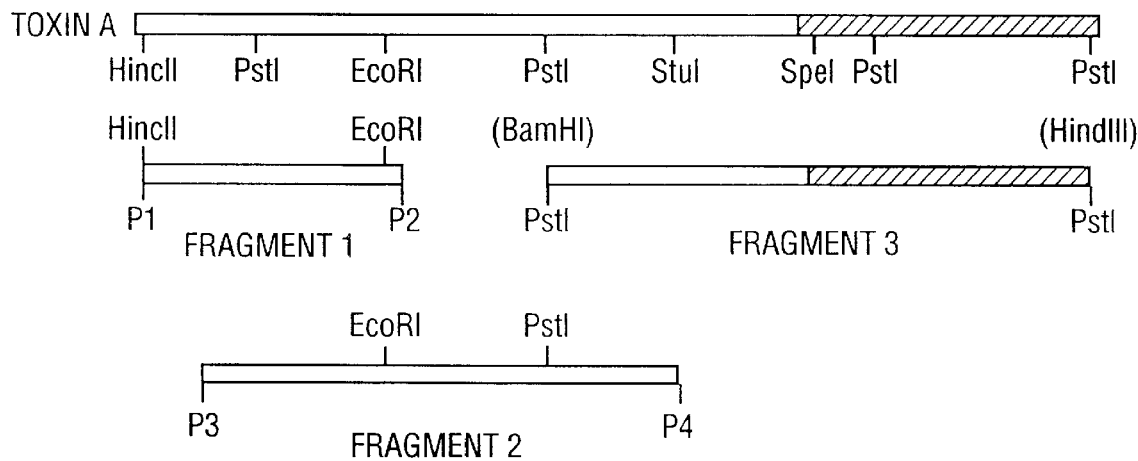
P1-P4 ARE PCR PRIMERS 1-4.
P1 = 5'GGAAATTTAGCTGCAGCATCTGAC3',
P2 = 5'TCTAGCAAATTCGCTTGTGTTGAA3',
P3 = 5'CTCGCATATAGCATTAGACC3',
P4 = 5'CTATCTAGGCCTAAAGTAT3'.
INDICATED RESTRICTION SITES IN FRAGMENTS 1 AND 2 ARE INTERNAL SITES USED TO CLONE INTO pGEX2T VECTOR (FRAGMENT 1; CONSTRUCT CALLED pGA30-660) O pP REFERS TO pET23 VECTOR, pM REFERS TO pMALc VECTOR, A REFERS TO TOXIN A, AND NUMBERS REFER TO AMINO ACID INTERVAL EXPRESSED IN CLONE. ENDPOINTS OF CLONES CORRESPOND TO INDICATED RESTRICTION SITES SHOWN OF TOXIN A MAP.

pP REFERS TO pET23 VECTOR, pM REFERS TO pMALc VECTOR, A REFERS TO TOXIN A, AND NUMBERS REFER TO AMINO ACID INTERVAL EXPRESSED IN CLONE. ENDPOINTS OF CLONES CORRESPOND TO INDICATED RESTRICTION SITES SHOWN OF TOXIN A MAP.

5,814,477

RECOMBINANT CLOSTRIDIAL TOXIN PROTEIN

This is a Divisional of application Ser. No. 08/161,907, filed on Dec. 2, 1993, now U.S. Pat. No. 5,601,823, which is Continuation-in-Part of application Ser. No. 07/985,321, filed on Dec. 4, 1992, which is a Continuation-in-Part of application Ser. No. 07/429,791, filed on Oct. 31, 1989, now issued as U.S. Pat. No. 5,196,193, on Mar. 23, 1993.

FIELD OF THE INVENTION

The present invention relates to clostridial antitoxin therapy for humans and other animals.

BACKGROUND OF THE INVENTION

The genus *Clostridium* is comprised of gram-positive, anaerobic, spore-forming bacilli. The natural habitat of these organisms is the environment and the intestinal tracts of humans and other animals. Indeed, clostridia are ubiquitous; they are commonly found in soil, dust, sewage, marine sediments, decaying vegetation, and mud. [See e.g., P. H. A. Sneath et al., "*Clostridium,*" *Bergey's Manual® of Systematic Bacteriology,* Vol. 2, pp. 1141–1200, Williams & Wilkins (1986).] Despite the identification of approximately 100 species of *Clostridium,* only a small number have been recognized as relatively common etiologic agents of medical and veterinary importance. Nonetheless, some of these species are associated with very serious diseases, including botulism, tetanus, anaerobic cellulitis, gas gangrene, bacteremia, pseudomembranous colitis, and clostridial gastroenteritis. Table 1 lists some of the species of medical and veterinary importance and the diseases with which they are associated. As virtually all of these species have been isolated from fecal samples of apparently healthy persons, some of these isolates may be transient, rather than permanent residents of the colonic flora. Nonetheless, as indicated in Table 1, the majority of these organisms may be associated with serious and/or debilitating disease. In most cases, the pathogenicity of these organisms is related to the release of powerful exotoxins or highly destructive enzymes. Indeed, several species of the genus *Clostridium* produce toxins and other enzymes of great medical and veterinary significance. [C. L. Hatheway, Clin. Microbiol. Rev. 3:66–98 (1990).]

TABLE 1

Clostridium Species of Medical and Veterinary Importance*

| Species | Disease |
|---|---|
| C. aminovalericum | Bacteriuria (pregnant women) |
| C. argentinense | Infected wounds; Bacteremia; Botulism; Infections of amniotic fluid |
| C. baratii | Infected war wounds; Peritonitis; Infectious processes of the eye, ear and prostate |
| C. beijerinckikii | Infected wounds |
| C. bifermentans | Infected wounds; Abscesses; Gas Gangrene; Bacteremia |
| C. botulinum | Food poisoning; Botulism (wound, food, infant) |
| C. butyricum | Urinary tract, lower respiratory tract, pleural cavity, and abdominal infections; Infected wounds; Abscesses; Bacteremia |
| C. cadaveris | Abscesses; Infected wounds |
| C. carnis | Soft tissue infections; Bacteremia |
| C. chauvoei | Blackleg |
| C. clostridioforme | Abdominal, cervical, scrotal, pleural, and other infections; Septicemia; Peritonitis; Appendicitis |
| C. cochlearium | Isolated from human disease processes, but role in disease unknown. |
| C. difficile | Antimicrobial-associated diarrhea; Pseudomembranous enterocolitis; Bacteremia; Pyogenic infections |
| C. fallax | Soft tissue infections |
| C. ghnoii | Soft tissue infections |
| C. glycolicum | Wound infections; Abscesses; Peritonitis |
| C. hastiforme | Infected war wounds; Bacteremia; Abscesses |
| C. histolyticum | Infected war wounds; Gas gangrene; Gingival plaque isolate |
| C. indolis | Gastrointestinal tract infections |
| C. innocuum | Gastrointestinal tract infections; Empyema |
| C. irregulare | Penile lesions |
| C. leptum | Isolated from human disease processes, but role in disease unknown. |
| C. limosum | Bacteremia; Peritonitis; Pulmonary infections |
| C. malenominatum | Various infectious processes |
| C. novyi | Infected wounds; Gas gangrene; Blackleg, Big head (ovine); Redwater disease (bovine) |
| C. oroticum | Urinary tract infections; Rectal abscesses |
| C. paraputrificum | Bacteremia; Peritonitis; Infected wounds; Appendicitis |
| C. perfringens | Gas gangrene; Anaerobic cellulitis; Intra-abdominal abscesses; Soft tissue infections; Food poisoning; Necrotizing pneumonia; Empyema; Meningitis; Bacteremia; Uterine Infections; Enteritis necrotans; Lamb dysentery; Struck; Ovine Enterotoxemia; |
| C. putrefaciens | Bacteriuria (Pregnant women with bacteremia) |
| C. putrificum | Abscesses; Infected wounds; Bacteremia |
| C. ramosum | Infections of the abdominal cavity, genital tract, lung, and biliary tract; Bacteremia |
| C. sartagoforme | Isolated from human disease processes, but role in disease unknown. |
| C. septicum | Gas gangrene; Bacteremia; Suppurative infections; Necrotizing enterocolitis; Braxy |
| C. sordellii | Gas gangrene; Wound infections; Penile lesions; Bacteremia; Abscesses; Abdominal and vaginal infections |
| C. sphenoides | Appendicitis; Bacteremia; Bone and soft tissue infections; Intraperitoneal infections; Infected war wounds; Visceral gas gangrene; Renal abscesses |
| C. sporogenes | Gas gangrene; Bacteremia; Endocarditis; central nervous system and pleuropulmonary infections; Penile lesions; Infected war wounds; Other pyogenic infections |
| C. subterminale | Bacteremia; Empyema; Biliary tract, soft tissue and bone infections |
| C. symbiosum | Liver abscesses; Bacteremia; Infections resulting due to bowel flora |
| C. tertium | Gas gangrene; Appendicitis; Brain abscesses; Intestinal tract and soft tissue infections; Infected war wounds; Periodontitis; Bacteremia |
| C. tetani | Tetanus; Infected gums and teeth; Corneal ulcerations; Mastoid and middle ear infections; Intraperitoneal infections; Tetanus neonatorum; Postpartum uterine infections; Soft tissue infections, especially related to trauma (including abrasions and lacerations); Infections related to use of contaminated needles |
| C. thermo-saccharolyticum | Isolated from human disease processes, but role in disease unknown. |

*Compiled from P. G. Engelkirk et al. "Classification", Principles and Practice of Clinical Anaerobic Bacteriology, pp. 22–23, Star Publishing Co., Belmont, CA (1992); J. Stephen and R. A. Petrowski, "Toxins Which Traverse Membranes and Deregulate Cells," in Bacterial Toxins, 2d ed., pp. 66–67, American Society for Microbiology (1986); R. Berkow and A. J. Fletcher (eds.), "Bacterial Diseases," Merck Manual of Diagnosis and Therapy, 16th ed., pp. 116–126, Merck Research Laboratories, Rahway, N.J. (1992); and O.H. Sigmund and C. M. Fraser (eds.), "Clostridial Infections," Merck Veterinary Manual, 5th ed., pp. 396–409, Merck & Co., Rahway, N.J. (1979).

Perhaps because of their significance for human and veterinary medicine, much research has been conducted on these toxins, in particular those of C. botulinum and C. difficile.

C. Botulinum

Several strains of Clostridium botulinum produce toxins of significance to human and animal health. [C. L. Hatheway, Clin. Microbiol. Rev. 3:66–98 (1990).] The effects of these toxins range from diarrheal diseases that can cause destruction of the colon, to paralytic effects that can cause death. Particularly at risk for developing clostridial diseases are neonates and humans and animals in poor health (e.g., those suffering from diseases associated with old age or immunodeficiency diseases).

Clostridium botulinum produces the most poisonous biological toxin known. The lethal human dose is a mere $10^{-9}$ mg/kg bodyweight for toxin in the bloodstream. Botulinal toxin blocks nerve transmission to the muscles, resulting in flaccid paralysis. When the toxin reaches airway and respiratory muscles, it results in respiratory failure that can cause death. [S. Arnon, J. Infect. Dis. 154:201–206 (1986).]

C. botulinum spores are carried by dust and are found on vegetables taken from the soil, on fresh fruits, and on agricultural products such as honey. Under conditions favorable to the organism, the spores germinate to vegetative cells which produces toxin. [S. Arnon, Ann. Rev. Med. 31:541 (1980).]

Botulism disease may be grouped into three types, based on the method of introduction of toxin into the bloodstream. Food-borne botulism results from ingesting improperly preserved and inadequately heated food that contains botulinal toxin. There were 355 cases of food-borne botulism in the U.S. between 1976 and 1984. [K. L. MacDonald et al., Am. J. Epidemiol. 124:794 (1986).] The death rate due to botulinal toxin is 12% and can be higher in particular risk groups. [C. O. Tacket et al., Am. J. Med. 76:794 (1984).] Wound-induced botulism results from C. botulinum penetrating traumatized tissue and producing toxin that is absorbed into the bloodstream. Since 1950, thirty cases of wound botulism have been reported. [M. N. Swartz, "Anaerobic Spore-Forming Bacilli: The Clostridia," pp. 633–646, in B. D. Davis et al.,(eds.), Microbiology 4th edition, J.B. Lippincott Co. (1990).] Infectious infant botulism results from C. botulinum colonization of the infant intestine with production of toxin and its absorption into the bloodstream. It is likely that the bacterium gains entry when spores are ingested and subsequently germinate. [S. Arnon, J. Infect. Dis. 154:201 (1986).] There have been 500 cases reported since it was first recognized in 1976. [M. N. Swartz, supra.]

Infant botulism strikes infants who are three weeks to eleven months old (greater than 90% of the cases are infants less than six months). [S. Arnon, J. Infect. Dis. 154:201 (1986).] It is believed that infants are susceptible, due, in large part, to the absence of the full adult complement of intestinal microflora. The benign microflora present in the adult intestine provide an acidic environment that is not favorable to colonization by C. botulinum. Infants begin life with a sterile intestine which is gradually colonized by microflora. Because of the limited microflora present in early infancy, the intestinal environment is not as acidic, allowing for C. botulinum spore germination, growth, and toxin production. In this regard, some adults who have undergone antibiotic therapy which alters intestinal microflora become more susceptible to botulism.

An additional factor accounting for infant susceptibility to infectious botulism is the immaturity of the infant immune system. The mature immune system is sensitized to bacterial antigens and produces protective antibodies. Secretory IgA produced in the adult intestine has the ability to agglutinate vegetative cells of C. botulinum. [S. Arnon, J. Infect. Dis. 154:201 (1986).] Secretory IgA may also act by preventing intestinal bacteria and their products from crossing the cells of the intestine. [S. Arnon, Epidemiol. Rev. 3:45 (1981).] The infant immune system is not primed to do this.

Clinical symptoms of infant botulism range from mild paralysis, to moderate and severe paralysis requiring hospitalization, to fulminant paralysis, leading to sudden death. [S. Arnon, Epidemiol. Rev. 3:45 (1981).]

The chief therapy for severe infant botulism is ventilatory assistance using a mechanical respirator and concurrent elimination of toxin and bacteria using cathartics, enemas, and gastric lavage. There were 68 hospitalizations in California for infant botulism in a single year with a total cost of over $4 million for treatment [T. L. Frankovich and S. Arnon, West. J. Med. 154:103 (1991).]

Different strains of Clostridium botulinum each produce antigenically distinct toxin designated by the letters A–G. Nearly all cases of infant botulism have been caused by bacteria producing either type A or type B toxin. (Exceptionally, one New Mexico case was caused by Clostridium botulinum producing type F toxin and another by Clostridium botulinum producing a type B-type F hybrid.) [S. Arnon, Epidemiol. Rev. 3:45 (1981).] Type C toxin affects waterfowl, type D toxin affects cattle, and type E toxin affects both humans and birds.

A trivalent antitoxin derived from horse plasma is commercially available from Connaught Industries Ltd. as a therapy for toxin types A, B, and E. However, the antitoxin has several disadvantages. First, extremely large dosages must be injected intravenously and/or intramuscularly. Second, the antitoxin has serious side effects such as acute anaphylaxis which can lead to death, and serum sickness. Finally, the efficacy of the antitoxin is uncertain and the treatment is costly. [T. O. Tacket et al., Am. J. Med. 76:794 (1984).]

A heptavalent equine botulinal antitoxin which uses only the F(ab')2 portion of the antibody molecule has been tested by the U.S. Military. [M. Balady, USAMRDC Newsletter, p. 6 (1991).] This was raised against impure toxoids in those large animals and is not a high titer preparation.

A pentavalent human antitoxin has been collected from immunized human subjects for use as a treatment for infant botulism. The supply of this antitoxin is limited and cannot be expected to meet the needs of all individuals stricken with botulism disease. In addition, collection of human sera must involve screening out HIV and other potentially serious human pathogens. [P. J. Schwarz and S. S. Arnon, Western J. Med. 156:197 (1992).]

Infant botulism has been implicated as the cause of mortality in some cases of Sudden Infant Death Syndrome (SIDS, also known as crib death). SIDS is officially recognized as infant death that is sudden and unexpected and that remained unexplained despite complete post-mortem examination. The link of SIDS to infant botulism came when fecal or blood specimens taken at autopsy from SIDS infants were found to contain C. botulinum organisms and/or toxin in 3–4% of cases analyzed. [D. R. Peterson et al., Rev. Infect. Dis. 1:630 (1979).] In contrast, only 1 of 160 healthy infants (0.6%) had C. botulinum organisms in the feces and no botulinal toxin. (S. Arnon et al., Lancet, pp. 1273–76, Jun. 17, 1978.)

In developed countries, SIDS is the number one cause of death in children between one month and one year old. (S. Arnon et al., Lancet, pp. 1273–77, Jun. 17, 1978.) More children die from SIDS in the first year than from any other single cause of death in the first fourteen years of life. In the U.S., there are 8,000–10,000 SIDS victims annually. Id.

What is needed is an effective therapy against infant botulism that is free of dangerous side effects, is available in large supply at a reasonable price, and can be safely and gently delivered so that prophylactic application to infants is feasible.

C. difficile

C. difficile, an organism which gained its name due to difficulties encountered in its isolation, has recently been proven to be an etiologic agent of diarrheal disease. (Sneath et al., p. 1165.). C. difficile is present in the gastrointestinal tract of approximately 3% of healthy adults, and 10–30% of neonates without adverse effect (Swartz, at p. 644); by other estimates, C. difficile is a part of the normal gastrointestinal flora of 2–10% of humans. [G. F. Brooks et al., (eds.) "Infections Caused by Anaerobic Bacteria," Jawetz, Melnick, & Adelber's Medical Microbiology, 19th ed., pp. 257–262, Appleton & Lange, San Mateo, Calif. (1991).] As these organisms are relatively resistant to most commonly used antimicrobials, when a patient is treated with antibiotics, the other members of the normal gastrointestinal flora are suppressed and C. difficile flourishes, producing cytopathic toxins and enterotoxins. It has been found in 25% of cases of moderate diarrhea resulting from treatment with antibiotics, especially the cephalosporins, clindamycin, and ampicillin. [M. N. Swartz at 644.]

Importantly, C. difficile is commonly associated with nosocomial infections. The organism is often present in the hospital and nursing home environments and may be carried on the hands and clothing of hospital personnel who care for debilitated and immunocompromised patients. As many of these patients are being treated with antimicrobials or other chemotherapeutic agents, such transmission of C. difficile represents a significant risk factor for disease. (Engelkirk et al., pp. 64–67.)

C. difficile is associated with a range of diarrhetic illness, ranging from diarrhea alone to marked diarrhea and necrosis of the gastrointestinal mucosa with the accumulation of inflammatory cells and fibrin, which forms a pseudomembrane in the affected area. (Brooks et al.) It has been found in over 95% of pseudomembranous enterocolitis cases. (Swartz, at p. 644.) This occasionally fatal disease is characterized by diarrhea, multiple small colonic plaques, and toxic megacolon. (Swartz, at p. 644.) Although stool cultures are sometimes used for diagnosis, diagnosis is best made by detection of the heat labile toxins present in fecal filtrates from patients with enterocolitis due to C. difficile. (Swartz, at p. 644–645; and Brooks et al., at p. 260.) C. difficile toxins are cytotoxic for tissue/cell cultures and cause enterocolitis when injected intracecally into hamsters. (Swartz, at p. 644.)

The enterotoxicity of C. difficile is primarily due to the action of two toxins, designated A and B, each of approximately 300,000 in molecular weight. Both are potent cytotoxins, with toxin A possessing direct enterocytotoxic activity. [Lyerly et al., Infect. Immun. 60:4633 (1992)] Unlike toxin A of C. perfringens, an organism rarely associated with antimicrobial-associated diarrhea, the toxin of C. difficile is not a spore coat constituent and is not produced during sporulation. (Swartz, at p. 644.) C. difficile toxin A causes fluid accumulation and mucosal damage in rabbit ileal loops and appears to increase the uptake of toxin B by the intestinal mucosa. Toxin B does not cause intestinal fluid accumulation, but it is 1000 times more toxic than toxin A to tissue culture cells and causes membrane damage. Both toxins are important in disease. [Borriello et al., Rev. Infect. Dis., 12(suppl. 2):S185 (1990); Lyerly et al., Infect. Immun., 47:349 (1985); and Rolfe, Infect. Immun., 59:1223 (1990).]

C. difficile has also been reported to produce other toxins such as an enterotoxin different from toxins A and B [Banno et al., Rev. Infect. Dis., 6(Suppl. 1:S11–S20 (1984)], a low molecular weight toxin [Rihn et al., Biochem. Biophys. Res. Comm., 124:690–695 (1984)], a motility altering factor [Justus et al., Gastroenterol., 83:836–843 (1982)], and perhaps other toxins. Regardless, C. difficile gastrointestinal disease is of primary concern.

It is significant that due to its resistance to most commonly used antimicrobials, C. difficile is associated with antimicrobial therapy with virtually all antimicrobial agents (although most commonly ampicillin, clindamycin and cephalosporins). It is also associated with disease in patients undergoing chemotherapy with such compounds as methotrexate, 5-fluorouracil, cyclophosphamide, and doxorubicin. [S. M. Finegold et al., Clinical Guide to Anaerobic Infections, pp. 88–89, Star Publishing Co., Belmont, Calif. (1992).]

Treatment of C. difficile disease is problematic, given the high resistance of the organism. Oral metronidazole, bacitracin and vancomycin have been reported to be effective. (Finegold et al., p. 89.) However there are problems associated with treatment utilizing these compounds. Vancomycin is very expensive, some patients are unable to take oral medication, and the relapse rate is high (20–25%), although it may not occur for several weeks. Id.

C. difficile disease would be prevented or treated by neutralizing the effects of these toxins in the gastrointestinal tract. Thus, what is needed is an effective therapy against C. difficile toxin that is free of dangerous side effects, is available in large supply at a reasonable price, and can be safely delivered so that prophylactic application to patients at risk of developing pseudomembranous enterocolitis can be effectively treated.

DESCRIPTION OF THE DRAWINGS

FIG. 6 is a restriction map of C. difficile toxin A gene, showing sequences of primers 1-4 (SEQ ID NOS:1–4).

SUMMARY OF THE INVENTION

Figure 1:
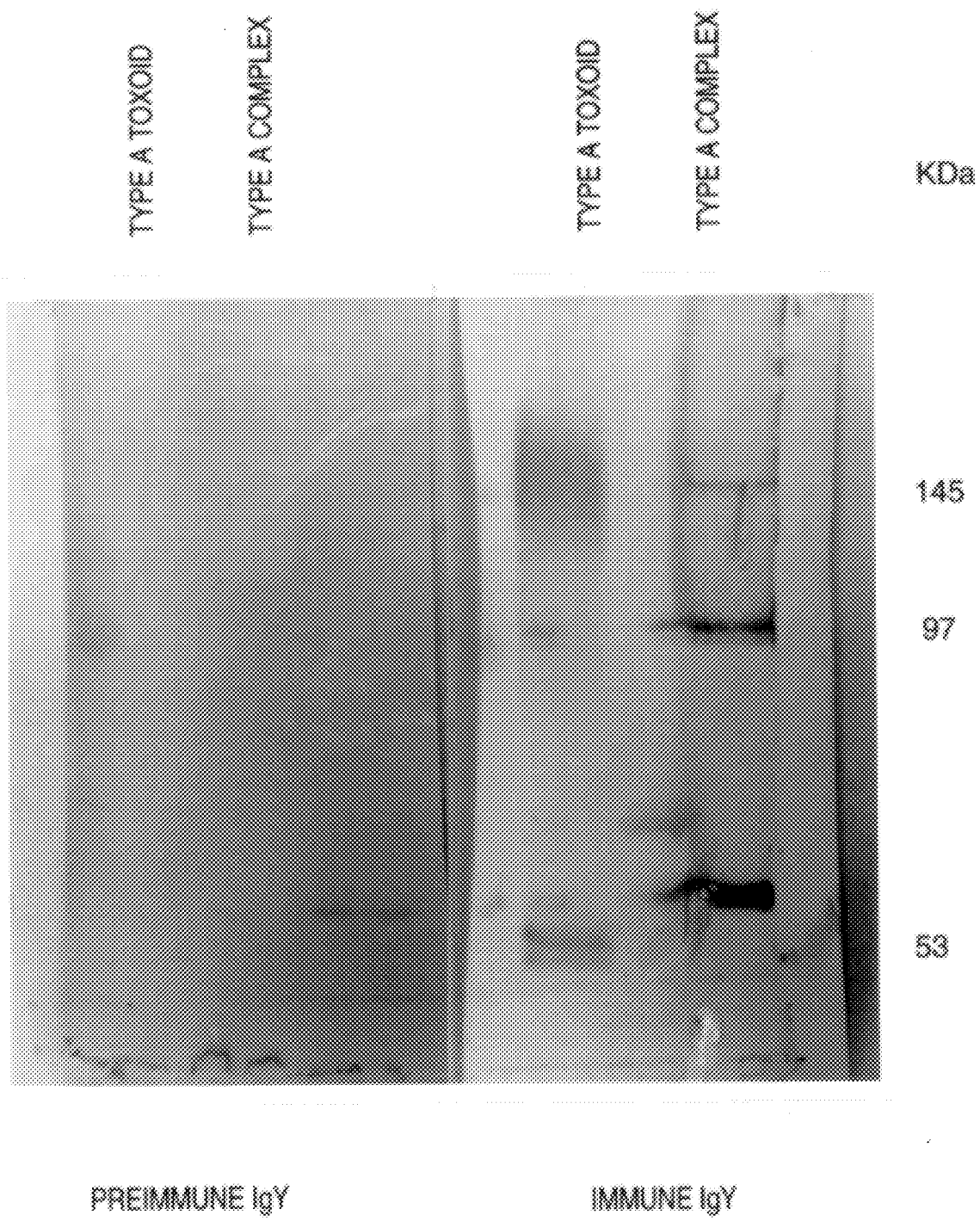
FIG. 1 shows the reactivity of anti-C. botulinum IgY by Western blot.

The present invention contemplates treating humans and other animals intoxicated with a bacterial toxin by oral administration of antitoxin raised against the toxin. In one embodiment, the present invention contemplates a method of treatment comprising: a) providing: i) a subject exposed to at least one clostridial toxin; ii) an avian neutralizing antitoxin in a therapeutic amount that is orally administrable; and b) orally administering the antitoxin to the subject, wherein the subject has not been previously treated with neutralizing antitoxin. In a preferred embodiment, the antitoxin comprises *Clostridium difficile* antitoxin. In a preferred embodiment, antitoxin is administered in an aqueous solution. In another preferred embodiment, the aqueous solution is a nutritional formula. In an alternative embodiment the nutritional formula comprises infant formula.

The present invention further contemplates a method of prophylactic treatment comprising: a) providing: i) an avian antibody capable of neutralizing at least one *Clostridium difficile* toxin, the antibody being in therapeutic amount that is orally administrable, ii) a subject; and b) orally administering the antibody to the subject prior to exposure of the subject to *Clostridium difficile* toxin. In one embodiment, the antitoxin is administered in an aqueous solution. In a preferred embodiment, the aqueous solution is a nutritional formula. In an alternative embodiment the nutritional formula comprises infant formula.

The present invention also contemplates a method of treatment comprising: a) providing: i) a purified *Clostridium difficile* toxin, and ii) an avian host; b) immunizing the host with the purified *Clostridium difficile* toxin so as to generate a neutralizing antitoxin; and c) orally administering the neutralizing antitoxin in a therapeutic amount to a subject exposed to the toxin. In one embodiment, the antitoxin is administered in an aqueous solution. In a preferred embodiment, the aqueous solution is a nutritional formula. In an alternative embodiment the nutritional formula comprises infant formula.

The present invention also contemplates a composition comprising avian antitoxin directed against at least one *Clostridium difficile* toxin in therapeutic amounts. In one embodiment, the antitoxin is orally administrable. In a preferred embodiment, the aqueous solution is a nutritional formula In an alternative embodiment the nutritional formula comprises infant formula In a preferred embodiment, the antitoxin composition is directed against a portion of at least one *Clostridium difficile* toxin.

The present invention further contemplates a method of producing clostridial toxin comprising: a) providing a host cell overproducing a portion of clostridial toxin, wherein the portion comprises one or more intervals of the toxin; and b) purifying the toxin portion. In one embodiment, the interval is interval 6. In another embodiment, the interval further comprises a ligand-binding domain. In one preferred embodiment, the host cell is *Escherichia coli*. In another preferred embodiment, the clostridial toxin is a toxin produced by *Clostridium difficile*.

The present invention also contemplates a method of immunizing a host to produce antitoxin directed against clostridial toxin comprising: a) providing in any order: i) a host, and ii) one or more intervals of clostridial toxin; and b) immunizing the host with purified clostridial toxin so as to generate antitoxin. It is also contemplated that the antitoxin be collected from the host. It is further contemplated that the collected antitoxin will be purified. In one preferred embodiment the host is an avian species. In another preferred embodiment, the clostridial toxin is a toxin produced by *Clostridium difficile*. In an additional preferred embodiment, the antitoxin is capable of neutralizing clostridial toxin.

The present invention also contemplates a method of treatment comprising: a) providing: i) a subject exposed to at least one clostridial toxin, and ii) at least one neutralizing antitoxin directed against one or more intervals of clostridial toxin; and b) orally administering antitoxin to the subject. In a preferred embodiment the neutralizing antitoxin is an avian antitoxin In another preferred embodiment, the clostridial toxin is a toxin produced by *Clostridium difficile*. In an alternative embodiment, the antitoxin is directed against interval 6 of *Clostridium difficile* toxin A.

DESCRIPTION OF THE INVENTION

The present invention contemplates treating humans and other animals intoxicated with at least one bacterial toxin. It is contemplated that oral administration of antitoxin will be used to treat patients effected by or at risk of symptoms due to the action of bacterial toxins. The organisms, toxins and individual steps of the present invention are described separately below.

I. *Clostridium* Species, Clostridial Diseases And Associated Toxins

A preferred embodiment of the method of the present invention is directed toward obtaining antibodies against *Clostridium* species, their toxins, enzymes or other metabolic by-products, cell wall components, or synthetic or recombinant versions of any of these compounds. It is contemplated that these antibodies will be produced by immunization of humans or other animals. It is not intended that the present invention be limited to any particular toxin or any species of organism. In one embodiment, toxins from all *Clostridium* species are contemplated as immunogens. Examples of these toxins include the neuraminidase toxin of *C. butyricum*, *C. sordellii* toxins HT and LT, and the numerous *C. perfringens* toxins. In one preferred embodiment, toxins A, B, C, D, E, F, and G of *C. botulinum* are contemplated as immunogens. In another preferred embodiment, toxins A and B of *C. difficile* are contemplated as immunogens. Table 2 above lists various *Clostridium* species, their toxins and some antigens associated with disease.

TABLE 2

Clostridial Toxins

| Organism | Toxins and Disease-Associated Antigens |
|---|---|
| *C. botulinum* | A, B, $C_1$, $C_2$, D, E, F, G |
| *C. butyricum* | Neuraminidase |
| *C. difficile* | A, B, Enterotoxin (not A nor B), Motility Altering Factor, Low Molecular Weight Toxin, Others |
| *C. perfringens* | α, β, ε, ι, γ, δ, ν, θ, κ, λ, μ, υ |
| *C. sordellii*/ *C. bifermentans* | HT, LT, α, β, γ |
| *C. novyi* | α, β, γ, δ, ε, ζ, ν, θ |
| *C. septicum* | α, β, γ, δ |
| *C. histolyticum* | α, β, γ, δ, ε plus additional enzymes |
| *C. chauvoei* | α, β, γ, δ |

It is not intended that antibodies produced against one toxin will only be used against that toxin. It is contemplated that antibodies directed against one toxin (e.g., *C. perfringens* type A enterotoxin) may be used as an effective therapeutic against one or more toxin(s) produced by other members of the genus *Clostridium* or other toxin producing organisms (e.g., *Bacillus cereus, Staphylococcus aureus, Streptococcus mutans, Acinetobacter calcoaceticus,*

*Pseudomonas aeruginosa,* other *Pseudomonas* species, etc.). It is further contemplated that antibodies directed against the portion of the toxin which binds to mammalian membranes (e.g., *C. perfringens* enterotoxin A) can also be used against other organisms. It is contemplated that these membrane binding domains are produced synthetically and used as immunogens.

II. Obtaining Antibodies In Non-Mammals

A preferred embodiment of the method of the present invention for obtaining antibodies involves immunization. However, it is also contemplated that antibodies could be obtained from non-mammals without immunization. In the case where no immunization is contemplated, the present invention may use non-mammals with preexisting antibodies to toxins as well as non-mammals that have antibodies to whole organisms by virtue of reactions with the administered antigen. An example of the latter involves immunization with synthetic peptides or recombinant proteins sharing epitopes with whole organism components.

In a preferred embodiment, the method of the present invention contemplates immunizing non-mammals with bacterial toxin(s). It is not intended that the present invention be limited to any particular toxin. In one embodiment, toxin from all clostridial bacteria sources (see Table 2) are contemplated as immunogens. Examples of these toxins are *C. butyricum* neuraminidase toxin, *C. difficile* toxins A and B, *C. perfringens* toxins α, β, ε, and ι, and *C. sordellii* toxins HT and LT. In a preferred embodiment, toxins A, B, C, D, E, F, and G from *C. botulinum* are contemplated as immunogens.

When immunization is used, the preferred non-mammal is from the class *Aves*. All birds are contemplated (e.g., duck, ostrich, emu, turkey, etc.). A preferred bird is a chicken. Importantly, chicken antibody does not fix mammalian complement. [See H. N. Benson et al., J. Immunol. 87:616 (1961).] Thus, chicken antibody will normally not cause a complement-dependent reaction. [A. A. Benedict and K. Yamaga, *"Immunoglobulins and Antibody Production in Avian Species,"* in *Comparative Immunology* (J. J. Marchaloni, ed.), pp. 335–375, Blackwell, Oxford (1966).] Thus, the preferred antitoxins of the present invention will not exhibit complement-related side effects observed with antitoxins known presently.

When birds are used, it is contemplated that the antibody will be obtained from either the bird serum or the egg. A preferred embodiment involves collection of the antibody from the egg. Laying hens transport immunoglobulin to the egg yolk ("IgY") in concentrations equal to or exceeding that found in serum. [See R. Patterson et al., J. Immunol. 89:272 (1962); and S. B. Carroll and B. D. Stollar, J. Biol. Chem. 258:24 (1983).] In addition, the large volume of egg yolk produced vastly exceeds the volume of serum that can be safely obtained from the bird over any given time period. Finally, the antibody from eggs is purer and more homogeneous; there is far less non-immunoglobulin protein (as compared to serum) and only one class of immunoglobulin is transported to the yolk.

When considering immunization with toxins, one may consider modification of the toxins to reduce the toxicity. In this regard, it is not intended that the present invention be limited by immunization with modified toxin. Unmodified ("native") toxin is also contemplated as an immunogen.

It is also not intended that the present invention be limited by the type of modification—if modification is used. The present invention contemplates all types of toxin modification, including chemical and heat treatment of the toxin. The preferred modification, however, is formaldehyde treatment.

It is not intended that the present invention be limited to a particular mode of immunization; the present invention contemplates all modes of immunization, including subcutaneous, intramuscular, intraperitoneal, and intravenous or intravascular injection, as well as per os administration of immunogen.

The present invention further contemplates immunization with or without adjuvant. (Adjuvant is defined as a substance known to increase the immune response to other antigens when administered with other antigens.) If adjuvant is used, it is not intended that the present invention be limited to any particular type of adjuvant—or that the same adjuvant, once used, be used all the time. While the present invention contemplates all types of adjuvant, whether used separately or in combinations, the preferred use of adjuvant is the use of Complete Freund's Adjuvant followed sometime later with Incomplete Freund's Adjuvant.

When immunization is used, the present invention contemplates a wide variety of immunization schedules. In one embodiment, a chicken is administered toxin(s) on day zero and subsequently receives toxin(s) in intervals thereafter. It is not intended that the present invention be limited by the particular intervals or doses. Similarly, it is not intended that the present invention be limited to any particular schedule for collecting antibody. The preferred collection time is sometime after day 100.

Where birds are used and collection of antibody is performed by collecting eggs, the eggs may be stored prior to processing for antibody. It is preferred that eggs be stored at 4° C. for less than one year.

It is contemplated that chicken antibody produced in this manner can be buffer-extracted and used analytically. While unpurified, this preparation can serve as a reference for activity of the antibody prior to further manipulations (e.g., immunoaffinity purification).

III. Increasing the Effectiveness of Antibodies

When purification is used, the present invention contemplates purifying to increase the effectiveness of both non-mammalian antitoxins and mammalian antitoxins. Specifically, the present invention contemplates increasing the percent of toxin-reactive immunoglobulin. The preferred purification approach for avian antibody is polyethylene glycol (PEG) separation.

The present invention contemplates that avian antibody be initially purified using simple, inexpensive procedures. In one embodiment, chicken antibody from eggs is purified by extraction and precipitation with PEG. PEG purification exploits the differential solubility of lipids (which are abundant in egg yolks) and yolk proteins in high concentrations of PEG 8000. [Polson et al., Immunol. Comm. 9:495 (1980) .] The technique is rapid, simple, and relatively inexpensive and yields an immunoglobulin fraction that is significantly purer in terms of contaminating non-immunoglobulin proteins than the comparable ammonium sulfate fractions of mammalian sera and horse antibodies. Indeed, PEG-purified antibody is sufficiently pure that the present invention contemplates the use of PEG-purified antitoxins in the passive immunization of intoxicated humans and animals.

IV. Treatment

The present invention contemplates antitoxin therapy for humans and other animals intoxicated by bacterial toxins. A preferred method of treatment is by oral administration of antitoxin.

A. Dosage of Antitoxin

It was noted by way of background that a balance must be struck when administering currently available antitoxin which is usually produced in large animals such as horses;

sufficient antitoxin must be administered to neutralize the toxin, but not so much antitoxin as to increase the risk of untoward side effects. These side effects are caused by: i) patient sensitivity to foreign (e.g., horse) proteins; ii) anaphylactic or immunogenic properties of non-immunoglobulin proteins; iii) the complement fixing properties of mammalian antibodies; and/or iv) the overall burden of foreign protein administered. It is extremely difficult to strike this balance when, as noted above, the degree of intoxication (and hence the level of antitoxin therapy needed) can only be approximated.

The present invention contemplates significantly reducing side effects so that this balance is more easily achieved. Treatment according to the present invention contemplates reducing side effects by using PEG-purified antitoxin from birds.

In one embodiment, the treatment of the present invention contemplates the use of PEG-purified antitoxin from birds. The use of yolk-derived, PEG-purified antibody as antitoxin allows for the administration of: 1) non(mammalian)-complement-fixing, avian antibody; 2) a less heterogeneous mixture of non-immunoglobulin proteins; and 3) less total protein to deliver the equivalent weight of active antibody present in currently available antitoxins. The non-mammalian source of the antitoxin makes it useful for treating patients who are sensitive to horse or other mammalian sera.

B. Delivery Of Antitoxin

Although it is not intended to limit the route of delivery, the present invention contemplates a method for antitoxin treatment of bacterial intoxication in which delivery of antitoxin is oral. In one embodiment, antitoxin is delivered in a solid form (e.g., tablets). In an alternative embodiment antitoxin is delivered in an aqueous solution. When an aqueous solution is used, the solution has sufficient ionic strength to solubilize antibody protein, yet is made palatable for oral administration. In one embodiment the delivery solution is an aqueous solution. In another embodiment the delivery solution is a nutritional formula. Preferably, the delivery solution is infant formula.

The invention contemplates a method of treatment which can be administered for treatment of acute intoxication. In one embodiment, antitoxin is administered orally in either a delivery solution or in tablet form, in therapeutic dosage, to a subject intoxicated by the bacterial toxin which served as immunogen for the antitoxin.

The invention also contemplates a method of treatment which can be administered prophylactically. In one embodiment, antitoxin is administered orally, in a delivery solution, in therapeutic dosage, to a subject, to prevent intoxication of the subject by the bacterial toxin which served as immunogen for the production of antitoxin. In another embodiment, antitoxin is administered orally in solid form such as tablets. In one preferred embodiment the subject is an infant. In another embodiment, antibody raised against whole bacterial organism is administered orally to a subject, in a delivery solution, in therapeutic dosage.

V. Detection of Toxin

The invention contemplates detecting bacterial toxin in a sample. The term "sample" in the present specification and claims is used in its broadest sense. On the one hand it is meant to include a specimen or culture. On the other hand, it is meant to include both biological and environmental samples.

Biological samples may be animal, including human, fluid or tissue; liquid and solid food products and ingredients such as dairy items, vegetables, meat and meat by-products, and waste. Environmental samples include environmental material such as surface matter, soil, water and industrial samples, as well as samples obtained from food and dairy processing instruments, apparatus, equipment, disposable and non-disposable items. These examples are not to be construed as limiting the sample types applicable to the present invention.

The invention contemplates detecting bacterial toxin by a method that utilizes antitoxin raised against the toxin and a reporter substance. The reporter substance comprises an antibody with binding specificity for the antitoxin attached to a molecule which is used to identify the presence of the reporter substance. The biological tissue is first exposed to antitoxin which binds to toxin and is then washed free of substantially all unbound antitoxin. The biological tissue is next exposed to the reporter substance, which binds to antitoxin and is then washed free of substantially all unbound reporter substance. Identification of the reporter substance in the biological tissue indicates the presence of the bacterial toxin.

It is also contemplated that bacterial toxin be detected by pouring liquids (e.g., soups and other fluid foods and feeds including nutritional supplements for humans and other animals) over immobilized antibody which is directed against the bacterial toxin. It is contemplated that the immobilized antibody will be present in or on such supports as cartridges, columns, beads, or any other solid support medium. In one embodiment, following the exposure of the liquid to the immobilized antibody, unbound toxin is substantially removed by washing. The toxin which is bound to antibody is then exposed to a reporter substance which detects the presence of bound toxin. In a preferred embodiment the reporter substance is an enzyme, fluorescent dye, or radioactive compound attached to an antibody which is directed against the toxin (i.e., in a "sandwich" immunoassay). It is also contemplated that the detection system will be developed as necessary (e.g., the addition of enzyme substrate in enzyme systems; observation using fluorescent light for fluorescent dye systems; and quantitation of radioactivity for radioactive systems).

EXPERIMENTAL

The following examples serve to illustrate certain preferred embodiments and aspects of the present invention and are not to be construed as limiting the scope thereof.

In the disclosure which follows, the following abbreviations apply: °C. (degrees Centigrade); rpm (revolutions per minute); BBS-Tween (borate buffered saline containing Tween); BSA (bovine serum albumin); ELISA (enzyme-linked immunosorbent assay); CFA (complete Freund's adjuvant); IFA (incomplete Freund's adjuvant); IgG (immunoglobulin G); IgY (immunoglobulin Y); I.M. (intramuscular); I.V. (intravenous or intravascular); $H_2O$ (water); HCl (hydrochloric acid); $LD_{100}$ (lethal dose for 100% of experimental animals); kD (kilodaltons); gm (grams); $\mu$g (micrograms); mg (milligrams); ng (nanograms); $\mu$l (microliters); ml (milliliters); mm (millimeters); nm (nanometers); $\mu$m (micrometer); M (molar); mM (millimolar); MW (molecular weight); sec (seconds); min(s) (minute/minutes); hr(s) (hour/hours); $MgCl_2$ (magnesium chloride); NaCl (sodium chloride); $Na_2CO_3$ (sodium carbonate); $OD_{280}$ (optical density at 280 nm); $OD_{600}$ (optical density at 600 $\mu$m); PAGE (polyacrylamide gel electrophoresis); PBS [phosphate buffered saline (150 mM NaCl, 10 mM sodium phosphate buffer, pH 7.2)]; PEG (polyethylene glycol); SDS (sodium dodecyl sulfate); Tris (tris(hydroxymethyl)aminomethane); Ensure®

(Ensure®, Ross Laboratories, Columbus Ohio); Enfamil® (Enfamil®, Mead Johnson); w/v (weight to volume); v/v (volume to volume); Amicon (Amicon, Inc., Beverly, Mass.); Amresco (Amresco, Inc., Solon, Ohio); ATCC (American Type Culture Collection, Rockville, Md.); BBL (Baltimore Biologics Laboratory, (a division of Becton Dickinson), Cockeysville, Md.); Becton Dickinson (Becton Dickinson Labware, Lincoln Park, N.J.); BioRad (BioRad, Richmond, Calif.); Charles River (Charles River Laboratories, Wilmington, Mass.); Cocalico (Cocalico Biologicals Inc., Reamstown, Pa.); CytRx (CytRx Corp., Norcross, Ga.); Falcon (e.g. Baxter Healthcare Corp., McGaw Park, Ill. and Becton Dickinson); Fisher Biotech (Fisher Biotech, Springfield, N.J.); GIBCO (Grand Island Biologic Company/BRL, Grand Island, N.Y.); Harlan Sprague Dawley (Harlan Sprague Dawley, Inc., Madison, Wis.); Mallinckrodt (a division of Baxter Healthcare Corp., McGaw Park, Ill.); Millipore (Millipore Corp., Marlborough, Mass.); New England Biolabs (New England Biolabs, Inc., Beverly, Mass.); Novagen (Novagen, Inc., Madison, Wis.); Sigma (Sigma Chemical Co., St. Louis, Mo.); Pharmacia (Pharmacia, Inc., Piscataway, N.J.); Sterogene (Sterogene, Inc., Arcadia, Calif.); Tech Lab (Tech Lab, Inc., Blacksburg, Va.).

EXAMPLE 1

Production Of High-Titer Antibodies To *Clostridium difficile* Organisms in a Hen Antibodies to certain pathogenic organisms have been shown to be effective in treating diseases caused by those organisms. It has not been shown whether antibodies can be raised, against *Clostridium difficile,* which would be effective in treating infection by this organism. Accordingly, *C. difficile* was tested as immunogen for production of hen antibodies.

To determine the best course for raising high-titer egg antibodies against whole *C. difficile* organisms, different immunizing strains and different immunizing concentrations were examined. The example involved (a) preparation of the bacterial immunogen, (b) immunization, (c) purification of anti-bacterial chicken antibodies, and (d) detection of anti-bacterial antibodies in the purified IgY preparations.

(a) Preparation of Bacterial Immunogen. *C. difficile* Strains 43594 (serogroup A) and 43596 (serogroup C) were originally obtained from the ATCC. These two strains were selected because they represent two of the most commonly-occurring serogroups isolated from patients with antibiotic-associated pseudomembranous colitis. [Delmee et al., J. Clin. Microbiol., 28(10):2210 (1990).] Additionally, both of these strains have been previously characterized with respect to their virulence in the Syrian hamster model for *C. difficile* infection. [Delmee et al., J. Med Microbiol., 33:85 (1990).]

The bacterial strains were separately cultured on brain heart infusion agar for 48 hours at 37° C. in a Gas Pack 100 Jar (BBL, Cockeysville, Md.) equipped with a Gas Pack Plus anaerobic envelope (BBL). Forty-eight hour cultures were used because they produce better growth and the organisms have been found to be more cross-reactive with respect to their surface antigen presentation. The greater the degree of cross-reactivity of our IgY preparations, the better the probability of a broad range of activity against different strains/serogroups. [Toma et al., J. Clin. Microbiol., 26(3):426 (1988).]

The resulting organisms were removed from the agar surface using a sterile dacron-tip swab, and were suspended in a solution containing 0.4% formaldehyde in PBS, pH 7.2. This concentration of formaldehyde has been reported as producing good results for the purpose of preparing whole-organism immunogen suspensions for the generation of polyclonal anti-*C. difficile* antisera in rabbits. [Delmee et al., J. Clin. Microbiol., 21:323 (1985); Davies et al., Microbial Path., 9:141 (1990).] In this manner, two separate bacterial suspensions were prepared, one for each strain. The two suspensions were then incubated at 4° C. for 1 hour. Following this period of formalin-treatment, the suspensions were centrifuged at 4,200×g for 20 min., and the resulting pellets were washed twice in normal saline. The washed pellets, which contained formalin-treated whole organisms, were resuspended in fresh normal saline such that the visual turbidity of each suspension corresponded to a #7 McFarland standard. [M. A. C. Edelstein, *"Processing Clinical Specimens for Anaerobic Bacteria: Isolation and Identification Procedures,"* in S. M. Finegold et al (eds.)., *Bailey and Scott's Diagnostic Microbiology,* pp. 477–507, C.V. Mosby Co., (1990). The preparation of McFarland nephelometer standards and the corresponding approximate number of organisms for each tube are described in detail at pp. 172–173 of this volume.] Each of the two #7 suspensions was then split into two separate volumes. One volume of each suspension was volumetrically adjusted, by the addition of saline, to correspond to the visual turbidity of a #1 McFarland standard. [Id.] The #1 suspensions contained approximately $3 \times 10^8$ organisms/ml, and the #7 suspensions contained approximately $2 \times 10^9$ organisms/ml. [Id.] The four resulting concentration-adjusted suspensions of formalin-treated *C. difficile* organisms were considered to be "bacterial immunogen suspensions." These suspensions were used immediately after preparation for the initial immunization. [See section (b).]

The formalin-treatment procedure did not result in 100% non-viable bacteria in the immunogen suspensions. In order to increase the level of killing, the formalin concentration and length of treatment were both increased for subsequent immunogen preparations, as described below in Table 3. (Although viability was decreased with the stronger formalin treatment, 100% inviability of the bacterial immunogen suspensions was not reached.) Also, in subsequent immunogen preparations, the formalin solutions were prepared in normal saline instead of PBS. At day 49, the day of the fifth immunization, the excess volumes of the four previous bacterial immunogen suspensions were stored frozen at −70° C. for use during all subsequent immunizations.

(b) Immunization. For the initial immunization, 1.0 ml volumes of each of the four bacterial immunogen suspensions described above were separately emulsified in 1.2 ml volumes of CFA (GIBCO). For each of the four emulsified immunogen suspensions, two four-month old White Leghorn hens (pre-laying) were immunized. (It is not necessary to use pre-laying hens; actively-laying hens can also be utilized.) Each hen received a total volume of approximately 1.0 ml of a single emulsified immunogen suspension via four injections (two subcutaneous and two intramuscular) of approximately 250 μl per site. In this manner, a total of four different immunization combinations, using two hens per combination, were initiated for the purpose of evaluating both the effect of immunizing concentration on egg yolk antibody (IgY) production, and interstrain cross-reactivity of IgY raised against heterologous strains. The four immunization groups are summarized in Table 3.

The time point for the first series of immunizations was designated as "day zero." All subsequent immunizations were performed as described above except that the bacterial immunogen suspensions were emulsified using IFA (GIBCO) instead of CFA, and for the later time point immunization, the stored frozen suspensions were used instead of freshly-prepared suspensions. The immunization schedule used is listed in Table 4.

TABLE 3

Immunization Groups

| GROUP DESIGNATION | IMMUNIZING STRAIN | APPROXIMATE IMMUNIZING DOSE |
|---|---|---|
| CD 43594, #1 | C. difficile strain 43594 | $1.5 \times 10^8$ organisms/hen |
| CD 43594, #7 | C. difficile strain 43594 | $1.0 \times 10^9$ organisms/hen |
| CD 43596, #1 | C. difficile strain 43596 | $1.5 \times 10^8$ organisms/hen |
| CD 43596, #7 | C. difficile strain 43596 | $1.5 \times 10^9$ organisms/hen |

(c) Purification of Anti-Bacterial Chicken Antibodies. Groups of four eggs were collected per immunization group between days 80 and 84 post-initial immunization, and chicken immunoglobulin (IgY) was extracted according to a modification of the procedure of A. Polson et al., Immunol. Comm., 9:495 (1980). A gentle stream of distilled water from a squirt bottle was used to separate the yolks from the whites, and the yolks were broken by dropping them through a funnel into a graduated cylinder. The four individual yolks were pooled for each group. The pooled, broken yolks were blended with 4 volumes of egg extraction buffer to improve antibody yield (egg extraction buffer is 0.01M sodium phosphate, 0.1M NaCl, pH 7.5, containing 0.005% thimerosal), and PEG 8000 (Amresco) was added to a concentration of 3.5%. When all the PEG dissolved, the protein precipitates that formed were pelleted by centrifugation at 13,000×g for 10 minutes. The supernatants were decanted and filtered through cheesecloth to remove the lipid layer, and the PEG was added to the supernatants to a final concentration of 12% (the supernatants were assumed to contain 3.5% PEG). After a second centrifugation, the supernatants were discarded and the pellets were centrifuged a final time to extrude the remaining PEG. These crude IgY pellets were then dissolved in the original yolk volume of egg extraction buffer and stored at 4° C. As an additional control, a preimmune IgY solution was prepared as described above, using eggs collected from unimmunized hens.

TABLE 4

Immunization Schedule

| DAY OF IMMUNIZATION | FORMALIN- TREATMENT | IMMUNOGEN PREPARATION USED |
|---|---|---|
| 0 | 1%, 1 hr. | freshly-prepared |
| 14 | 1%, overnight | " |
| 21 | 1%, overnight | " |
| 35 | 1%, 48 hrs. | " |
| 49 | 1%, 72 hrs. | " |
| 70 | " | stored frozen |
| 85 | " | " |
| 105 | " | " |

(d) Detection of Anti-Bacterial Antibodies In The Purified IgY Preparations. In order to evaluate the relative levels of specific anti-C. difficile activity in the IgY preparations described above, a modified version of the whole-organism ELISA procedure of N. V. Padhye et al., J. Clin. Microbiol. 29:99–103 (1990) was used. Frozen organisms of both C. difficile strains described above were thawed and diluted to a concentration of approximately $1 \times 10^7$ organisms/ml using PBS, pH 7.2. In this way, two separate coating suspensions were prepared, one for each immunizing strain. Into the wells of 96-well microtiter plates (Falcon, Pro-Bind Assay Plates) were placed 100 μl volumes of the coating suspensions. In this manner, each plate well received a total of approximately $1 \times 10^6$ organisms of one strain or the other. The plates were then incubated at 4° C. overnight. The next morning, the coating suspensions were decanted, and all wells were washed three times using PBS. In order to block non-specific binding sites, 100 μl of 0.5% BSA (Sigma) in PBS was then added to each well, and the plates were incubated for 2 hours at room temperature. The blocking solution was decanted, and 100 μl volumes of the IgY preparations described above were initially diluted 1:500 with a solution of 0.1% BSA in PBS, and then serially diluted in 1:5 steps. The following dilutions were placed in the wells: 1:500, 1:2,500, 1:62,5000, 1:312,500, and 1:1,562,500. The plates were again incubated for 2 hours at room temperature. Following this incubation, the IgY-containing solutions were decanted, and the wells were washed three times using BBS-Tween (0.1M boric acid, 0.025M sodium borate, 1.0M NaCl, 0.1% Tween-20), followed by two washes using PBS-Tween (0.1% Tween-20), and finally, two washes using PBS only. To each well, 100 μl of a 1:750 dilution of rabbit anti-chicken IgG (whole-molecule)-alkaline phosphatase conjugate (Sigma) (diluted in 0.1% BSA in PBS) was added. The plates were again incubated for 2 hours at room temperature. The conjugate solutions were decanted and the plates were washed as described above, substituting 50 mM $Na_2CO_3$, pH 9.5 for the PBS in the final wash. The plates were developed by the addition of 100 μl of a solution containing 1 mg/ml para-nitrophenyl phosphate (Sigma) dissolved in 50 mM $Na_2CO_3$, 10 mM $MgCl_2$, pH 9.5 to each well, and incubating the plates at room temperature in the dark for 45 minutes. The absorbance of each well was measured at 410 nm using a Dynatech MR 700 plate reader. In this manner, each of the four IgY preparations described above was tested for reactivity against both of the immunizing C. difficile strains; strain-specific, as well as cross-reactive activity was determined.

TABLE 5

Results Of The Anti-C. difficile Whole-Organism ELISA

| IgY PREPARATION | DILUTION OF IgY PREP | 43594-COATED WELLS | 43596-COATED WELLS |
|---|---|---|---|
| CD 43594, #1 | 1:500 | 1.746 | 1.801 |
| | 1:2,500 | 1.092 | 1.670 |
| | 1:12,500 | 0.202 | 0.812 |
| | 1:62,500 | 0.136 | 0.179 |
| | 1:312,500 | 0.012 | 0.080 |
| | 1:1,562,500 | 0.002 | 0.020 |
| CD 43594, #7 | 1:500 | 1.780 | 1.771 |
| | 1:2,500 | 1.025 | 1.078 |
| | 1:12,500 | 0.188 | 0.382 |
| | 1:62,500 | 0.052 | 0.132 |
| | 1:312,500 | 0.022 | 0.043 |
| | 1:1,562,500 | 0.005 | 0.024 |
| CD 43596, #1 | 1:500 | 1.526 | 1.790 |
| | 1:2,500 | 0.832 | 1.477 |
| | 1:12,500 | 0.247 | 0.452 |
| | 1:62,500 | 0.050 | 0.242 |
| | 1:312,500 | 0.010 | 0.067 |
| | 1:1,562,500 | 0.000 | 0.036 |
| CD 43596, #7 | 1:500 | 1.702 | 1.505 |

TABLE 5-continued

Results Of The Anti-C. difficile Whole-Organism ELISA

| IgY PREPARATION | DILUTION OF IgY PREP | 43594-COATED WELLS | 43596-COATED WELLS |
|---|---|---|---|
| | 1:2,500 | 0.706 | 0.866 |
| | 1:12,500 | 0.250 | 0.282 |
| | 1:62,500 | 0.039 | 0.078 |
| | 1:312,500 | 0.002 | 0.017 |
| | 1:1,562,500 | 0.000 | 0.010 |
| Preimmune IgY | 1:500 | 0.142 | 0.309 |
| | 1:2,500 | 0.032 | 0.077 |
| | 1:12,500 | 0.006 | 0.024 |
| | 1:62,500 | 0.002 | 0.012 |
| | 1:312,500 | 0.004 | 0.010 |
| | 1:1,562,500 | 0.002 | 0.014 |

Table 5 shows the results of the whole-organism ELISA. All four IgY preparations demonstrated significant levels of activity, to a dilution of 1:62,500 or greater against both of the immunizing organism strains. Therefore, antibodies raised against one strain were highly cross-reactive with the other strain, and vice versa. The immunizing concentration of organisms did not have a significant effect on organism-specific IgY production, as both concentrations produced approximately equivalent responses. Therefore, the lower immunizing concentration of approximately $1.5 \times 10^8$ organisms/hen is the preferred immunizing concentration of the two tested. The preimmune IgY preparation appeared to possess relatively low levels of C. difficile-reactive activity to a dilution of 1:500, probably due to prior exposure of the animals to environmental clostridia.

An initial whole-organism ELISA was performed using IgY preparations made from single CD 43594, #1 and CD 43596, #1 eggs collected around day 50 (data not shown). Specific titers were found to be 5 to 10-fold lower than those reported in Table 5. These results demonstrate that it is possible to begin immunizing hens prior to the time that they begin to lay eggs, and to obtain high titer specific IgY from the first eggs that are laid. In other words, it is not necessary to wait for the hens to begin laying before the immunization schedule is started.

EXAMPLE 2

Treatment Of C. difficile Infection With Anti-C. difficile Antibody

In order to determine whether the immune IgY antibodies raised against whole C. difficile organisms were capable of inhibiting the infection of hamsters by C. difficile, hamsters infected by these bacteria were utilized. [Lyerly et al., Infect. Immun., 59:2215–2218 (1991).] This example involved: (a) determination of the lethal dose of C. difficile organisms; and (b) treatment of infected animals with immune antibody or control antibody in nutritional solution.

(a) Determination of The Lethal Dose of C. difficile Organisms. Determination of the lethal dose of C. difficile organisms was carried out according to the model described by D. M. Lyerly et al., Infect. Immun., 59:2215–2218 (1991). C. difficile strain ATCC 43596 (serogroup C, ATCC) was plated on BHI agar and grown anaerobically (BBL Gas Pak 100 system) at 37° C. for 42 hours. Organisms were removed from the agar surface using a sterile dacron-tip swab and suspended in sterile 0.9% NaCl solution to a density of $10^8$ organisms/ml.

In order to determine the lethal dose of C. difficile in the presence of control antibody and nutritional formula, non-immune eggs were obtained from unimmunized hens and a 12% PEG preparation made as described in Example 1(c). This preparation was redissolved in one-fourth the original yolk volume of vanilla flavor Ensure®.

Starting on day one, groups of female Golden Syrian hamsters (Harlan Sprague Dawley), 8–9 weeks old and weighing approximately 100 gm, were orally administered 1 ml of the preimmune/Ensure® formula at time zero, 2 hours, 6 hours, and 10 hours. At 1 hour, animals were orally administered 3.0 mg clindamycin HCl (Sigma) in 1 ml of water. This drug predisposes hamsters to C. difficile infection by altering the normal intestinal flora. On day two, the animals were given 1 ml of the preimmune IgY/Ensure® formula at time zero, 2 hours, 6 hours, and 10 hours. At 1 hour on day two, different groups of animals were inoculated orally with saline (control), or $10^2$, $10^4$, $10^6$, or $10^8$ C. difficile organisms in 1 ml of saline. From days 3–12, animals were given 1 ml of the preimmune IgY/Ensure® formula three times daily and observed for the onset of diarrhea and death. Each animal was housed in an individual cage and was offered food and water ad libitum.

Administration of $10^6$–$10^8$ organisms resulted in death in 3–4 days while the lower doses of $10^2$–$10^4$ organisms caused death in 5 days. Cecal swabs taken from dead animals indicated the presence of C. difficile. Given the effectiveness of the $10^2$ dose, this number of organisms was chosen for the following experiment to see if hyperimmune anti-C. difficile antibody could block infection.

(b) Treatment of Infected Animals With Immune Antibody Or Control Antibody In Nutritional Formula. The experiment in (a) was repeated using three groups of seven hamsters each. Group A received no clindamycin or C. difficile and was the survival control. Group B received clindamycin, $10^2$ C. difficile organisms and preimmune IgY on the same schedule as the animals in (a) above. Group C received clindamycin, $10^2$ C. difficile organisms, and hyperimmune anti-C. difficile IgY on the same schedule as Group B. The anti-C. difficile IgY was prepared as described in Example 1 except that the 12% PEG preparation was dissolved in one-fourth the original yolk volume of Ensure®.

All animals were observed for the onset of diarrhea or other disease symptoms and death. Each animal was housed in an individual cage and was offered food and water ad libitum. The results are shown in Table 6.

Hamsters in the control group A did not develop diarrhea and remained healthy during the experimental period. Hamsters in groups B and C developed diarrheal disease. Anti-C. difficile IgY did not protect the animals from diarrhea or death, all animals succumbed in the same time interval as the animals treated with preimmune IgY. Thus, while immunization with whole organisms apparently can improve sublethal symptoms with particular bacteria (see U.S. Pat. No. 5,080,895 to H. Tokoro), such an approach does not prove to be productive to protect against the lethal effects of C. difficile.

TABLE 6

The Effect of Oral Feeding Of Hyperimmune IgY Antibody on C. difficile Infection

| ANIMAL GROUP | TIME TO DIARRHEA[a] | TIME TO DEATH[a] |
| --- | --- | --- |
| A pre-immune IgY only | no diarrhea | no deaths |
| B Clindamycin, C. difficile, preimmune IgY | 30 hrs. | 49 hrs. |
| C Clindamycin, C. difficile, immune IgY | 33 hrs. | 56 hrs. |

[a]mean of seven animals.

EXAMPLE 3

Production Of C. botulinum Type A Antitoxin in Hens

In order to determine whether antibodies could be raised against the toxin produced by clostridial pathogens, which would be effective in treating clostridial diseases, antitoxin to C. botulinum type A toxin was produced. This example involves: (a) toxin modification; (b) immunization; (c) antitoxin collection; (d) antigenicity assessment; and (e) assay of antitoxin titer.

(a) Toxin Modification. C. botulinum type A toxoid was obtained from B. R. DasGupta. From this, the active type A neurotoxin (M.W. approximately 150 kD) was purified to greater than 99% purity, according to published methods. [B. R. DasGupta & V. Sathyamoorthy, Toxicon, 22:415 (1984).] The neurotoxin was detoxified with formaldehyde according to published methods. [B. R. Singh & B. R. DasGupta, Toxicon, 27:403 (1989).]

(b) Immunization. C. botulinum toxoid for immunization was dissolved in PBS (1 mg/ml) and was emulsified with an approximately equal volume of CFA (GIBCO) for initial immunization or IFA for booster immunization. On day zero, two white leghorn hens, obtained from local breeders, were each injected at multiple sites (intramuscular and subcutaneous) with 1 ml inactivated toxoid emulsified in 1 ml CFA. Subsequent booster immunizations were made according to the following schedule for day of injection and toxoid amount: days 14 and 21–0.5 mg; day 171–0.75 mg; days 394, 401, 409–0.25 mg. One hen received an additional booster of 0.150 mg on day 544.

(c) Antitoxin Collection. Total yolk immunoglobulin (IgY) was extracted as described in Example 1(c) and the IgY pellet was dissolved in the original yolk volume of PBS with thimerosal.

(d) Antigenicity Assessment. Eggs were collected from day 409 through day 423 to assess whether the toxoid was sufficiently immunogenic to raise antibody. Eggs from the two hens were pooled and antibody was collected as described in the standard PEG protocol. [Example 1(c).] Antigenicity of the botulinal toxin was assessed on Western blots. The 150 kD detoxified type A neurotoxin and unmodified, toxic, 300 kD botulinal type A complex (toxin used for intragastric route administration for animal gut neutralization experiments; see Example 6) were separated on a SDS-polyacrylamide reducing gel. The Western blot technique was performed according to the method of Towbin. [H. Towbin et al., Proc. Nat'l Acad. Sci. U.S.A., 76:4350 (1979).] Ten μg samples of C. botulinum complex and toxoid were dissolved in SDS reducing sample buffer (1% SDS, 0.5% 2-mercaptoethanol, 50 mM Tris, pH 6.8, 10% glycerol, 0.025% w/v bromphenol blue, 10% β-mercaptoethanol), heated at 95° C. for 10 min and separated on a 1 mm thick 5% SDS-polyacrylamide gel. [K. Weber and M. Osborn,"Proteins and Sodium Dodecyl Sulfate: Molecular Weight Determination on Polyacrylamide Gels and Related Procedures," in The Proteins. 3d Edition (H. Neurath & R. L. Hill, eds), pp. 179–223, (Academic Press, NY, 1975).] Part of the gel was cut off and the proteins were stained with Coomassie Blue. The proteins in the remainder of the gel were transferred to nitrocellulose using the Milliblot-SDE electro-blotting system (Millipore) according to manufacturer's directions. The nitrocellulose was temporarily stained with 10% Ponceau S [S. B. Carroll and A. Laughon, "Production and Purification of Polyclonal Antibodies to the Foreign Segment of β-galactosidase Fusion Proteins," in DNA Cloning: A Practical Approach, Vol.III, (D. Glover, ed.), pp. 89–111, IRL Press, Oxford, (1987)] to visualize the lanes, then destained by running a gentle stream of distilled water over the blot for several minutes. The nitrocellulose was immersed in PBS containing 3% BSA overnight at 4° C. to block any remaining protein binding sites.

The blot was cut into strips and each strip was incubated with the appropriate primary antibody. The avian anti-C. botulinum antibodies [described in (c)] and preimmune chicken antibody (as control) were diluted 1:125 in PBS containing 1 mg/ml BSA for 2 hours at room temperature. The blots were washed with two changes each of large volumes of PBS, BBS-Tween and PBS, successively (10 min/wash). Goat anti-chicken IgG alkaline phosphatase conjugated secondary antibody (Fisher Biotech) was diluted 1:500 in PBS containing 1 mg/ml BSA and incubated with the blot for 2 hours at room temperature. The blots were washed with two changes each of large volumes of PBS and BBS-Tween, followed by one change of PBS and 0.1M Tris-HCl, pH 9.5. Blots were developed in freshly prepared alkaline phosphatase substrate buffer (100 μg/ml nitroblue tetrazolium (Sigma), 50 μg/ml 5-bromo-4-chloro-3-indolyl phosphate (Sigma), 5 mM $MgCl_2$ in 50 mM $Na_2CO_3$, pH 9.5).

The Western blots are shown in FIG. 1. The anti-C. botulinum IgY reacted to the toxoid to give a broad immunoreactive band at about 145–150 kD on the reducing gel. This toxoid is refractive to disulfide cleavage by reducing agents due to formalin crosslinking. The immune IgY reacted with the active toxin complex, a 97 kD C. botulinum type A heavy chain and a 53 kD light chain. The preimmune IgY was unreactive to the C. botulinum complex or toxoid in the Western blot.

(e) Antitoxin Antibody Titer. The IgY antibody titer to C. botulinum type A toxoid of eggs harvested between day 409 and 423 evaluated by ELISA, was prepared as follows. Ninety-six-well Falcon Pro-bind plates were coated overnight at 4° C. with 100 μl/well toxoid [B. R. Singh & B. R. Das Gupta, Toxicon 27:403 (1989)] at 2.5 μg/ml in PBS, pH 7.5 containing 0.005% thimerosal. The following day the wells were blocked with PBS containing 1% BSA for 1 hour at 37° C. The IgY from immune or preimmune eggs was diluted in PBS containing 1% BSA and 0.050% Tween 20 and the plates were incubated for 1 hour at 37° C. The plates were washed three times with PBS containing 0.05% Tween 20 and three times with PBS alone. Alkaline phosphatase-conjugated goat-anti-chicken IgG (Fisher Biotech) was diluted 1:750 in PBS containing 1% BSA and 0.05% Tween 20, added to the plates, and incubated 1 hour at 37° C. The plates were washed as before, and p-nitrophenyl phosphate (Sigma) at 1 mg/ml in 0.05M $Na_2CO_3$, pH 9.5, 10 mM $MgCl_2$ was added.

Figure 2:
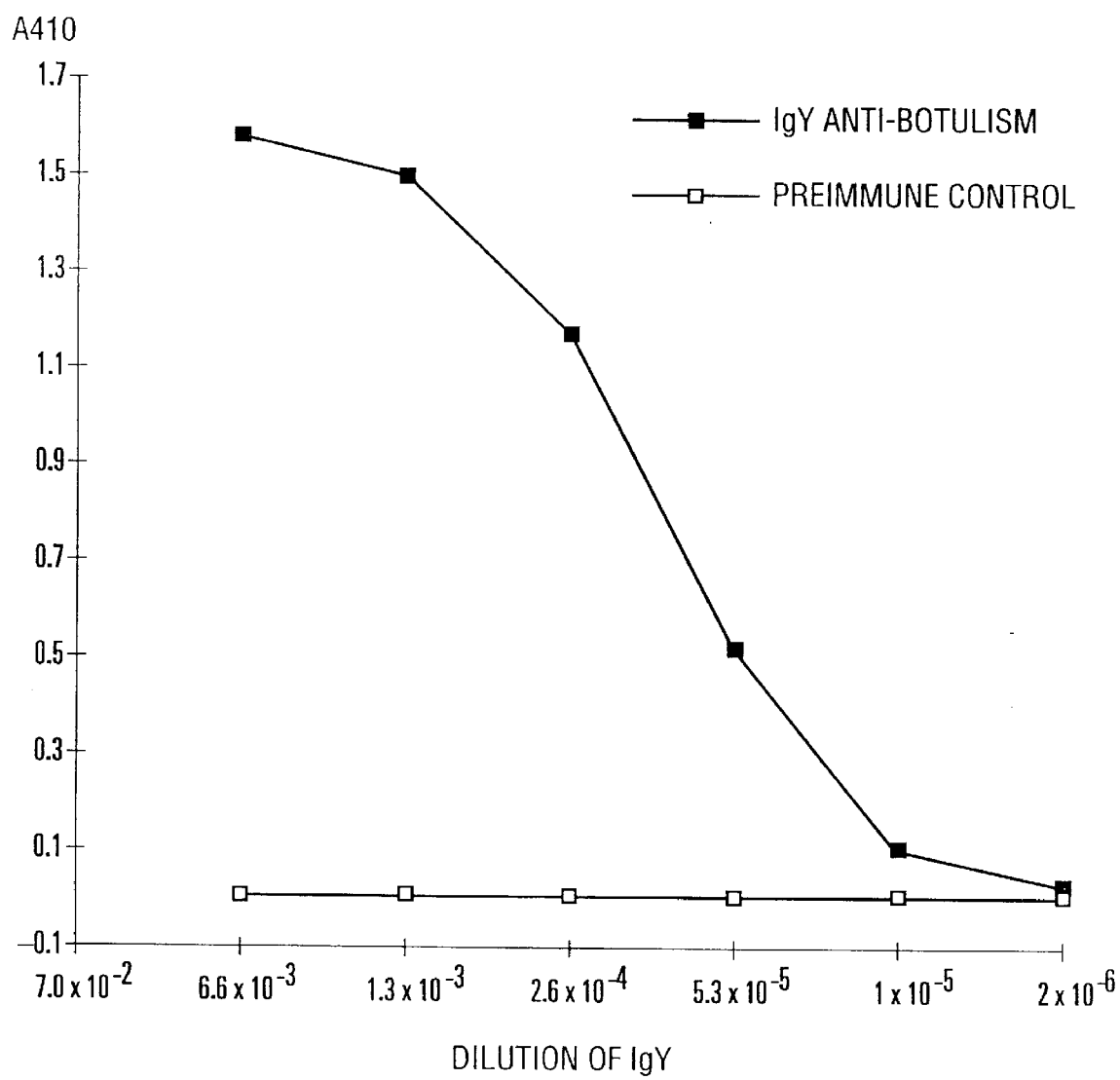
FIG. 2 shows the IgY antibody titer to C. botulinum type A toxoid in eggs, measured by ELISA.

The results are shown in FIG. 2. Chickens immunized with the toxoid generated high titers of antibody to the immunogen. Importantly, eggs from both immunized hens had significant anti-immunogen antibody titers as compared to preimmune control eggs. The anti-C. botulinum IgY possessed significant activity, to a dilution of 1:93,750 or greater.

EXAMPLE 4

Preparation Of Avian Egg Yolk Immunoglobulin In An Orally Administrable Form In order to administer avian IgY antibodies orally to experimental mice, an effective delivery formula for the IgY had to be determined. The concern was that if the crude IgY was dissolved in PBS, the saline in PBS would dehydrate the mice, which might prove harmful over the duration of the study. Therefore, alternative methods of oral administration of IgY were tested. The example involved: (a) isolation of immune IgY; (b) solubilization of IgY in water or PBS, including subsequent dialysis of the IgY-PBS solution with water to eliminate or reduce the salts (salt and phosphate) in the buffer; and (c) comparison of the quantity and activity of recovered IgY by absorbance at 280 nm and PAGE, and enzyme-linked immunoassay (ELISA).

(a) Isolation of Immune IgY. In order to investigate the most effective delivery formula for IgY, we used IgY which was raised against Crotalus durissus terrificus venom. Three eggs were collected from hens immunized with the C. durissus terrificus venom and IgY was extracted from the yolks using the modified Polson procedure described by Thalley and Carroll [Bio/Technology, 8:934–938 (1990)] as described in Example 1(c).

The egg yolks were separated from the whites, pooled, and blended with four volumes of PBS. Powdered PEG 8000 was added to a concentration of 3.5%. The mixture was centrifuged at 10,000 rpm for 10 minutes to pellet the precipitated protein, and the supernatant was filtered through cheesecloth to remove the lipid layer. Powdered PEG 8000 was added to the supernatant to bring the final PEG concentration to 12% (assuming a PEG concentration of 3.5% in the supernatant). The 12% PEG/IgY mixture was divided into two equal volumes and centrifuged to pellet the IgY.

(b) Solubilization of The IgY In Water Or PBS. One pellet was resuspended in ½ the original yolk volume of PBS, and the other pellet was resuspended in ½ the original yolk volume of water. The pellets were then centrifuged to remove any particles or insoluble material. The IgY in PBS solution dissolved readily but the fraction resuspended in water remained cloudy.

In order to satisfy anticipated sterility requirements for orally administered antibodies, the antibody solution needs to be filter-sterilized (as an alternative to heat sterilization which would destroy the antibodies). The preparation of IgY resuspended in water was too cloudy to pass through either a 0.2 or 0.45 µm membrane filter, so 10 ml of the PBS resuspended fraction was dialyzed overnight at room temperature against 250 ml of water. The following morning the dialysis chamber was emptied and refilled with 250 ml of fresh $H_2O$ for a second dialysis. Thereafter, the yields of soluble antibody were determined at $OD_{280}$ and are compared in Table 7.

TABLE 7

Dependence Of IgY Yield On Solvents

| FRACTION | ABSORBANCE OF 1:10 DILUTION AT 280 nm | PERCENT RECOVERY |
|---|---|---|
| PBS dissolved | 1.149 | 100% |
| $H_2O$ dissolved | 0.706 | 61% |
| PBS dissolved/$H_2O$ dialyzed | 0.885 | 77% |

Resuspending the pellets in PBS followed by dialysis against water recovered more antibody than directly resuspending the pellets in water (77% versus 61%). Equivalent volumes of the IgY preparation in PBS or water were compared by PAGE, and these results were in accordance with the absorbance values (data not shown).

(c) Activity of IgY Prepared With Different Solvents. An ELISA was performed to compare the binding activity of the IgY extracted by each procedure described above. C. durissus terrificus (C.d.t) venom at 2.5 µg/ml in PBS was used to coat each well of a 96-well microtiter plate. The remaining protein binding sites were blocked with PBS containing 5 mg/ml BSA. Primary antibody dilutions (in PBS containing 1 mg/ml BSA) were added in duplicate. After 2 hours of incubation at room temperature, the unbound primary antibodies were removed by washing the wells with PBS, BBS-Tween, and PBS. The species specific secondary antibody (goat anti-chicken immunoglobulin alkaline-phosphatase conjugate (Sigma) was diluted 1:750 in PBS containing 1 mg/ml BSA and added to each well of the microtiter plate. After 2 hours of incubation at room temperature, the unbound secondary antibody was removed by washing the plate as before, and freshly prepared alkaine phosphatase substrate (Sigma) at 1 mg/ml in 50 mM $Na_2CO_3$, 10 mM $MgCl_2$, pH 9.5 was added to each well. The color development was measured on a Dynatech MR 700 microplate reader using a 412 nm filter. The results are shown in Table 8.

The binding assay results parallel the recovery values in Table 7, with PBS-dissolved IgY showing slightly more activity than the PBS-dissolved/$H_2O$ dialyzed antibody. The water-dissolved antibody had considerably less binding activity than the other preparations.

EXAMPLE 5

Survival Of Antibody Activity After Passage Through The Gastrointestinal Tract In order to determine the feasibility of oral administration of antibody, it was of interest to determine whether orally administered IgY survived passage through the gastrointestinal tract. The example involved: (a) oral administration of specific immune antibody mixed with a nutritional formula; and (b) assay of antibody activity extracted from feces.

TABLE 8

Antigen-Binding Activity of IgY Prepared with Different Solvents

| DILUTION | PREIMMUNE | PBS DISSOLVED | $H_2O$ DISSOLVED | PBS/$H_2O$ |
|---|---|---|---|---|
| 1:500 | 0.005 | 1.748 | 1.577 | 1.742 |
| 1:2,500 | 0.004 | 0.644 | 0.349 | 0.606 |
| 1:12,500 | 0.001 | 0.144 | 0.054 | 0.090 |
| 1:62,500 | 0.001 | 0.025 | 0.007 | 0.016 |
| 1:312,500 | 0.010 | 0.000 | 0.000 | 0.002 |

(a) Oral Administration of Antibody. The IgY preparations used in this example are the same PBS-dissolved/$H_2O$ dialyzed antivenom materials obtained in Example 4 above, mixed with an equal volume of Enfamil®. Two mice were used in this experiment, each receiving a different diet as follows:

1) water and food as usual;

2) immune IgY preparation dialyzed against water and mixed 1:1 with Enfamil®. (The mice were given the corresponding mixture as their only source of food and water).

(b) Antibody Activity After Ingestion. After both mice had ingested their respective fluids, each tube was refilled with approximately 10 ml of the appropriate fluid first thing in the morning. By mid-morning there was about 4 to 5 ml of liquid left in each tube. At this point stool samples were collected from each mouse, weighed, and dissolved in approximately 500 µl PBS per 100 mg stool sample. One hundred and sixty mg of control stools (no antibody) and 99 mg of experimental stools (specific antibody) in 1.5 ml microfuge tubes were dissolved in 800 and 500 µl PBS, respectively. The samples were heated at 37° C. for 10 minutes and vortexed vigorously. The experimental stools were also broken up with a narrow spatula. Each sample was centrifuged for 5 minutes in a microfuge and the supernatants, presumably containing the antibody extracts, were collected. The pellets were saved at 2°–8° C. in case future extracts were needed. Because the supernatants were tinted, they were diluted five-fold in PBS containing 1 mg/ml BSA for the initial dilution in the enzyme immunoassay (ELISA). The primary extracts were then diluted five-fold serially from this initial dilution. The volume of primary extract added to each well was 190 µl. The ELISA was performed exactly as described in Example 4.

TABLE 9

Specific Antibody Activity After Passage Through the Gastrointestinal Tract

| DILUTION | PREIMMUNE IgY | CONTROL FECAL EXTRACT | EXP. FECAL EXTRACT |
|---|---|---|---|
| 1:5 | <0 | 0.000 | 0.032 |
| 1:25 | 0.016 | <0 | 0.016 |
| 1:125 | <0 | <0 | 0.009 |
| 1:625 | <0 | 0.003 | 0.001 |
| 1:3125 | <0 | <0 | 0.000 |

There was some active antibody in the fecal extract from the mouse given the specific antibody in Enfamil® formula, but it was present at a very low level. Since the samples were assayed at an initial 1:5 dilution, the binding observed could have been higher with less dilute samples. Consequently, the mice were allowed to continue ingesting either regular food and water or the specific IgY in Enfamil® formula, as appropriate, so the assay could be repeated. Another ELISA plate was coated overnight with 5 µg/ml of C.d.t. venom in PBS.

The following morning the ELISA plate was blocked with 5 mg/ml BSA, and the fecal samples were extracted as before, except that instead of heating the extracts at 37° C., the samples were kept on ice to limit proteolysis. The samples were assayed undiluted initially, and in 5× serial dilutions thereafter. Otherwise the assay was carried out as before.

TABLE 10

Specific Antibody Survives Passage Through The Gastrointestinal Tract

| DILUTION | PREIMMUNE IgY | CONTROL EXTRACT | EXP. EXTRACT |
|---|---|---|---|
| indiluted | 0.003 | <0 | 0.379 |
| 1:5 | <0 | <0 | 0.071 |
| 1:25 | 0.000 | <0 | 0.027 |
| 1:125 | 0.003 | <0 | 0.017 |
| 1:625 | 0.000 | <0 | 0.008 |
| 1:3125 | 0.002 | <0 | 0.002 |

The experiment confirmed the previous results, with the antibody activity markedly higher. The control fecal extract showed no anti-C.d.t. activity, even undiluted, while the fecal extract from the anti-C.d.t. IgY/Enfamil®-fed mouse showed considerable anti-C.d.t. activity. This experiment (and the previous experiment) clearly demonstrate that active IgY antibody survives passage through the mouse digestive tract, a finding with favorable implications for the success of IgY antibodies administered orally as a therapeutic or prophylactic.

EXAMPLE 6

In Vivo Neutralization of C. botulinum Type A Neurotoxin By Avian Antitoxin Antibody This example demonstrated the ability of PEG-purified antitoxin, collected as described in Example 3, to neutralize the lethal effect of C. botulinum neurotoxin type A in mice. To determine the oral lethal dose ($LD_{100}$) of toxin A, groups of BALB/c mice were given different doses of toxin per unit body weight (average body weight of 24 grams). For oral administration, toxin A complex, which contains the neurotoxin associated with other non-toxin proteins was used. This complex is markedly more toxic than purified neurotoxin when given by the oral route. [I. Ohishi et al., Infect. Immun., 16:106 (1977).] C. botulinum toxin type A complex, obtained from Eric Johnson (University of Wisconsin, Madison) was 250 µg/ml in 50 mM sodium citrate, pH 5.5, specific toxicity $3 \times 10^7$ mouse $LD_{50}$/mg with parenteral administration. Approximately 40–50 ng/gm body weight was usually fatal within 48 hours in mice maintained on conventional food and water. When mice were given a diet ad libitum of only Enfamil® concentration needed to produce lethality was approximately 2.5 times higher (125 ng/gm body weight). Botulinal toxin concentrations of approximately 200 ng/gm body weight were fatal in mice fed Enfamil® containing preimmune IgY (resuspended in Enfamil® at the original yolk volume).

The oral $LD_{100}$ of C. botulinum toxin was also determined in mice that received known amounts of a mixture of preimmune IgY-Ensure® delivered orally through feeding needles. Using a 22 gauge feeding needle, mice were given 250 µl each of a preimmune IgY-Ensure® mixture (preimmune IgY dissolved in ¼ original yolk volume) 1 hour before and ½ hour and 5 hours after administering botulinal toxin. Toxin concentrations given orally ranged from approximately 12 to 312 ng/gm body weight (0.3 to 7.5 µg per mouse). Botulinal toxin complex concentration of approximately 40 ng/gm body weight (1 µg per mouse) was lethal in all mice in less than 36 hours.

Two groups of BALB/c mice, 10 per group, were each given orally a single dose of 1 µg each of botulinal toxin complex in 100 µl of 50 mM sodium citrate pH 5.5. The mice received 250 µl treatments of a mixture of either preimmune or immune IgY in Ensure® (¼ original yolk volume) 1 hour before and ½ hour, 4 hours, and 8 hours after botulinal toxin administration. The mice received three treatments per day for two more days. The mice were observed for 96 hours. The survival and mortality are shown in Table 11.

TABLE 11

Neutralization of Botulinal Toxin A In Vivo

| TOXIN DOSE ng/gm | ANTIBODY TYPE | NUMBER OF MICE ALIVE | NUMBER OF MICE DEAD |
|---|---|---|---|
| 41.6 | non-immune | 0 | 10 |
| 41.6 | anti-botulinal toxin | 10 | 0 |

All mice treated with the preimmune IgY-Ensure® mixture died within 46 hours post-toxin administration. The average time of death in the mice was 32 hours post toxin administration. Treatments of preimmune IgY-Ensure® mixture did not continue beyond. 24 hours due to extensive paralysis of the mouth in mice of this group. In contrast, all ten mice treated with the immune anti-botulinal toxin IgY-Ensure® mixture survived past 96 hours. Only 4 mice in this group exhibited symptoms of botulism toxicity (two mice about 2 days after and two mice 4 days after toxin administration). These mice eventually died 5 and 6 days later. Six of the mice in this immune group displayed no adverse effects to the toxin and remained alive and healthy long term. Thus, the avian anti-botulinal toxin antibody demonstrated very good protection from the lethal effects of the toxin in the experimental mice.

EXAMPLE 7

Production Of An Avian Antitoxin Against *Clostridium difficile* Toxin A

Toxin A is a potent cytotoxin secreted by pathogenic strans of *C. difficile,* that plays a direct role in damaging gastrointestinal tissues. In more severe cases of *C. difficile* intoxication, pseudomembranous colitis can develop which may be fatal. This would be prevented by neutralizing the effects of this toxin in the gastrointestinal tract. As a first step, antibodies were produced against a portion of the toxin. The example involved: (a) conjugation of a synthetic peptide of toxin A to bovine serum albumin; (b) immunization of hens with the peptide-BSA conjugate; and (c) detection of antitoxin peptide antibodies by ELISA.

(a) Conjugation of a Synthetic Peptide of Toxin A to Bovine Serum Albumin. The synthetic peptide CQTIDGKKYYFN-$NH_2$ (SEQ ID NO:5) was prepared commercially (Multiple Peptide Systems, San Diego, Calif.) and validated to be >80% pure by high-pressure liquid chromatography. The eleven amino acids following the cysteine residue represent a consensus sequence of a repeated amino acid sequence found in Toxin A. [Wren et al., Infect. Immun., 59:3151–3155 (1991).] The cysteine was added to facilitate conjugation to carrier protein.

In order to prepare the carrier for conjugation, BSA (Sigma) was dissolved in 0.01M $NaPO_4$, pH 7.0 to a final concentration of 20 mg/ml and n-maleimidobenzoyl-N-hydroxysuccinimide ester (MBS; Pierce) was dissolved in N,N-dimethyl formamide to a concentration of 5 mg/ml. MBS solution, 0.51 ml, was added to 3.25 ml of the BSA solution and incubated for 30 minutes at room temperature with stirring every 5 minutes. The MBS-activated BSA was then purified by chromatography on a Bio-Gel P-10 column (Bio-Rad; 40 ml bed volume) equilibrated with 50 mM $NaPO_4$, pH 7.0 buffer. Peak fractions were pooled (6.0 ml).

Lyophilized toxin A peptide (20 mg) was added to the activated BSA mixture, stirred until the peptide dissolved and incubated 3 hours at room temperature. Within 20 minutes, the reaction mixture became cloudy and precipitates formed. After 3 hours, the reaction mixture was centrifuged at 10,000×g for 10 min and the supernatant analyzed for protein content. No significant protein could be detected at 280 nm. The conjugate precipitate was washed three times with PBS and stored at 4° C. A second conjugation was performed with 15 mg of activated BSA and 5 mg of peptide and the conjugates pooled and suspended at a peptide concentration of 10 mg/ml in 10 mM $NaPO_4$, pH 7.2.

(b) Immunization of Hens With Peptide Conjugate. Two hens were each initially immunized on day zero by injection into two subcutaneous and two intramuscular sites with 1 mg of peptide conjugate that was emulsified in CFA (GIBCO). The hens were boosted on day 14 and day 21 with 1 mg of peptide conjugate emulsified in IFA (GIBCO).

(c) Detection of Antitoxin Peptide Antibodies By ELISA. IgY was purified from two eggs obtained before immunization (pre-immune) and two eggs obtained 31 and 32 days after the initial immunization using PEG fractionation as described in Example 1.

Wells of a 96-well microtiter plate (Falcon Pro-Bind Assay Plate) were coated overnight at 4° C. with 100 μg/ml solution of the toxin A synthetic peptide in PBS, pH 7.2 prepared by dissolving 1 mg of the peptide in 1.0 ml of $H_2O$ and dilution of PBS. The pre-immune and immune IgY preparations were diluted in a five-fold series in a buffer containing 1% PEG 8000 and 0.1% Tween-20 (v/v) in PBS, pH 7.2. The wells were blocked for 2 hours at room temperature with 150 μl of a solution containing 5% (v/v) Carnation® nonfat dry milk and 1% PEG 8000 in PBS, pH 7.2. After incubation for 2 hours at room temperature, the wells were washed, secondary rabbit anti-chicken IgG-alkaline phosphatase (1:750) added, the wells washed again and the color development obtained as described in Example 1. The results are shown in Table 12.

TABLE 12

Reactivity Of IgY With Toxin Peptide

| | ABSORBANCE AT 410 nm | |
|---|---|---|
| DILUTION OF PEG PREP | PREIMMUNE | IMMUNE ANTI-PEPTIDE |
| 1:100 | 0.013 | 0.253 |
| 1:500 | 0.004 | 0.039 |
| 1:2500 | 0.004 | 0.005 |

Clearly, the immune antibodies contain titers against this repeated epitope of toxin A.

EXAMPLE 8

Production Of Avian Antitoxins Against *Clostridium difficile* Native Toxins A And B To determine whether avian antibodies are effective for the neutralization of *C. difficile* toxins, hens were immunized using native *C. difficile* toxins A and B. The resulting egg yolk antibodies were then extracted and assessed for their ability to neutralize toxins A and B in vitro. The Example involved (a) preparation of the toxin immunogens, (b)

immunization, (c) purification of the antitoxins, and (d) assay of toxin neutralization activity.

(a) Preparation Of The Toxin Immunogens. Both *C. difficile* native toxins A and B, and *C. difficile* toxoids, prepared by the treatment of the native toxins with formaldehyde, were employed as immunogens. *C. difficile* toxoids A and B were prepared by a procedure which was modified from published methods (Ehrich et al., Infect. Immun. 28:1041 (1980). Separate solutions (in PBS) of native *C. difficile* toxin A and toxin B (Tech Lab) were each adjusted to a concentration of 0.20 mg/ml, and formaldehyde was added to a final concentration of 0.4%. The toxin/formaldehyde solutions were then incubated at 37° C. for 40 hrs. Free formaldehyde was then removed from the resulting toxoid solutions by dialysis against PBS at 4° C. In previously published reports, this dialysis step was not performed. Therefore, free formaldehyde must have been present in their toxoid preparations. The toxoid solutions were concentrated, using a Centriprep concentrator unit (Amicon), to a final toxoid concentration of 4.0 mg/ml. The two resulting preparations were designated as toxoid A and toxoid B.

*C. difficile* native toxins were prepared by concentrating stock solutions of toxin A and toxin B (Tech Lab, Inc), using Centriprep concentrator units (Amicon), to a final concentration of 4.0 mg/ml.

(b) Immunization. The first two immunizations were performed using the toxoid A and toxoid B immunogens described above. A total of 3 different immunization combinations were employed. For the first immunization group, 0.2 ml of toxoid A was emulsified in an equal volume of Titer Max adjuvant (CytRx). Titer Max was used in order to conserve the amount of immunogen used, and to simplify the immunization procedure. This immunization group was designated "CTA." For the second immunization group, 0.1 ml of toxoid B was emulsified in an equal volume of Titer Max adjuvant. This group was designated "CTB." For the third immunization group, 0.2 ml of toxoid A was first mixed with 0.2 ml of toxoid B, and the resulting mixture was emulsified in 0.4 ml of Titer Max adjuvant. This group was designated "CTAB." In this way, three separate immunogen emulsions were prepared, with each emulsion containing a final concentration of 2.0 mg/ml of toxoid A (CTA) or toxoid B (CTB) or a mixture of 2.0 mg/ml toxoid A and 2.0 mg/ml toxoid B (CTAB).

On day 0, White Leghorn hens, obtained from a local breeder, were immunized as follows: Group CTA. Four hens were immunized, with each hen receiving 200 µg of toxoid A, via two intramuscular (I.M.) injections of 50 µl of CTA emulsion in the breast area. Group CTB. One hen was immunized with 200 µg of toxoid B, via two I.M. injections of 50 µl of CTB emulsion in the breast area. Group CTAB. Four hens were immunized, with each hen receiving a mixture containing 200 µg of toxoid A and 200 µg of toxoid B, via two I.M. injections of 100 µl of CTAB emulsion in the breast area. The second immunization was performed 5 weeks later, on day 35, exactly as described for the first immunization above.

In order to determine whether hens previously immunized with *C. difficile* toxoids could tolerate subsequent booster immunizations using native toxins, a single hen from group CTAB was immunized for a third time, this time using a mixture of the native toxin A and native toxin B described in section (a) above (these toxins were not formaldehyde-treated, and were used in their active form). This was done in order to increase the amount (titer) and affinity of specific antitoxin antibody produced by the hen over that achieved by immunizing with toxoids only. On day 62, 0.1 ml of a toxin mixture was prepared which contained 200 µg of native toxin A and 200 µg of native toxin B. This toxin mixture was then emulsified in 0.1 ml of Titer Max adjuvant A single CTAB hen was then immunized with the resulting immunogen emulsion, via two I.M. injections of 100 µl each, into the breast area This hen was marked with a wing band, and observed for adverse effects for a period of approximately 1 week, after which time the hen appeared to be in good health.

Because the CTAB hen described above tolerated the booster immunization with native toxins A and B with no adverse effects, it was decided to boost the remaining hens with native toxin as well. On day 70, booster immunizations were performed as follows: Group CTA. A 0.2 ml volume of the 4 mg/ml native toxin A solution was emulsified in an equal volume of Titer Max adjuvant. Each of the 4 hens was then immunized with 200 µg of native toxin A, as described for the toxoid A immunizations above. Group CTB. A 50 µl volume of the 4 mg/ml native toxin B solution was emulsified in an equal volume of Titer Max adjuvant. The hen was then immunized with 200 µg of native toxin B, as described for the toxoid B immunizations above. Group CTAB. A 0.15 ml volume of the 4 mg/ml native toxin A solution was first mixed with a 0.15 ml volume the 4 mg/ml native toxin B solution. The resulting toxin mixture was then emulsified in 0.3 ml of Titer Max adjuvant. The 3 remaining hens (the hen with the wing band was not immunized this time) were then immunized with 200 µg of native toxin A and 200 µg of native toxin B as described for the toxoid A+toxoid B immunizations (CTAB) above. On day 85, all hens received a second booster immunization using native toxins, done exactly as described for the first boost with native toxins above.

All hens tolerated both booster immunizations with native toxins with no adverse effects. As previous literature references describe the use of formaldehyde-treated toxoids, this is apparently the first time that any immunizations have been performed using native *C. difficile* toxins.

(c) Purification Of Antitoxins. Eggs were collected from the hen in group CTB 10–12 days following the second immunization with toxoid (day 35 immunization described in section (b) above), and from the hens in groups CTA and CTAB 20–21 days following the second immunization with toxoid. To be used as a pre-immune (negative) control, eggs were also collected from unimmunized hens from the same flock. Egg yolk immunoglobulin (IgY) was extracted from the 4 groups of eggs as described in Example 1 (c), and the final IgY pellets were solubilized in the original yolk volume of PBS without thimerosal. Importantly, thimerosal was excluded because it would have been toxic to the CHO cells used in the toxin neutralization assays described in section (d) below.

(d) Assay Of Toxin Neutralization Activity. The toxin neutralization activity of the IgY solutions prepared in section (c) above was determined using an assay system that was modified from published methods. [Ehrich et al., Infect. Immun. 28:1041–1043 (1992); and McGee et al. Microb. Path. 12:333–341 (1992).] As additional controls, affinity-purified goat anti-*C. difficile* toxin A (Tech Lab) and affinity-purified goat anti-*C. difficile* toxin B (Tech Lab) were also assayed for toxin neutralization activity.

The IgY solutions and goat antibodies were serially diluted using F 12 medium (GIBCO) which was supplemented with 2% FCS (GIBCO)(this solution will be referred to as "medium" for the remainder of this Example). The resulting antibody solutions were then mixed with a standardized concentration of either native *C. difficile* toxin A (Tech Lab), or native *C. difficile* toxin B (Tech Lab), at the concentrations indicated below. Following incubation at 37° C. for 60 min., 100 µl volumes of the toxin+antibody mixtures were added to the wells of 96-well microtiter plates (Falcon Microtest III) which contained $2.5 \times 10^4$ Chinese Hamster Ovary (CHO) cells per well (the CHO cells were plated on the previous day to allow them to adhere to the plate wells). The final concentration of toxin, or dilution of antibody indicated below refers to the final test concentration of each reagent present in the respective microtiter plate wells. Toxin reference wells were prepared which contained CHO cells and toxin A or toxin B at the same concentration used for the toxin+antibody mixtures (these wells contained no antibody). Separate control wells were also prepared which contained CHO cells and medium only. The assay plates were then incubated for 18–24 hrs. in a 37° C., humidified, 5% $CO_2$ incubator. On the following day, the remaining adherent (viable) cells in the plate wells were stained using 0.2% crystal violet (Mallinckrodt) dissolved in 2% ethanol, for 10 min. Excess stain was then removed by rinsing with water, and the stained cells were solubilized by adding 100 µl of 1% SDS (dissolved in water) to each well. The absorbance of each well was then measured at 570 nm, and the percent cytotoxicity of each test sample or mixture was calculated using the following formula:

$$\% \text{ CHO Cell Cytotoxicity} = \left[ 1 - \left( \frac{\text{Abs. Sample}}{\text{Abs. Control}} \right) \right] \times 100$$

Figure 3:
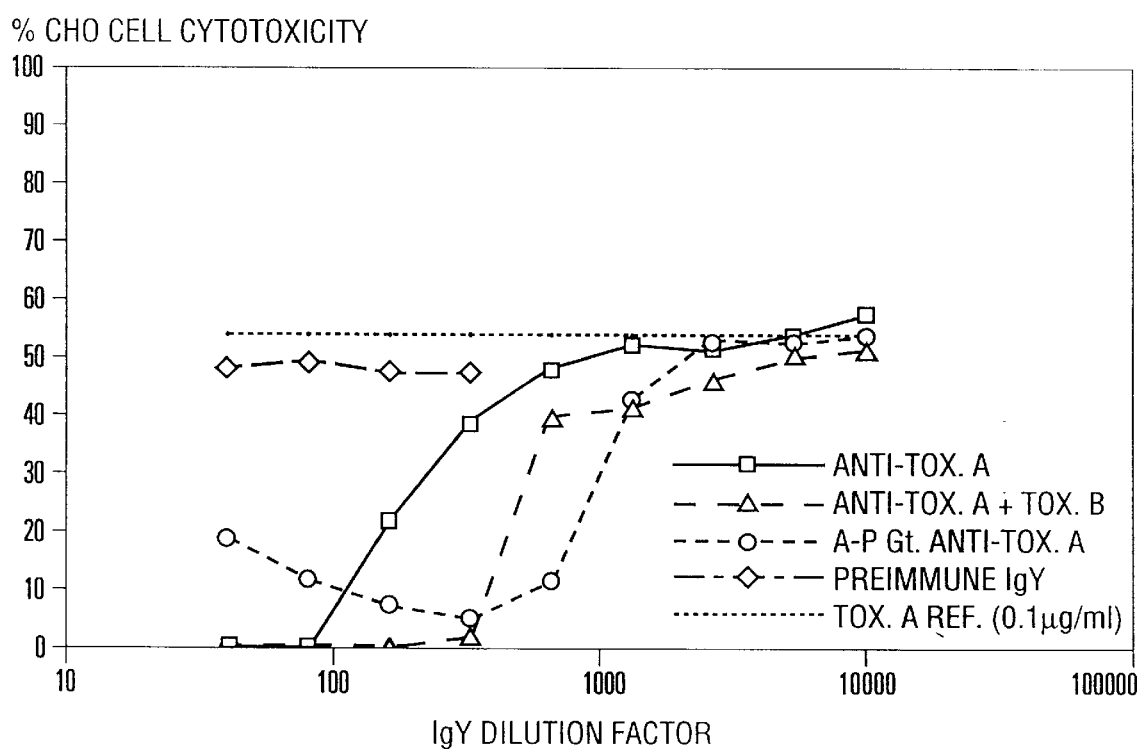
FIG. 3 shows the results of C. difficile toxin A neutralization assays.

Unlike previous reports which quantitate results visually by counting cell rounding by microscopy, this Example utilized spectrophotometric methods to quantitate the *C. difficile* toxin bioassay. In order to determine the toxin A neutralizing activity of the CTA, CTAB, and pre-immune IgY preparations, as well as the affinity-purified goat antitoxin A control, dilutions of these antibodies were reacted against a 0.1 µg/ml concentration of native toxin A (this is the approx. 50% cytotoxic dose of toxin A in this assay system). The results are shown in FIG. 3.

Complete neutralization of toxin A occurred with the CTA IgY (antitoxin A, above) at dilutions of 1:80 and lower, while significant neutralization occurred out to the 1:320 dilution. The CTAB IgY (antitoxin A+toxin B, above) demonstrated complete neutralization at the 1:320–1:160 and lower dilutions, and significant neutralization occurred out to the 1:1280 dilution. The commercially available affinity-purified goat antitoxin A did not completely neutralize toxin A at any of the dilutions tested, but demonstrated significant neutralization out to a dilution of 1:1,280. The preimmune IgY did not show any toxin A neutralizing activity at any of the concentrations tested. These results demonstrate that IgY purified from eggs laid by hens immunized with toxin A alone, or simultaneously with toxin A and toxin B, is an effective toxin A antitoxin.

Figure 4:
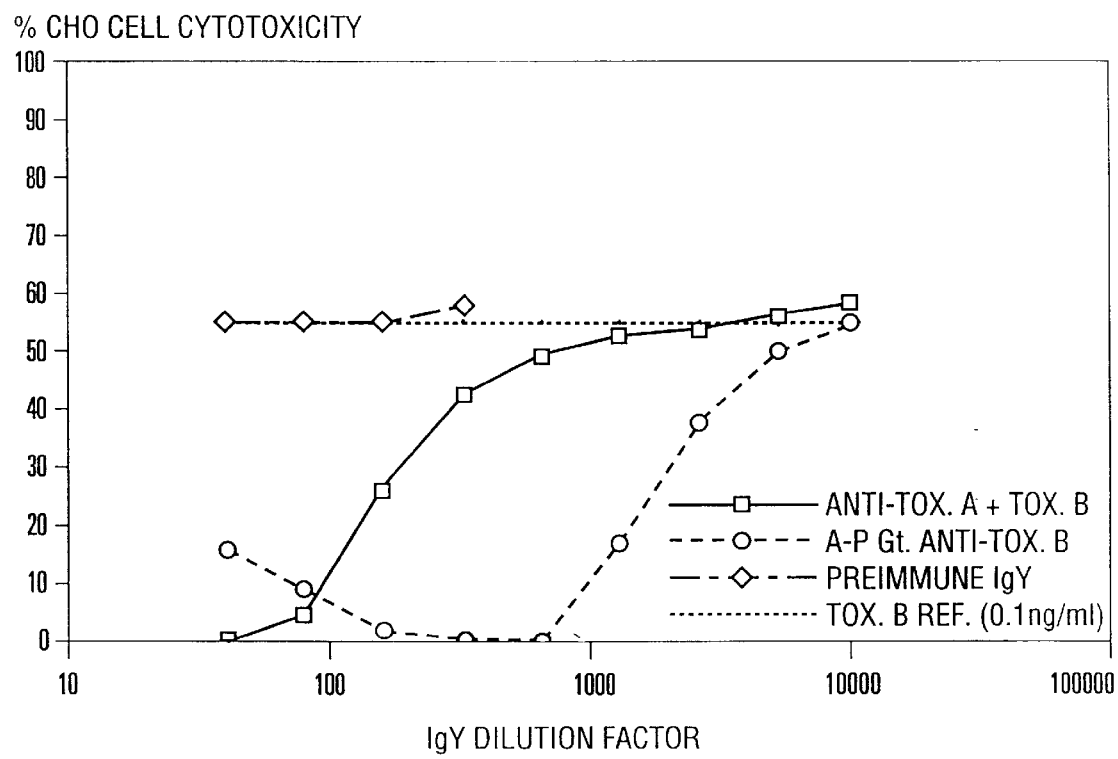
FIG. 4 shows the results of C. difficile toxin B neutralization assays.

The toxin B neutralizing activity of the CTAB and pre-immune IgY preparations, and also the affinity-purified goat antitoxin B control was determined by reacting dilutions of these antibodies against a concentration of native toxin B of 0.1 ng/ml (approximately the 50% cytotoxic dose of toxin B in the assay system). The results are shown in FIG. 4.

Complete neutralization of toxin B occurred with the CTAB IgY (antitoxin A+toxin B, above) at the 1:40 and lower dilutions, and significant neutralization occurred out to the 1:320 dilution. The affinity-purified goat antitoxin B demonstrated complete neutralization at dilutions of 1:640 and lower, and significant neutralization occurred out to a dilution of 1:2,560. The preimmune IgY did not show any toxin B neutralizing activity at any of the concentrations tested. These results demonstrate that IgY purified from eggs laid by hens immunized simultaneously with toxin A and toxin B is an effective toxin B antitoxin.

Figure 5:
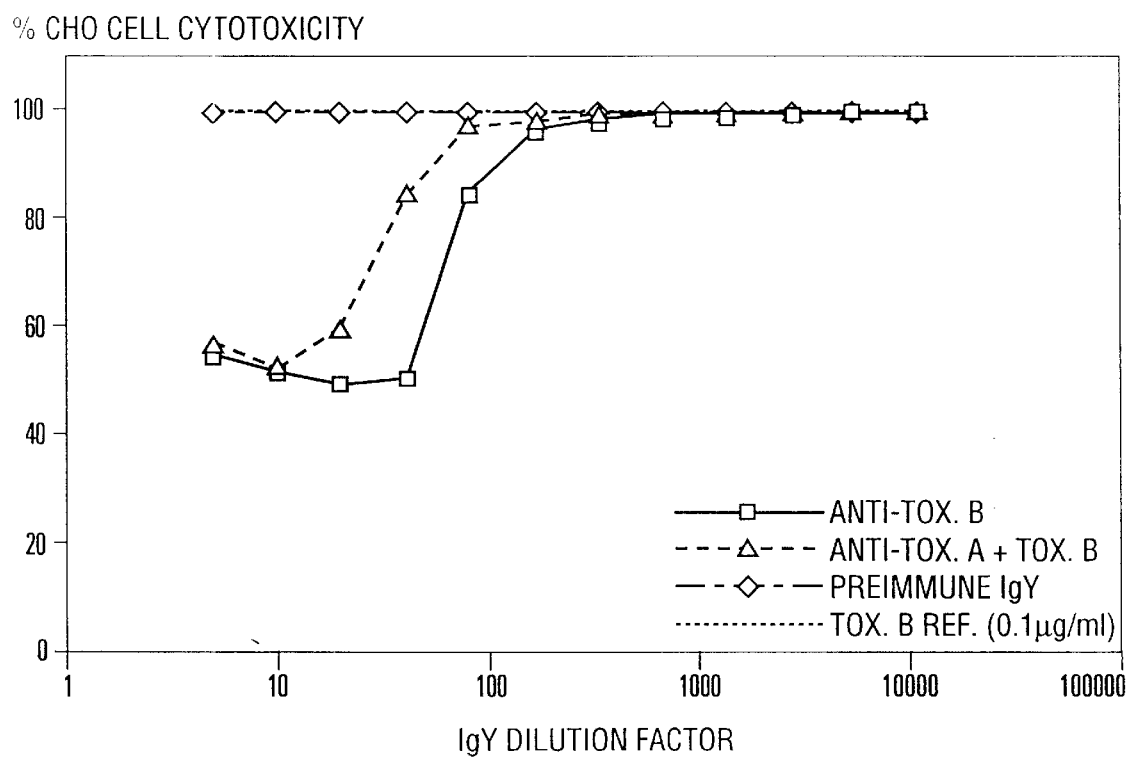
FIG. 5 shows the results of C. difficile toxin B neutralization assays.

In a separate study, the toxin B neutralizing activity of CTB, CTAB, and preimmune IgY preparations was determined by reacting dilutions of these antibodies against a native toxin B concentration of 0.1 µg/ml (approximately 100% cytotoxic dose of toxin B in this assay system). The results are shown in FIG. 5.

Significant neutralization of toxin B occurred with the CTB IgY (antitoxin B, above) at dilutions of 1:80 and lower, while the CTAB IgY (antitoxin A+toxin B, above) was found to have significant neutralizing activity at dilutions of 1:40 and lower. The preimmune IgY did not show any toxin B neutralizing activity at any of the concentrations tested. These results demonstrate that IgY purified from eggs laid by hens immunized with toxin B alone, or simultaneously with toxin A and toxin B, is an effective toxin B antitoxin.

EXAMPLE 9

In vivo Protection Of Golden Syrian Hamsters From *C. difficile* Disease By Avian Antitoxins Against *C. difficile* Toxins A And B The most extensively used animal model to study *C. difficile* disease is the hamster. [Lyerly et al., Infect. Immun. 47:349–352 (1992).] Several other animal models for antibiotic-induced diarrhea exist, but none mimic the human form of the disease as closely as the hamster model. [R. Fekety, "*Animal Models of Antibiotic-Induced Colitis,*" in O. Zak and M. Sande (eds.), *Experimental Models in Antimicrobial Chemothera*, Vol. 2, pp.61–72, (1986).] In this model, the animals are first predisposed to the disease by the oral administration of an antibiotic, such as clindamycin, which alters the population of normally-occurring gastrointestinal flora (Fekety, at 61–72). Following the oral challenge of these animals with viable *C. difficile* organisms, the hamsters develop cecitis, and hemorrhage, ulceration, and inflammation are evident in the intestinal mucosa. [Lyerly et al., Infect. Immun. 47:349–352 (1985).] The animals become lethargic, develop severe diarrhea, and a high percentage of them die from the disease. [Lyerly et al., Infect. Immun. 47:349–352 (1985).] This model is therefore ideally suited for the evaluation of therapeutic agents designed for the treatment or prophylaxis of *C. difficile* disease.

The ability of the avian *C. difficile* antitoxins, described in Example 8 above, to protect hamsters from *C. difficile* disease was evaluated using the Golden Syrian hamster model of *C. difficile* infection. The Example involved (a) preparation of the avian *C. difficile* antitoxins, (b) in vivo protection of hamsters from *C. difficile* disease by treatment with avian antitoxins, and (c) long-term survival of treated hamsters.

(a) Preparation Of The Avian *C. difficile* Antitoxins. Eggs were collected from hens in groups CTA and CTAB described in Example 8 (b) above. To be used as a preimmune (negative) control, eggs were also purchased from a local supermarket. Egg yolk immunoglobulin (IgY) was extracted from the 3 groups of eggs as described in Example 1 (c), and the fmal IgY pellets were solubilized in one-fourth the original yolk volume of Ensure® nutritional formula (b) In vivo Protection Of Hamsters Against *C. difficile* Disease By Treatment With Avian Antitoxins. The avian *C. difficile* antitoxins prepared in section (a) above were evaluated for their ability to protect hamsters from *C. difficile* disease using an animal model system which was modified from published procedures. [Fekety, at 61–72; Borriello et al., J. Med. Microbiol., 24:53–64 (1987); Kim et al., Infect. Immun., 55:2984–2992 (1987); Borriello et al., J. Med. Microbiol., 25:191–196 (1988); Delmee and Avesani, J. Med. Microbiol., 33:85–90 (1990); and Lyerly et al., Infect. Immun., 59:2215–2218 (1991).] For the study, three separate experimental groups were used, with each group consisting of 7 female Golden Syrian hamsters (Charles River), approximately 10 weeks old and weighing approximately 100 gms. each. The three groups were designated "CTA," "CTAB" and "Pre-immune." These designations corresponded to the antitoxin preparations with which the animals in each group were treated. Each animal was housed in an individual cage, and was offered food and water ad libitum through the entire length of the study. On day 1, each animal was orally administered 1.0 ml of one of the three antitoxin preparations (prepared in section (a) above) at the following timepoints: 0 hrs., 4 hrs., and 8 hrs. On day 2, the day 1 treatment was repeated. On day 3, at the 0 hr. timepoint, each animal was again administered antitoxin, as described above. At 1 hr., each animal was orally administered 3.0 mg of clindamycin-HCl (Sigma) in 1 ml of water. This treatment predisposed the animals to infection with *C. difficile*. As a control for possible endogenous *C. difficile* colonization, an additional animal from the same shipment (untreated) was also administered 3.0 mg of clindamycin-HCl in the same manner. This clindamycin control animal was left untreated (and uninfected) for the remainder of the study. At the 4 hr. and 8 hr. timepoints, the animals were administered antitoxin as described above. On day 4, at the 0 hr. timepoint, each animal was again administered antitoxin as described above. At 1 hr., each animal was orally challenged with 1 ml of *C. difficile* inoculum, which contained approx. 100 *C. difficile* strain 43596 organisms in sterile saline. *C. difficile* strain 43596, which is a serogroup C strain, was chosen because it is representative of one of the most frequently-occurring serogroups isolated from patients with antibiotic-associated pseudomembranous colitis. [Delmee et al., J. Clin. Microbiol., 28:2210–2214 (1985).] In addition, this strain has been previously demonstrated to be virulent in the hamster model of infection. [Delmee and Avesani, J. Med. Microbiol., 33:85–90 (1990).] At the 4 hr. and 8 hr. timepoints, the animals were administered antitoxin as described above. On days 5 through 13, the animals were administered antitoxin 3× per day as described for day 1 above, and observed for the onset of diarrhea and death. On the morning of day 14, the fmal results of the study were tabulated. These results are shown in Table 13.

Representative animals from those that died in the Pre-Immune and CTA groups were necropsied. Viable *C. difficile* organisms were cultured from the ceca of these animals, and the gross pathology of the gastrointestinal tracts of these animals was consistent with that expected for *C. difficile* disease (inflamed, distended, hemorrhagic cecum, filled with watery diarrhea-like material). In addition, the clindamycin control animal remained healthy throughout the entire study period, therefore indicating that the hamsters used in the study had not previously been colonized with endogenous *C. difficile* organisms prior to the start of the study. Following the final antitoxin treatment on day 13, a single surviving animal from the CTA group, and also from the CTAB group, was sacrificed and necropsied. No pathology was noted in either animal.

TABLE 13

| | Treatment Results | |
|---|---|---|
| Treatment Group | No. Animals Surviving | No. Animals Dead |
| Pre-Immune | 1 | 6 |
| CTA (Antitoxin A only) | 5 | 2 |
| CTAB (Antitoxin A + Antitoxin B) | 7 | 0 |

Treatment of hamsters with orally-administered toxin A and toxin B antitoxin (group CTAB) successfully protected 7 out of 7 (100%) of the animals from *C. difficile* disease. Treatment of hamsters with orally-administered toxin A antitoxin (group CTA) protected 5 out of 7 (71%) of these animals from *C. difficile* disease. Treatment using pre-immune IgY was not protective against *C. difficile* disease, as only 1 out of 7 (14%) of these animals survived. These results demonstrate that the avian toxin A antitoxin and the avian toxin A+toxin B antitoxin effectively protected the hamsters from *C. difficile* disease. These results also suggest that although the neutralization of toxin A alone confers some degree of protection against *C. difficile* disease, in order to achieve maximal protection, simultaneous antitoxin A and antitoxin B activity is necessary.

(c) Long-Term Survival Of Treated Hamsters. It has been previously reported in the literature that hamsters treated with orally-administered bovine antitoxin IgG concentrate are protected from *C. difficile* disease as long as the treatment is continued, but when the treatment is stopped, the animals develop diarrhea and subsequently die within 72 hrs. [Lyerly et al., Infect. Immun., 59(6):2215–2218 (1991).]

In order to determine whether treatment of *C. difficile* disease using avian antitoxins promotes long-term survival following the discontinuation of treatment, the 4 surviving animals in group CTA, and the 6 surviving animals in group CTAB were observed for a period of 11 days (264 hrs.) following the discontinuation of antitoxin treatment described in section (b) above. All hamsters remained healthy through the entire post-treatment period. This result demonstrates that not only does treatment with avian antitoxin protect against the onset of *C. difficile* disease (i.e., it is effective as a prophylactic), it also promotes long-term survival beyond the treatment period, and thus provides a lasting cure.

EXAMPLE 10

In vivo Treatment Of Established *C. difficile* Infection In Golden Syrian Hamsters With Avian Antitoxins Against *C. difficile* Toxins A And B The ability of the avian *C. difficile* antitoxins, described in Example 8 above, to treat an established *C. difficile* infection was evaluated using the Golden Syrian hamster model. The Example involved (a) preparation of the avian *C. difficile* antitoxins, (b) in vivo treatment of hamsters with established *C. difficile* infection, and (c) histologic evaluation of cecal tissue.

(a) Preparation Of The Avian *C. difficile* Antitoxins. Eggs were collected from hens in group CTAB described in Example 8 (b) above, which were immunized with *C. difficile* toxoids and native toxins A and B. Eggs purchased from a local supermarket were used as a pre-immune (negative) control. Egg yolk immunoglobulin (IgY) was extracted from the 2 groups of eggs as described in Example 1 (c), and the final IgY pellets were solubilized in one-fourth the original yolk volume of Ensure® nutritional formula.

(b) In vivo Treatment Of Hamsters With Established *C. difficile* Infection. The avian *C. difficile* antitoxins prepared in section (a) above were evaluated for the ability to treat established *C. difficile* infection in hamsters using an animal model system which was modified from the procedure which was described for the hamster protection study in Example 9(b) above.

For the study, four separate experimental groups were used, with each group consisting of 7 female Golden Syrian hamsters (Charles River), approx. 10 weeks old, weighing approximately 100 gms. each. Each animal was housed separately, and was offered food and water ad libitum through the entire length of the study.

On day 1 of the study, the animals in all four groups were each predisposed to *C. difficile* infection by the oral administration of 3.0 mg of clindamycin-HCl (Sigma) in 1 ml of water.

On day 2, each animal in all four groups was orally challenged with 1 ml of *C. difficile* inoculum, which contained approximately 100 *C. difficile* strain 43596 organisms in sterile saline. *C. difficile* strain 43596 was chosen because it is representative of one of the most frequency-occurring serogroups isolated from patients with antibiotic-associated pseudomembranous colitis. [Delmee et al,, J. Clin. Microbiol., 28:2210–2214 (1990).] In addition, as this was the same *C. difficile* strain used in all of the previous Examples above, it was again used in order to provide experimental continuity.

On day 3 of the study (24 hrs. post-infection), treatment was started for two of the four groups of animals. Each animal of one group was orally administered 1.0 ml of the CTAB IgY preparation (prepared in section (a) above) at the following timepoints: 0 hrs., 4 hrs., and 8 hrs. The animals in this group were designated "CTAB-24." The animals in the second group were each orally administered 1.0 ml of the pre-immune IgY preparation (also prepared in section (a) above) at the same timepoints as for the CTAB group. These animals were designated "Pre-24." Nothing was done to the remaining two groups of animals on day 3.

On day 4, 48 hrs. post-infection, the treatment described for day 3 above was repeated for the CTAB-24 and Pre-24 groups, and was initiated for the remaining two groups at the same timepoints. The final two groups of animals were designated "CTAB48" and "Pre-48" respectively.

On days 5 through 9, the animals in all four groups were administered antitoxin or pre-immune IgY, 3× per day, as described for day 4 above. The four experimental groups are summarized in Table 14.

TABLE 14

Experimental Treatment Groups

| Group Designation | Experimental Treatment |
|---|---|
| CTAB-24 | Infected, treatment w/antitoxin IgY started @ 24 hrs. post-infection. |
| Pre-24 | Infected, treatment w/pre-immune IgY started @ 24 hrs. post-infection. |
| CTAB-48 | Infected, treatment w/antitoxin IgY started @ 48 hrs. post-infection. |

TABLE 14-continued

Experimental Treatment Groups

| Group Designation | Experimental Treatment |
|---|---|
| Pre-48 | Infected, treatment w/pre-immune IgY started @ 48 hrs. post-infection. |

All animals were observed for the onset of diarrhea and death through the conclusion of the study on the morning of day 10. The results of this study are displayed in Table 15.

Eighty-six percent of the animals which began receiving treatment with antitoxin IgY at 24 hrs. post-infection (CTAB-24 above) survived, while 57% of the animals treated with antitoxin IgY starting 48 hrs. post-infection (CTAB48 above) survived. In contrast none of the animals receiving pre-immune IgY starting 24 hrs. post-infection (Pre-24 above) survived, and only 29% of the animals which began receiving treatment with pre-immune IgY at 48 hrs. post-infection (Pre-48 above) survived through the conclusion of the study. These results demonstrate that avian antitoxins raised against *C. difficile* toxins A and B are capable of successfully treating established *C. difficile* infections in vivo.

TABLE 15

Experimental Outcome-Day 10

| Treatment Group | No. Animals Surviving | No. Animals Dead |
|---|---|---|
| CTAB-24 | 6 | 1 |
| Pre-24 | 0 | 7 |
| CTAB-48 | 4 | 3 |
| Pre-48 | 2 | 5 |

(c) Histologic Evaluation Of Cecal Tissue. In order to further evaluate the ability of the IgY preparations tested in this study to treat established *C. difficile* infection, histologic evaluations were performed on cecal tissue specimens obtained from representative animals from the study described in section (b) above.

Immediately following death, cecal tissue specimens were removed from animals which died in the Pre-24 and Pre-48 groups. Following the completion of the study, a representative surviving animal was sacrificed and cecal tissue specimens were removed from the CTAB-24 and CTAB-48 groups. A single untreated animal from the same shipment as those used in the study was also sacrificed and a cecal tissue specimen was removed as a normal control. All tissue specimens were fixed overnight at 4° C. in 10% buffered formalin. The fixed tissues were paraffin-embedded, sectioned, and mounted on glass microscope slides. The tissue sections were then stained using hematoxylin and eosin (H and E stain), and were examined by light microscopy.

Upon examination, the tissues obtained from the CTAB-24 and CTAB-48 animals showed no pathology, and were indistinguishable from the normal control. This observation provides further evidence for the ability of avian antitoxins raised against *C. difficile* toxins A and B to effectively treat established *C. difficile* infection, and to prevent the pathologic consequences which normally occur as a result of *C. difficile* disease.

In contrast, characteristic substantial mucosal damage and destruction was observed in the tissues of the animals from the Pre-24 and Pre-48 groups which died from *C. difficile* disease. Normal tissue architecture was obliterated in these two preparations, as most of the mucosal layer was observed to have sloughed away, and there were numerous large hemorrhagic areas containing massive numbers of erythrocytes.

EXAMPLE 11

Cloning And Expression Of *C. difficile* Toxin A Fragments

The toxin A gene has been cloned and sequenced, and shown to encode a protein of predicted MW of 308 kd. [Dove et al., Infect. Immun., 58:480–488 (1990).] Given the expense and difficulty of isolating native toxin A protein, it would be advantageous to use simple and inexpensive procaryotic expression systems to produce and purify high levels of recombinant toxin A protein for immunization purposes. Ideally, the isolated recombinant protein would be soluble in order to preserve native antigenicity, since solubilized inclusion body proteins often do not fold into native conformations. To allow ease of purification, the recombinant protein should be expressed to levels greater than 1 mg/liter of *E. coli* culture.

To determine whether high levels of recombinant toxin A protein can be produced in *E. coli,* fragments of the toxin A gene were cloned into various prokaryotic expression vectors, and assessed for the ability to express recombinant toxin A protein in *E. coli*. Three prokaryotic expression systems were utilized. These systems were chosen because they drive expression of either fusion (pMALc and pGEX2T) or native (pET23a–c) protein to high levels in *E. coli,* and allow affinity purification of the expressed protein on a ligand containing column. Fusion proteins expressed from pGEX vectors bind glutathione agarose beads, and are eluted with reduced glutathione. pMAL fusion proteins bind amylose resin, and are eluted with maltose. A polyhistidine tag is present at either the N-terminal (pET16b) or C-terminal (pET23a–c) end of pET fusion proteins. This sequence specifically binds $Ni_2^+$ chelate columns, and is eluted with imidazole salts. Extensive descriptions of these vectors are available (Williams et al., *DNA Cloning: Expression Systems,* in press), and will not be discussed in detail here. The Example involved (a) cloning of the toxin A gene, (b) expression of large fragments of toxin A in various prokaryotic expression systems, (c) identification of smaller toxin A gene fragments that express efficiently in *E. coli,* (d) purification of recombinant toxin A protein by affinity chromatography, and (e) demonstration of functional activity of a recombinant fragment of the toxin A gene.

(a) Cloning Of The Toxin A Gene. A restriction map of the toxin A gene is shown in FIG. 6 (SEQ ID NOS:1–4). The encoded protein contains a carboxy terminal ligand binding region, containing multiple repeats of a carbohydrate binding domain. [von Eichel-Streiber and Sauerborn, Gene 96:107–113 (1990).] The toxin A gene was cloned in three pieces, by using either the polymerase chain reaction (PCR) to amplify specific regions, (regions 1 and 2, FIG. 6 (SEQ ID NOS:1–4)) or by screening a constructed genomic library for a specific toxin A gene fragment (region 3, FIG. 6 (SEQ ID NOS:1–4)). The sequences of the utilized PCR primers are indicated in the legend to FIG. 6 (SEQ ID NOS:1–4). These regions were cloned into prokaryotic expression vectors that express either fusion (pMALc and pGEX2T) or native (pET23a–c) protein to high levels in *E. coli,* and allow affinity purification of the expressed protein on a ligand containing column.

*Clostridium difficile* VPI strain 10463 was obtained from the ATCC (ATCC #43255) and grown under anaerobic conditions in brain-heart infusion medium (BBL). High molecular-weight *C. difficile* DNA was isolated essentially as described by Wren and Tabaqchali, J Clin. Microbiol., 25:2402–2404 (1987), except proteinase K and sodium dodecyl sulfate (SDS) was used to disrupt the bacteria, and cetytrimethylammonium bromide precipitation [as described in Ausubel et al., *Current Protocols in Molecular Biology* (1989)] was used to remove carbohydrates from the cleared lysate. The integrity and yield of genomic DNA was assessed by comparison with a serial dilution of uncut lambda DNA after electrophoresis on an agarose gel.

Fragments 1 and 2 were cloned by PCR, utilizing a proofreading thermostable DNA polymerase (native pfu polymerase; Stratagene). The high fidelity of this polymerase reduces the mutation problems associated with amplification by error prone polymerases (e.g., Taq polymerase). PCR amplification was performed using the indicated PCR primers (FIG. 6 (SEQ ID NOS:1–4)) in 50 $\mu$l reactions containing 10 mM Tris-HCl(8.3), 50 mM KCl, 1.5 mM $MgCl_2$, 200 $\mu$M each dNTP, 0.2 $\mu$M each primer, and 50 ng *C. difficile* genomic DNA. Reactions were overlaid with 100 $\mu$l mineral oil, heated to 94° C. for 4 min, 0.5 $\mu$l native pfu polymerase (Stratagene) added, and the reaction cycled 30× at 94° C. for 1 min, 50° C. for 1 min, 72° C. for 4 min, followed by 10 min at 72° C. Duplicate reactions were pooled, chloroform extracted, and ethanol precipitated. After washing in 70% ethanol, the pellets were resuspended in 50 $\mu$l TE buffer [10 mM Tris-HCl, 1 mM EDTA pH 8.0]. Aliquots of 10 $\mu$l each were restriction digested with either EcoRI/HincII (fragment 1) or EcoRI/PstI (fragment 2), and the appropriate restriction fragments were gel purified using the Prep-A-Gene kit (BioRad), and ligated to either EcoRI/ SmaI-restricted pGEX2T (Pharmacia) vector (fragment 1), or the EcoRI/PstI PMA1c (New England Biolabs) vector (fragment 2). Both clones are predicted to produce in-frame fusions with either the glutathione-S-transferase protein (pGEX vector) or the maltose binding protein (pMAL vector). Recombinant clones were isolated, and confirmed by restriction digestion, using standard recombinant molecular biology techniques. [Sambrook et al., *Molecular Cloning, A Laboratory Manual* (1989)], and designated pGA30-660 and pMA660-1100, respectively (see FIG. 6 (SEQ ID NOS: 1–4) for description of the clone designations).

Fragment 3 was cloned from a genomic library of size selected PstI digested *C. difficile* genomic DNA, using standard molecular biology techniques (Sambrook et al.). Given that the fragment 3 internal PstI site is protected from cleavage in *C. difficile* genomic DNA [Price et al., Curr. Microbiol., 16:55–60 (1987)], 4.7 kb PstI restricted *C. difficile* genomic DNA was gel purified, and ligated to PstI restricted, phosphatase treated pUC9 DNA. The resulting genomic library was screened with a oligonucleotide primer specific to fragment 3, and multiple independent clones were isolated. The presence of fragment 3 in several of these clones was confirmed by restriction digestion, and a clone of the indicated orientation (FIG. 6 (SEQ ID NOS:1–4)) was restricted with BamHI/HindIII, the released fragment purified by gel electrophoresis, and ligated into similarly restricted pET23c expression vector DNA (Novagen). Recombinant clones were isolated, and confirmed by restriction digestion. This construct is predicted to create both a predicted in frame fusion with the pET protein leader sequence, as well as a predicted C-terminal poly-histidine affinity tag, and is designated pPA1100-2680 (see FIG. 6 (SEQ ID NOS:1–4) for the clone designation).

Figure 7A:
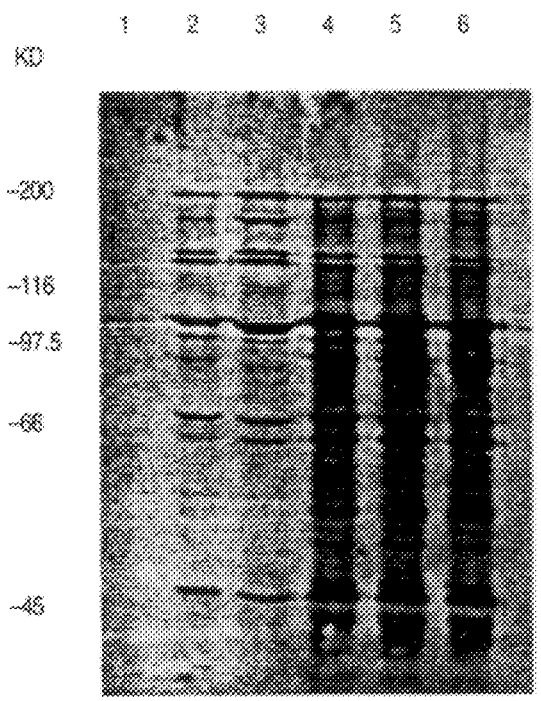
FIG. 7 is a Western blot of C. difficile toxin A reactive protein.
Figure 7B:
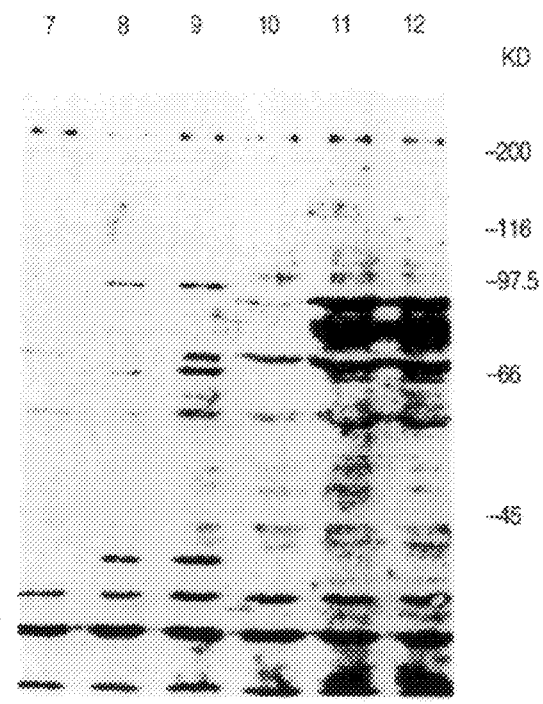

(b) Expression Of Large Fragments Of Toxin A In *E coli*. Protein expression from the three expression constructs made in (a) was induced, and analyzed by Western blot analysis with an affinity purified, goat polyclonal antiserum directed against the toxin A toxoid (Tech Lab). The procedures utilized for protein induction, SDS-PAGE, and Western blot analysis are described in detail in Williams et al. In brief, 5 ml 2XYT (16 g. tryptone, 10 g. yeast extract, 5 g. NaCl per liter, pH 7.5)+100 µg/ml ampicillin were added to cultures of bacteria (BL21 for pMA1 and pGEX plasmids, and BL21(DE3)LysS for pET plasmids) containing the appropriate recombinant clone which were induced to express recombinant protein by addition of IPTG to 1 mM. Cultures were grown at 37° C., and induced when the cell density reached 0.5 $OD_{600}$. Induced protein was allowed to accumulate for two hrs after induction. Protein samples were prepared by pelleting 1 ml aliquots of bacteria by centrifugation (1 min in a microfuge), and resuspension of the pelleted bacteria in 150 µl of 2× SDS-PAGE sample buffer (Williams et al.). The samples were heated to 95° C. for 5 min, the cooled and 5 or 10 µl aliquots loaded on 7.5% SDS-PAGE gels. BioRad high molecular weight protein markers were also loaded, to allow estimation of the MW of identified fusion proteins. After electrophoresis, protein was detected either generally by staining gels with coomassie blue, or specifically, by blotting to nitrocellulose for Western blot detection of specific immunoreactive protein. Western blots, (performed as described in Example 3) which detect toxin A reactive protein in cell lysates of induced protein from the three expression constructs are shown in FIG. 7. In this figure, lanes 1–3 contain cell lysates prepared from *E. coli* strains containing pPA1100-2860 in B121(DE3)lysE cells; lanes 4–6 contain cell lysates prepared from *E. coli* strains containing pPA1100-2860 in B121(DE3)lysS cells; lanes 7–9 contain cell lysates prepared from *E. coli* strains containing pMA30-660; lanes 10–12 contain cell lysates prepared from *E. coli* strains containing pMA660- 1100. The lanes were probed with an affinity purified goat antitoxin A polyclonal antibody (Tech Lab). Control lysates from uninduced cells (lanes 1, 7, and 10) contain very little immunoreactive material compared to the induced samples in the remaining lanes. The highest molecular weight band observed for each clone is consistent with the predicted size of the full length fusion protein.

Figure 8:
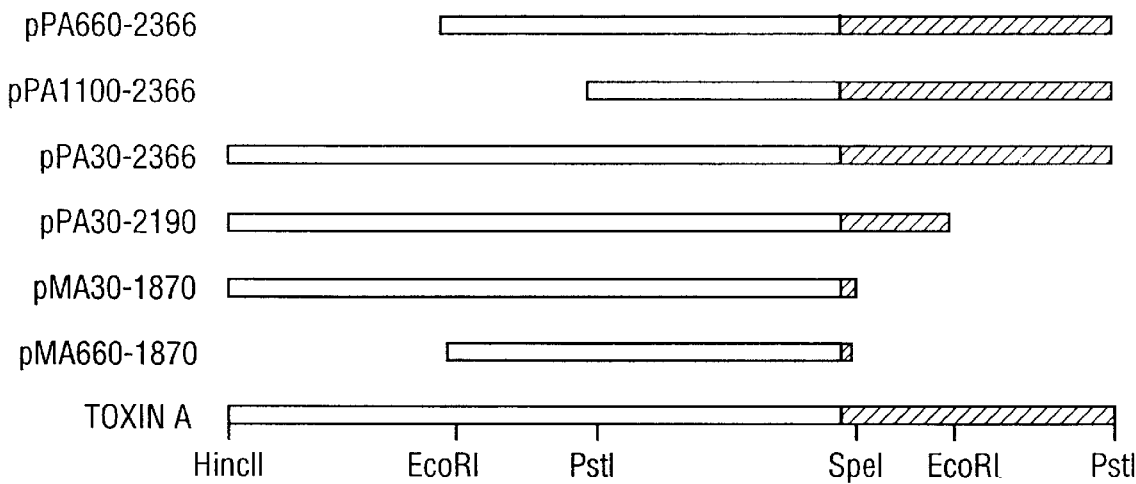
FIG. 8 shows C. difficile toxin A expression constructs.

Each construct directs expression of high molecular weight (HMW) protein that is reactive with the toxin A antibody. The size of the largest immunoreactive bands from each sample is consistent with predictions of the estimated MW of the intact fusion proteins. This demonstrates that the three fusions are in-frame, and that none of the clones contain cloning artifacts that disrupt the integrity of the encoded fusion protein. However, the Western blot demonstrates that fusion protein from the two larger constructs (pGA30-660 and pPA1100-2680) are highly degraded. Also, expression levels of toxin A proteins from these two constructs are low, since induced protein bands are not visible by Coomassie staining (not shown). Several other expression constructs that fuse large sub-regions of the toxin A gene to either pMALc or pET23a–c expression vectors, were constructed and tested for protein induction. These constructs were made by mixing gel purified restriction fragments, derived from the expression constructs shown in FIG. 6 (SEQ ID NOS:1–4), with appropriately cleaved expression vectors, ligating, and selecting recombinant clones in which the toxin A restriction fragments had ligated together and into the expression vector as predicted for in-frame fusions. The expressed toxin A interval within these constructs are shown in FIG. 8, as well as the internal restriction sites utilized to make these constructs.

As used herein, the term "interval" refers to any portion (i.e., any segment of the toxin which is less than the whole toxin molecule) of a clostridial toxin. In a preferred embodiment, "interval" refers to portions of *C. difficile* toxins such as toxin A. It is also contemplated that these intervals will correspond to epitopes of immunologic importance, such as antigens or immunogens against which a neutralizing antibody response is effected. It is not intended that the present invention be limited to the particular intervals or sequences described in these Examples. It is also contemplated that sub-portions of intervals (e.g., an epitope contained within one interval or which bridges multiple intervals) be used as compositions and in the methods of the present invention.

In all cases, Western blot analysis of each of these constructs with goat antitoxin A antibody (Tech Lab) detected HMW fusion protein of the predicted size (not shown). This confirms that the reading frame of each of these clones is not prematurely terminated, and is fused in the correct frame with the fusion partner. However, the Western blot analysis revealed that in all cases, the induced protein is highly degraded, and, as assessed by the absence of identifiable induced protein bands by Coomassie Blue staining, are expressed only at low levels. These results suggest that expression of high levels of intact toxin A recombinant protein is not possible when large regions of the toxin A gene are expressed in *E. coli* using these expression vectors.

Figure 9:
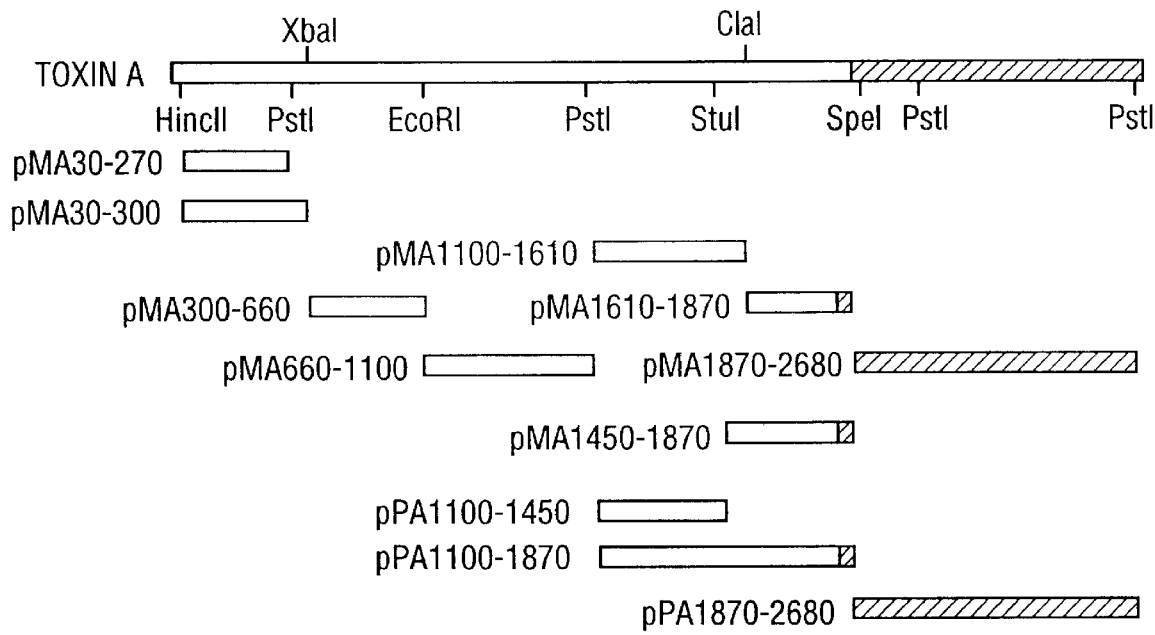
FIG. 9 shows C. difficile toxin A expression constructs.

(c) High Level Expression Of Small Toxin A Protein Fusions In *E. coli*. Experience indicates that expression difficulties are often encountered when large (greater than 100 kd) fragments are expressed in *E. coli*. A number of expression constructs containing smaller fragments of the toxin A gene were constructed, to determine if small regions of the gene can be expressed to high levels without extensive protein degradation. A summary of these expression constructs are shown in FIG. 9. All were constructed by in-frame fusions of convenient toxin A restriction fragments to either the pMALc or pEM23a–c vectors. Protein preparations from induced cultures of each of these constructs were analyzed by both Coomassie and Western analysis as in (b) above. In all cases, higher levels of intact, full length fusion proteins were observed than with the larger recombinants from section (b).

Figure 10A:
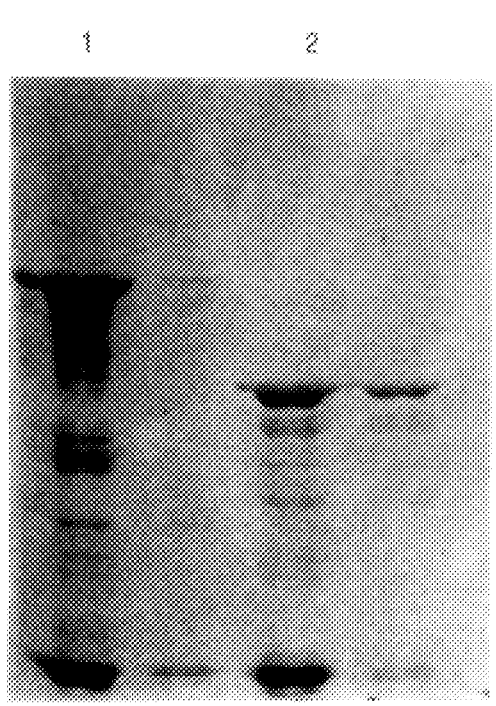
FIG. 10 shows the purification of recombinant C. difficile toxin A.
Figure 10B:
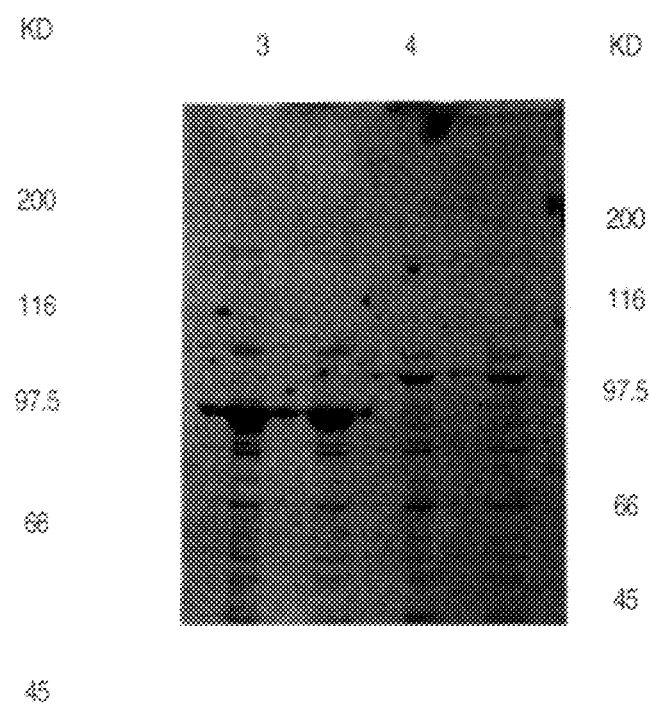

(d) Purification Of Recombinant Toxin A Protein. Large scale (500 ml) cultures of each recombinant from (c) were grown, induced, and soluble and insoluble protein fractions were isolated. The soluble protein extracts were affinity chromatogrammed to isolate recombinant fusion protein, as described (Williams et al.). In brief, extracts containing tagged pET fusions were chromatogrammed on a nickel chelate column, and eluted using imidazole salts as described by the distributor (Novagen). Extracts containing soluble pMAL fusion protein were prepared and chromatogrammed in column buffer (10 mM NaPO4, 0.5M NaCl, 10 mM B-mercaptoethanol, pH 7.2) over an amylose resin column (New England Biolabs), and eluted with column buffer containing 10 mM maltose as described (Williams et al.). When the expressed protein was found to be predominantly insoluble, insoluble protein extracts were prepared by a proprietary method, described in (Williams et al.) The results are summarized in Table 16. FIG. 10 shows the sample purifications of recombinant toxin A protein. In this figure, lanes 1 and 2 contain MBP fusion protein purified by affinity purification of soluble protein. Lanes 3 and 4 contain MBP fusion protein purified by solubilization of insoluble inclusion bodies. The purified fusion protein samples are pMA1870-2680 (lane 1),d pMA660-1 100 (lane 2), pMA300-600 (lane 3) and pMA1450-1870 (lane 4).

TABLE 16

Purification Of Recombinant Toxin A Protein

| Clone[a] | Protein Solubility | Yield Affinity Purified Soluble Protein[b] | % Intact Soluble Fusion Protein[c] | Yield Intact Insoluble Fusion Protein |
|---|---|---|---|---|
| pMA30-270 | Soluble | 4 mg/500 mls | 10% | NA |
| PMA30-300 | Soluble | 4 mg/500 mls | 5–10% | NA |
| pMA300-660 | Insoluble | — | NA | 10 mg/500 ml |
| pMA660-1100 | Soluble | 4.5 mg/500 mls | 50% | NA |
| pMA1100-1610 | Soluble | 18 mg/500 mls | 10% | NA |
| pMA1610-1870 | Both | 22 mg/500 mls | 90% | 20 mg/500 ml |
| pMA1450-1870 | Insoluble | — | NA | 0.2 mg/500 ml |
| pPA1100-1450 | Soluble | 0.1 mg/500 mls | 90% | NA |
| pPA1100-1870 | Soluble | 0.02 mg/500 mls | 90% | NA |
| pMA1870-2680 | Both | 12 mg/500 mls | 80% | NA |
| pPa1870-2680 | Insoluble | — | NA | 10 mg/500 ml |

[a]pP = pET23 vector, pM = pMALc vector, A = toxin A.
[b]Based on 1.5 $OD_{280}$ = 1 mg/ml (extinction coefficient of MBP).
[c]Estimated by Coomassie staining of SDS-PAGE gels.

Poor yields of affinity purified protein were obtained when poly-histidine tagged pET vectors were used to drive expression (pPA1100-1450, pP1100-1870). However, significant protein yields were obtained from pMAL expression constructs spanning the entire toxin A gene, and yields of full-length soluble fusion protein ranged from an estimated 200–400 μg/500 ml culture (pMA30-300) to greater than 20 mg/500 ml culture (pMA1610-1870). Only one interval is expressed to high levels as strictly insoluble protein (pMA300-660). Thus, although high level expression was not observed when using large expression constructs from the toxin A gene, usable levels of recombinant protein spanning the entire toxin A gene were obtainable by isolating induced protein from a series of smaller pMAL expression constructs that span the entire toxin A gene. This is the first demonstration of the feasibility of expressing recombinant toxin A protein to high levels in *E. coli*.

(e) Hemagglutination Assay Using The Toxin A Recombinant Proteins. The carboxy terminal end consisting of the repeating units contains the hemagglutination activity or binding domain of *C. difficile* toxin A. To determine whether the expressed toxin A recombinants retain functional activity, hemagglutination assays were performed. Two toxin A recombinant proteins, one containing the binding domain as either soluble affinity purified protein (pMA1870-2680) or SDS solubilized inclusion body protein (pPA1870-2680) and soluble protein from one region outside that domain (pMA1100-1610) were tested using a described procedure. [H. C. Krivan et. al., Infect. Immun., 53:573 (1986).] Citrated rabbit red blood cells (RRBC)(Cocalico) were washed several times with Tris-buffer ( 0.1M Tris and 50 mM NaCl ) by centrifugation at 450×g for 10 minutes at 4° C. A 1% RRBC suspension was made from the packed cells and resuspended in Tris-buffer. Dilutions of the recombinant proteins and native toxin A (Tech Labs) were made in the Tris-buffer and added in duplicate to a round-bottomed 96-well microtiter plate in a final volume of 100 μl. To each well, 50 μl of the 1% RRBC suspension was added, mixed by gentle tapping, and incubated at 4° C. for 3–4 hours. Significant hemagglutination occurred only in the recombinant proteins containing the binding domain (pMA 1870-2680) and native toxin A. The recombinant protein outside the binding domain (pMA 1100-1610) displayed no hemagglutination activity. Using equivalent protein concentrations, the hemagglutination titer for toxin A was 1:256, while titers for the soluble and insoluble recombinant proteins of the binding domain were 1:256 and about 1:5000. Clearly, the recombinant proteins tested retained functional activity and were able to bind RRBC's.

EXAMPLE 12

Functional Activity Of IgY Reactive Against Toxin A Recombinants

The expression of recombinant toxin A protein as multiple fragments in *E. coli* has demonstrated the feasibility of generating toxin A antigen through use of recombinant methodologies (Example 11). The isolation of these recombinant proteins allows the immunoreactivity of each individual subregion of the toxin A protein to be determined (i.e., in a antibody pool directed against the native toxin A protein). This identifies the regions (if any) for which little or no antibody response is elicited when the whole protein is used as a immunogen. Antibodies directed against specific fragments of the toxin A protein can be purified by affinity chromatography against recombinant toxin A protein, and tested for neutralization ability. This identifies any toxin A subregions that are essential for producing neutralizing antibodies. Comparison with the levels of immune response directed against these intervals when native toxin is used as an immunogen predicts whether potentially higher titers of neutralizing antibodies can be produced by using recombinant protein directed against a individual region, rather than the entire protein. Finally, since it is unknown whether antibodies reactive to the recombinant toxin A proteins produced in Example 11 neutralize toxin A as effectively as antibodies raised against native toxin A (Examples 9 and 10), the protective ability of a pool of antibodies affinity purified against recombinant toxin A fragments was assessed for its ability to neutralize toxin A.

This Example involved (a) epitope mapping of the toxin A protein to determine the titre of specific antibodies directed against individual subregions of the toxin A protein when native toxin A protein is used as an immunogen, (b) affinity purification of IgY reactive against recombinant protein spanning the toxin A gene, (c) toxin A neutralization assays with affinity purified IgY reactive to recombinant toxin A protein to identify subregions of the toxin A protein that induce the production of neutralizing antibodies, and determination of whether complete neutralization of toxin A can be elicited with a mixture of antibodies reactive to recombinant toxin A protein.

(a) Epitope Mapping Of The Toxin A Gene. The affinity purification of recombinant toxin A protein specific to defined intervals of the toxin A protein allows epitope mapping of antibody pools directed against native toxin A. This has not previously been possible, since previous expression of toxin A recombinants has been assessed only by Western blot analysis, without knowledge of the expression levels of the protein [e.g., von Eichel-Streiber et al., J. Gen. Microbiol., 135:55–64 (1989)]. Thus, high or low reactivity of recombinant toxin A protein on Western blots may reflect protein expression level differences, not immunoreactivity differences. Given that the purified recombinant proteins generated in Example 11 have been quantitated, the issue of relative immunoreactivity of individual regions of the toxin A protein was precisely addressed.

For the purposes of this Example, the toxin A protein was subdivided into 6 intervals (1–6), numbered from the amino (interval 1) to the carboxyl (interval 6) termini.

The recombinant proteins corresponding to these intervals were from expression clones (see Example 11(d) for clone designations) pMA30-300 (interval 1), pMA300-660 (interval 2), pMA660-1100 (interval 3), pPA1100-1450 (interval 4), pMA1450-1870 (interval 5) and pMA1870-2680 (interval 6). These 6 clones were selected because they span the entire protein from amino acids numbered 30 through 2680, and subdivide the protein into 6 small intervals. Also, the carbohydrate binding repeat interval is contained specifically in one interval (interval 6), allowing evaluation of the immune response specifically directed against this region. Western blots of 7.5% SDS-PAGE gels, loaded and electrophoresed with defined quantities of each recombinant protein, were probed with either goat antitoxin A polyclonal antibody (Tech Lab) or chicken antitoxin A polyclonal antibody [PCTA IgY, Example 8(c)]. The blots were prepared and developed with alkaline phosphatase as previously described (Williams et al). At least 90% of all reactivity, in either goat or chicken antibody pools, was found to be directed against the ligand binding domain (interval 6). The remaining immunoreactivity was directed against all five remaining intervals, and was similar in both antibody pools, except that the chicken antibody showed a much lower reactivity against interval 2 than the goat antibody.

This clearly demonstrates that when native toxin A is used as an immunogen in goats or chickens, the bulk of the immune response is directed against the ligand binding domain of the protein, with the remaining response distributed throughout the remaining ⅔ of the protein.

(b) Affinity Purification Of IgY Reactive Against Recombinant Toxin A Protein. Affinity columns, containing recombinant toxin A protein from the 6 defined intervals in (a) above, were made and used to (i) affinity purify antibodies reactive to each individual interval from the CTA IgY preparation [Example 8(c)], and (ii) deplete interval specific antibodies from the CTA IgY preparation. Affinity columns were made by coupling 1 ml of PBS-washed Actigel resin (Sterogene) with region specific protein and 1/10 fmal volume of Aid-coupling solution (1M sodium cyanoborohydride). The total region specific protein added to each reaction mixture was 2.7 mg (interval 1), 3 mg (intervals 2 and 3), 0.1 mg (interval 4), 0.2 mg (interval 5) and 4 mg (interval 6). Protein for intervals 1, 3, and 6 was affinity purified pMA1 fusion protein in column buffer (see Example 11). Interval 4 was affinity purified poly-histidine containing pET fusion in PBS; intervals 2 and 5 were from inclusion body preparations of insoluble pMAL fusion protein, dialysed extensively in PBS. Aliquots of the supernatants from the coupling reactions, before and after coupling, were assessed by Coomassie staining of 7.5% SDS-PAGE gels. Based on protein band intensities, in all cases greater than 50% coupling efficiencies were estimated. The resins were poured into 5 ml BioRad columns, washed extensively with PBS, and stored at 4° C.

Aliquots of the CTA IgY polyclonal antibody preparation were depleted for each individual region as described below. A 20 ml sample of the CTA IgY preparation [Example 8(c)] was dialysed extensively against 3 changes of PBS (1 liter for each dialysis), quantitated by absorbance at $OD_{280}$, and stored at 4° C. Six 1 ml aliquots of the dialysed IgY preparation were removed, and depleted individually for each of the six intervals. Each 1 ml aliquot was passed over the appropriate affinity column, and the eluate twice reapplied to the column. The eluate was collected, and pooled with a 1 ml PBS wash. Bound antibody was eluted from the column by washing with 5 column volumes of 4M Guanidine-HCl (in 10 mM Tris-HCl, pH 8.0). The column was reequilibrated in PBS, and the depleted antibody stock reapplied as described above. The eluate was collected, pooled with a 1 ml PBS wash, quantitated by absorbance at $OD_{280}$, and stored at 4° C. In this manner, 6 aliquots of the CTA IgY preparation were individually depleted for each of the 6 toxin A intervals, by two rounds of affinity depletion. The specificity of each depleted stock was tested by Western blot analysis. Multiple 7.5% SDS-PAGE gels were loaded with protein samples corresponding to all 6 toxin A subregions. After electrophoresis, the gels were blotted, and protein transfer confirmed by Ponceau S staining (protocols described in Williams et al). After blocking the blots 1 hr at 20° C. in PBS+0.1% Tween 20 (PBST) containing 5% milk (as a blocking buffer), 4 ml of either a 1/500 dilution of the dialysed CTA IgY preparation in blocking buffer, or an equivalent amount of the six depleted antibody stocks (using $OD_{280}$ to standardize antibody concentration) were added and the blots incubated a further 1 hr at room temperature. The blots were washed and developed with alkaline phosphatase (using a rabbit anti-chicken alkaline phosphate conjugate as a secondary antibody) as previously described (Williams et al). In all cases, only the target interval was depleted for antibody reactivity, and at least 90% of the reactivity to the target intervals was specifically depleted.

Region specific antibody pools were isolated by affinity chromatography as described below. Ten mls of the dialysed CTA IgY preparation were applied sequentially to each affinity column, such that a single 10 ml aliquot was used to isolate region specific antibodies specific to each of the six subregions. The columns were sequentially washed with 10 volumes of PBS, 6 volumes of BBS-Tween, 10 volumes of TBS, and eluted with 4 ml Actisep elution media (Sterogene). The eluate was dialysed extensively against several changes of PBS, and the affinity purified antibody collected and stored at 4° C. The volumes of the eluate increased to greater than 10 mls during dialysis in each case, due to the high viscosity of the Actisep elution media Aliquots of each sample were 20× concentrated using Centricon 30 microconcentrators (Amicon) and stored at 4° C. The specificity of each region specific antibody pool was tested, relative to the dialysed CTA IgY preparation, by Western blot analysis, exactly as described above, except that 4 ml samples of blocking buffer containing 100 $\mu$l region specific antibody (unconcentrated) were used instead of the depleted CTA IgY preparations. Each affinity purified antibody preparation was specific to the defined interval, except that samples purified against intervals 1–5 also reacted with interval 6. This may be due to non-specific binding to the interval 6 protein, since this protein contains the repetitive ligand binding domain which has been shown to bind antibodies nonspecifically. [Lyerly et al., Curr. Microbiol., 19:303–306 (1989).]

The reactivity of each affinity purified antibody preparation to the corresponding proteins was approximately the same as the reactivity of the 1/500 diluted dialysed CTA IgY preparation standard. Given that the specific antibody stocks were diluted 1/40, this would indicate that the unconcentrated affinity purified antibody stocks contain 1/10–1/20 the concentration of specific antibodies relative to the starting CTA IgY preparation.

(c) Toxin A Neutralization Assay Using Antibodies Reactive Toward Recombinant Toxin A Protein. The CHO toxin neutralization assay [Example 8(d)] was used to assess the ability of the depleted or enriched samples generated in (b) above to neutralize the cytotoxicity of toxin A. The general ability of affinity purified antibodies to neutralize toxin A was assessed by mixing together aliquots of all 6 concentrated stocks of the 6 affinity purified samples generated in (b) above, and testing the ability of this mixture to neutralize a toxin A concentration of 0.1 μg/ml. The results, shown in FIG. 11, demonstrate almost complete neutralization of toxin A using the affinity purified (AP) mix. Some epitopes within the recombinant proteins utilized for affinity purification were probably lost when the proteins were denatured before affinity purification [by Guanidine-HCl treatment in (b) above]. Thus, the neutralization ability of antibodies directed against recombinant protein is probably underestimated using these affinity purified antibody pools. This experiment demonstrates that antibodies reactive to recombinant toxin A can neutralize cytotoxicity, suggesting that neutralizing antibodies may be generated by using recombinant toxin A protein as immunogen.

In view of the observation that the recombinant expression clones of the toxin A gene divide the protein into 6 subregions, the neutralizing ability of antibodies directed against each individual region was assessed. The neutralizing ability of antibodies directed against the ligand binding domain of toxin A was determined first.

Figure 11:
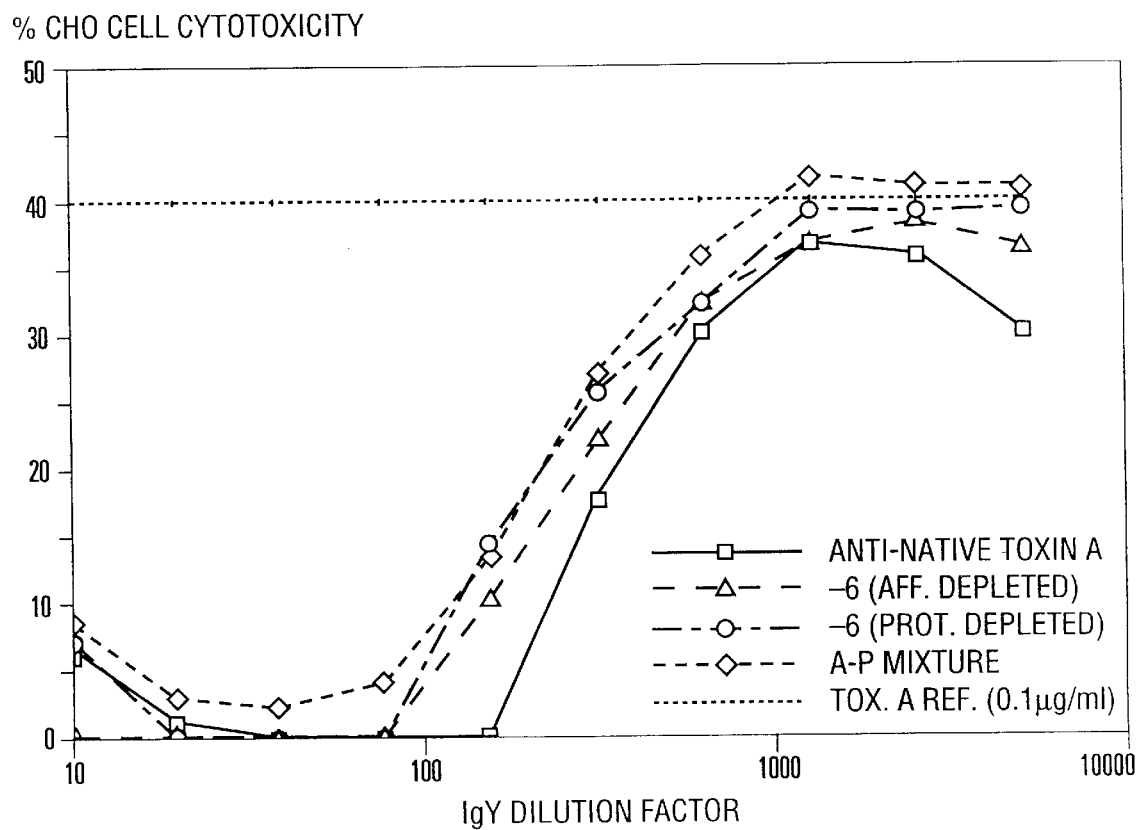
FIG. 11 shows the results of C. difficile toxin A neutralization assays with antibodies reactive to recombinant toxin A.

In the toxin neutralization experiment shown in FIG. 11, interval 6 specific antibodies (interval 6 contains the ligand binding domain) were depleted from the dialysed PEG preparation, and the effect on toxin neutralization assayed. Interval 6 antibodies were depleted either by utilizing the interval 6 depleted CTA IgY preparation from (b) above ("−6 aff. depleted" in FIG. 11), or by addition of interval 6 protein to the CTA IgY preparation (estimated to be a 10 fold molar excess over anti-interval 6 immunoglobulin present in this preparation) to competitively compete for interval 6 protein ("−6 prot depleted" in FIG. 11). In both instances, removal of interval 6 specific antibodies reduces the neutralization efficiency relative to the staring CTA IgY preparation. This demonstrates that antibodies directed against interval 6 contribute to toxin neutralization. Since interval 6 corresponds to the ligand binding domain of the protein, these results demonstrate that antibodies directed against this region in the PEG preparation contribute to the neutralization of toxin A in this assay. However, it is significant that after removal of these antibodies, the PEG preparation retains significant ability to neutralize toxin A. (FIG. 11). This neutralization is probably due to the action of antibodies specific to other regions of the toxin A protein, since at least 90% of the ligand binding region reactive antibodies were removed in the depleted sample prepared in (b) above. This conclusion was supported by comparison of the toxin neutralization of the affinity purified (AP) mix compared to affinity purified interval 6 antibody alone. Although some neutralization ability was observed with AP interval 6 antibodies alone, the neutralization was significantly less than that observed with the mixture of all 6 AP antibody stocks (not shown).

Figure 12:
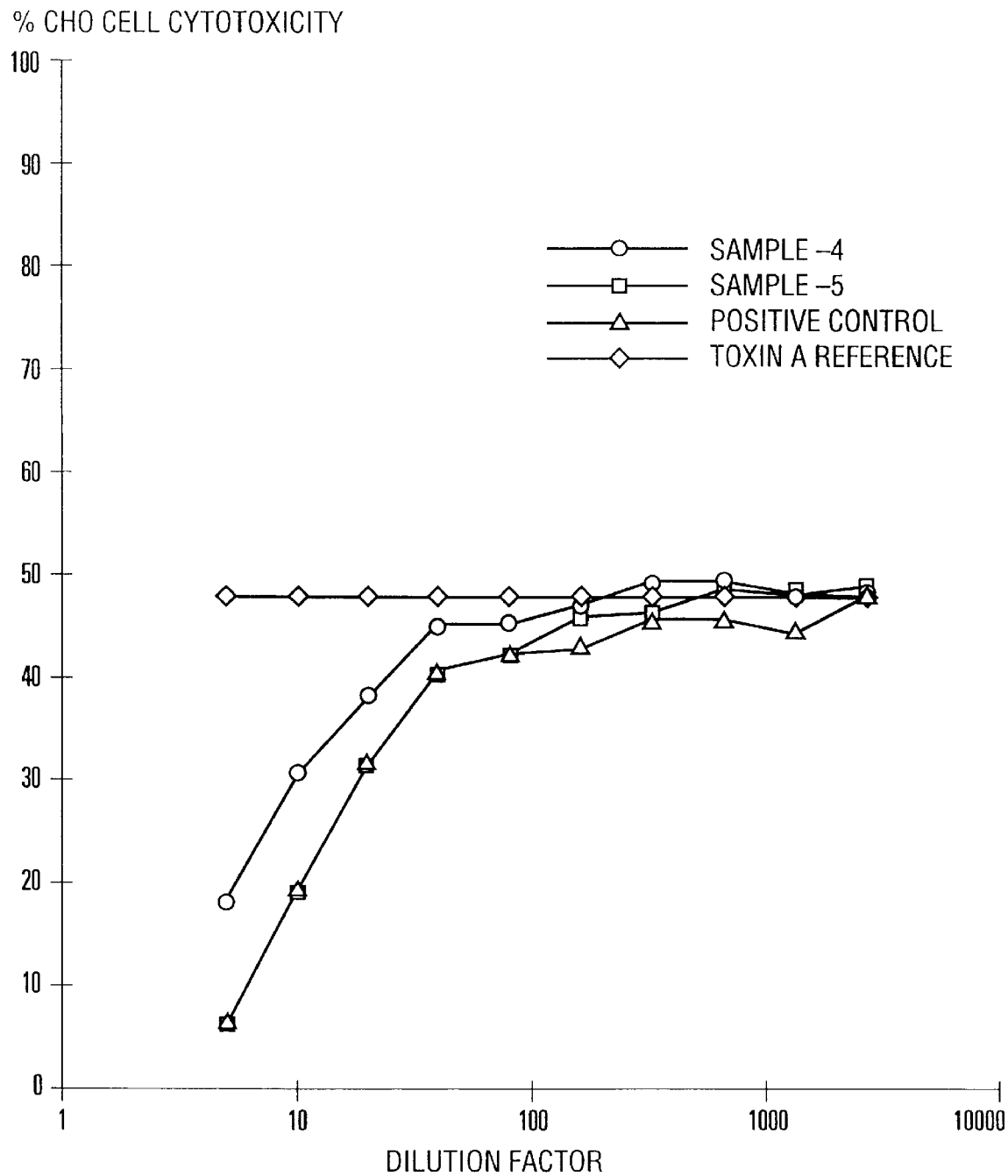
FIG. 12 shows the results for a C. difficile toxin A neutralization plate.

Given that the mix of all six affinity purified samples almost completely neutralized the cytotoxicity of toxin A (FIG. 11), the relative importance of antibodies directed against toxin A intervals 1–5 within the mixture was determined. This was assessed in two ways. First, samples containing affinity purified antibodies representing 5 of the 6 intervals were prepared, such that each individual region was depleted from one sample. FIG. 12 demonstrates a sample neutralization curve, comparing the neutralization ability of affinity purified antibody mixes without interval 4 (−4) or 5 (−5) specific antibodies, relative to the mix of all 6 affinity purified antibody stocks (positive control). While the removal of interval 5 specific antibodies had no effect on toxin neutralization (or intervals 1–3, not shown), the loss of interval 4 specific antibodies significantly reduced toxin neutralization (FIG. 12).

Figure 13:
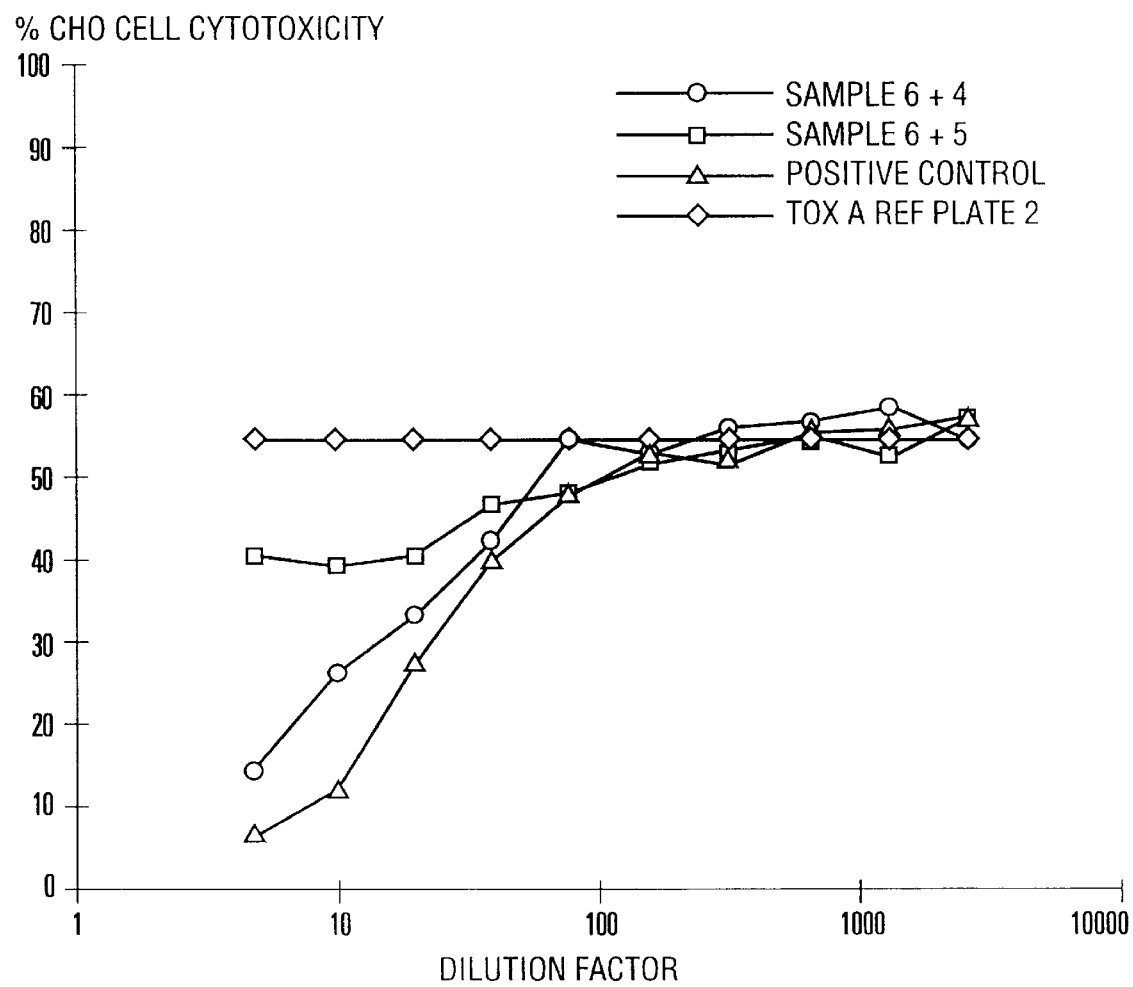
FIG. 13 shows the results for a C. difficile toxin A neutralization plate.

Similar results were seen in a second experiment, in which affinity purified antibodies, directed against a single region, were added to interval 6 specific antibodies, and the effects on toxin neutralization assessed. Only interval 4 specific antibodies significantly enhanced neutralization when added to interval 6 specific antibodies (FIG. 13). These results demonstrate that antibodies directed against interval 4 (corresponding to clone pPA1100-1450 in FIG. 9) are important for neutralization of cytotoxicity in this assay. Epitope mapping has shown that only low levels of antibodies reactive to this region are generated when native toxin A is used as an immunogen [Example 12(a)]. It is hypothesized that immunization with recombinant protein specific to this interval will elicit higher titers of neutralizing antibodies. In summary, this analysis has identified two critical regions of the toxin A protein against which neutralizing antibodies are produced, as assayed by the CHO neutralization assay.

EXAMPLE 13

Production And Evaluation Of Avian Antitoxin Against *C. difficile* Recombinant Toxin A Polypeptide In Example 12, we demonstrated neutralization of toxin A mediated cytotoxicity by affinity purified antibodies reactive to recombinant toxin A protein. To determine whether antibodies raised against a recombinant polypeptide fragment of *C. difficile* toxin A may be effective in treating clostridial diseases, antibodies to recombinant toxin A protein representing the binding domain were generated. Two toxin A binding domain recombinant polypetides, expressing the binding domain in either the pMALc (pMA1870-2680) or pET 23(pPA1870-2680) vector, were used as immunogens. The pMAL protein was affinity purified as a soluble product [Example 12(d)] and the pET protein was isolated as insoluble inclusion bodies [Example 12(d)] and solublized to an immunologically active protein using a proprietary method described in a pending patent application (U.S. patent application Ser. No. 08/129,027). This Example involves (a) immunization, (b) antitoxin collection, (c) determination of antitoxin antibody titer, (d) anti-recombinant toxin A neutralization of toxin A hemagglutination activity in vitro, and (e) assay of in vitro toxin A neutralizing activity.

(a) Immunization. The soluble and the inclusion body preparations each were used separately to immunize hens. Both purified toxin A polypeptides were diluted in PBS and emulsified with approximately equal volumes of CFA for the initial immunization or IFA for subsequent booster immunizations. On day zero, for each of the recombinant preparations, two egg laying white Leghorn hens (obtained from local breeder) were each injected at multiple sites (intramuscular and subcutaneous) with 1 ml of recombinant adjuvant mixture containing approximately 0.5 to 1.5 mgs of recombinant toxin A. Booster immunizations of 1.0 mg were given on days 14 and day 28.

(b) Antitoxin Collection. Total yolk immune IgY was extracted as described in the standard PEG protocol (as in Example 1) and the final IgY pellet was dissolved in sterile PBS at the original yolk volume. This material is designated "immune recombinant IgY" or "immune IgY."

(c) Antitoxin Antibody Titer. To determine if the recombinant toxin A protein was sufficiently immunogenic to raise antibodies in hens, the antibody titer of a recombinant toxin A polypeptide was determined by ELISA. Eggs from both hens were collected on day 32, the yolks pooled and the antibody was isolated using PEG as described. The immune recombinant IgY antibody titer was determined for the soluble recombinant protein containing the maltose binding protein fusion generated in p-Ma1 (pMA1870-2680). Ninety-six well Falcon Pro-bind plates were coated overnight at 4° C. with 100 μl/well of toxin A recombinant at 2.5 μg/μl in PBS containing 0.05% thimerosal. Another plate was also coated with maltose binding protein (MBP) at the same concentration, to permit comparison of antibody reactivity to the fusion partner. The next day, the wells were blocked with PBS containing 1% bovine serum albumin (BSA) for 1 hour at 37° C. IgY isolated from immune or preimmune eggs was diluted in antibody diluent (PBS containing 1% BSA and 0.05% Tween-20), and added to the blocked wells and incubated for 1 hour at 37° C. The plates were washed three times with PBS with 0.05% Tween-20, then three times with PBS. Alkaline phosphatase conjugated rabbit anti-chicken IgG (Sigma) diluted 1:1000 in antibody diluent was added to the plate, and incubated for 1 hour at 37° C. The plates were washed as before and substrate was added, [p-nitrophenyl phosphate (Sigma)] at 1 mg/ml in 0.05M $Na_2 CO_3$, pH 9.5 and 10 mM $MgCl_2$. The plates were evaluated quantitatively on a Dynatech MR 300 Micro EIA plate reader at 410 nm about 10 minutes after the addition of substrate.

Based on these ELISA results, high antibody titers were raised in chickens immunized with the toxin A recombinant polypeptide. The recombinant appeared to be highly immunogenic, as it was able to generate high antibody titers relatively quickly with few immunizations. Immune IgY titer directed specifically to the toxin A portion of the recombinant was higher than the immune IgY titer to its fusion partner, the maltose binding protein, and significantly higher than the preimmune IgY. ELISA titers (reciprocal of the highest dilution of IgY generating a signal) in the preimmune IgY to the MBP or the recombinant was <1:30 while the immune IgY titers to MBP and the toxin A recombinant were 1:18750 and >1:93750 respectively. Importantly, the anti-recombinant antibody titers generated in the hens against the recombinant polypeptide is much higher, compared to antibodies to that region raised using native toxin A. The recombinant antibody titer to region 1870–2680 in the CTA antibody preparation is at least five-fold lower compared to the recombinant generated antibodies (1:18750 versus >1:93750). Thus, it appears a better immune response can be generated against a specific recombinant using that recombinant as the immunogen compared to the native toxin A.

This observation is significant, as it shows that because recombinant portions stimulate the production of antibodies, it is not necessary to use native toxin molecules to produce antitoxin preparations. Thus, the problems associated with the toxicity of the native toxin are avoided and large-scale antitoxin production is facilitated.

(d) Anti-recombinant Toxin A Neutralization of Toxin A Hemagglutination Activity in vitro. Toxin A has hemagglutinating activity besides cytotoxic and enterotoxic properties. Specifically, toxin A agglutinates rabbit erythrocytes by binding to a trisaccharide (gal 1–3B1–4G1cNAc) on the cell surface. [H. Krivan et al., Infect. Immun., 53:573–581 (1986).] We examined whether the anti-recombinant toxin A (immune IgY, antibodies raised against the insoluble product expressed in pET) can neutralize the hemagglutination activity of toxin A in vitro. The hemagglutination assay procedure used was described by H. C. Krivan et al. Polyethylene glycol-fractionated immune or preimmune IgY were pre-absorbed with citrated rabbit erythrocytes prior to performing the hemagglutination assay because we have found that IgY alone can agglutinate red blood cells. Citrated rabbit red blood cells (RRBC's)(Cocalico) were washed twice by centrifugation at 450×g with isotonic buffer (0.1M Tris-HCl, 0.05M NaCl, pH 7.2). RRBC-reactive antibodies in the IgY were removed by preparing a 10% RRBC suspension (made by adding packed cells to immune or preimmune IgY) and incubating the mixture for 1 hour at 37° C. The RRBCs were then removed by centrifugation. Neutralization of the hemagglutination activity of toxin A by antibody was tested in round-bottomed 96-well microtiter plates. Twenty-five μl of toxin A (36 μg/ml) (Tech Lab) in isotonic buffer was mixed with an equal volume of different dilutions of immune or preimmune IgY in isotonic buffer, and incubated for 15 minutes at room temperature. Then, 50 μl of a 1% RRBC suspension in isotonic buffer was added and the mixture was incubated for 3 hours at 4° C. Positive control wells containing the final concentration of 9 μg/ml of toxin A after dilution without IgY were also included. Hemagglutination activity was assessed visually, with a diffuse matrix of RRBC's coating the bottom of the well representing a positive hemagglutination reaction and a tight button of RRBC's at the bottom of the well representing a negative reaction. The anti-recombinant immune IgY neutralized toxin A hemagglutination activity, giving a neutralization titer of 1:8. However, preimmune IgY was unable to neutralize the hemagglutination ability of toxin A.

Figure 14:
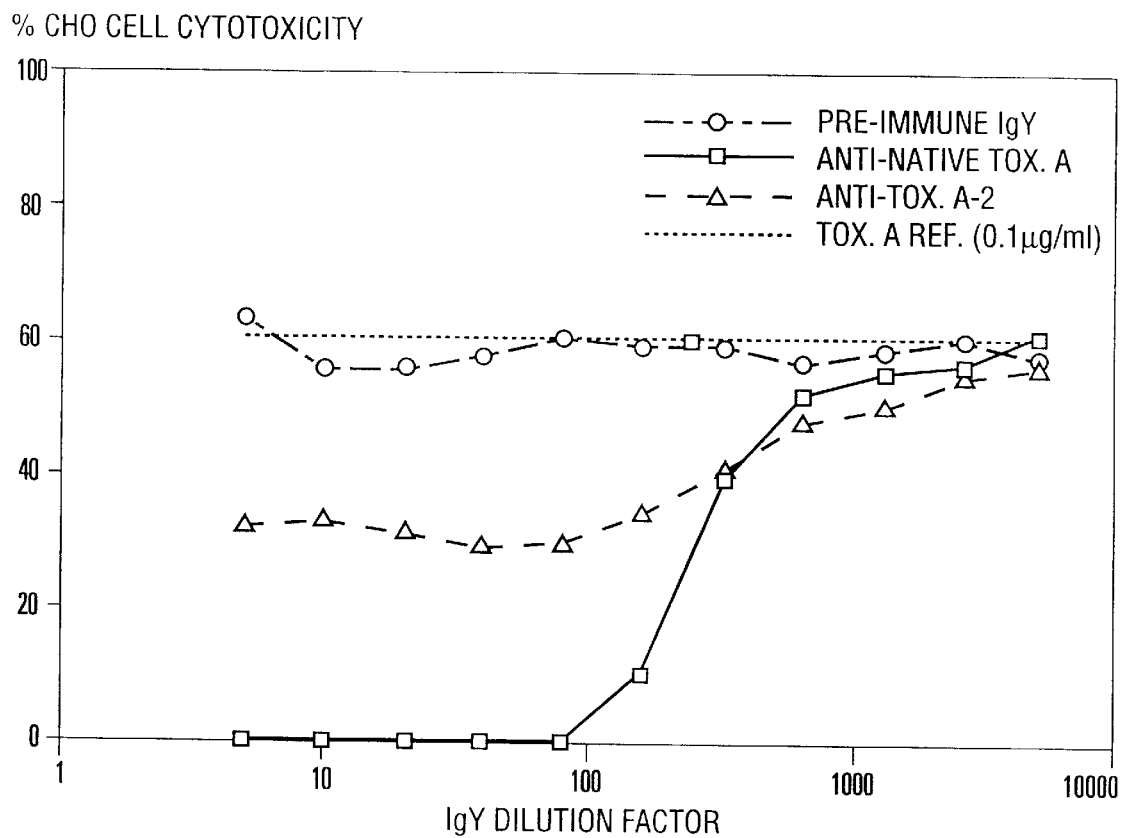
FIG. 14 shows the results of recombinant C. difficile toxin A neutralization assays.

(e) Assay Of in vitro Toxin A Neutralizing Activity. The ability of the anti-recombinant toxin A IgY (immune IgY antibodies raised against pMA1870-2680, the soluble recombinant binding domain protein expressed in pMAL, designated as Anti-tox. A-s in FIG. 14, and referred to as recombinant region 6) and pre-immune IgY, prepared as described in Example 8(c) above, to neutralize the cytotoxic activity of toxin A was assessed in vitro using the CHO cell cytotoxicity assay, and toxin A (Tech Lab) at a concentration of 0.1 μg/ml, as described in Example 8(d) above. As additional controls, the anti-native toxin A IgY (CTA) and pre-immune IgY preparations described in Example 8(c) above were also tested. The results are shown in FIG. 14.

The anti-recombinant toxin A IgY demonstrated only partial neutralization of the cytotoxic activity of toxin A, while the pre-immune IgY did not demonstrate any significant neutralizing activity.

EXAMPLE 14

In vivo Neutralization Of *C. difficile* Toxin A

The ability of avian antibodies (IgY) raised against recombinant toxin A binding domain to neutralize the enterotoxic activity of *C. difficile* toxin A was evaluated in vivo using Golden Syrian hamsters. The Example involved: (a) preparation of the avian anti-recombinant toxin A IgY for oral administration; (b) in vivo protection of hamsters from *C. difficile* toxin A enterotoxicity by treatment of toxin A with avian anti-recombinant toxin A IgY; and (c) histologic evaluation of hamster ceca.

(a) Preparation of the Avian Anti-recombinant Toxin A IgY for Oral Administration. Eggs were collected from hens which had been immunized with the recombinant *C. difficile* toxin A fragment pMA1870-2680 (described in Example 13, above). A second group of eggs purchased at a local supermarket was used as a preimmune (negative) control. Egg yolk immunoglobulin (IgY) was extracted by PEG from the two groups of eggs as described in Example 8(c), and the final IgY pellets were solubilized in one-fourth the original yolk volume using 0.1M carbonate buffer (mixture of $NaHCO_3$ and $Na_2CO_3$), pH 9.5. The basic carbonate buffer was used in order to protect the toxin A from the acidic pH of the stomach environment.

(b) In vivo Protection Of Hamsters Against *C. difficile* Toxin A Enterotoxicity By Treatment of Toxin A with Avian Anti-recombinant Toxin A IgY. In order to assess the ability of the avian anti-recombinant toxin A IgY, prepared in section (a) above to neutralize the in vivo enterotoxic activity of toxin A, an in vivo toxin neutralization model was developed using Golden Syrian hamsters. This model was based on published values for the minimum amount of toxin A required to elicit diarrhea (0.08 mg toxin A/Kg body wt.) and death (0.16 mg toxin A/Kg body wt.) in hamsters when administered orally (Lyerly et al. Infect. Immun., 47:349–352 (1985).

For the study, four separate experimental groups were used, with each group consisting of 7 female Golden Syrian hamsters (Charles River), approx. three and one-half weeks old, weighing approx. 50 gms each. The animals were housed as groups of 3 and 4, and were offered food and water ad libitum through the entire length of the study.

For each animal, a mixture containing either 10 μg of toxin A (0.2 mg/Kg) or 30 μg of toxin A (0.6 mg/Kg) (*C. difficile* toxin A was obtained from Tech Lab) and 1 ml of either the anti-recombinant toxin A IgY or pre-immune IgY (from section (a) above) was prepared. These mixtures were incubated at 37° C. for 60 min. and were then administered to the animals by the oral route. The animals were then observed for the onset of diarrhea and death for a period of 24 hrs. following the administration of the toxin A+IgY mixtures, at the end of which time, the following results were tabulated and shown in Table 17:

TABLE 17

Study Outcome At 24 Hours

| Experimental Group | Study Outcome at 24 Hours | | |
|---|---|---|---|
| | Healthy[1] | Diarrhea[2] | Dead[3] |
| 10 μg Toxin A + Antitoxin Against Interval 6 | 7 | 0 | 0 |
| 30 μg Toxin A + Antitoxin Against Interval 6 | 7 | 0 | 0 |
| 10 μg Toxin A + Pre-Immune Serum | 0 | 5 | 2 |
| 30 μg Toxin A + Pre-Immune | 0 | 5 | 2 |

[1]Animals remained healthy through the entire 24 hour study period.
[2]Animals developed diarrhea, but did not die.
[3]Animals developed diarrhea, and subsequently died.

Pretreatment of toxin A at both doses tested, using the anti-recombinant toxin A IgY, prevented all overt symptoms of disease in hamsters. Therefore, pretreatment of *C. difficile* toxin A, using the anti-recombinant toxin A IgY, neutralized the in vivo enterotoxic activity of the toxin A. In contrast, all animals from the two groups which received toxin A which had been pretreated using pre-immune IgY developed disease symptoms which ranged from diarrhea to death. The diarrhea which developed in the 5 animals which did not die in each of the two pre-immune groups, spontaneously resolved by the end of the 24 hr. study period.

(c) Histologic Evaluation Of Hamster Ceca. In order to further assess the ability of anti-recombinant toxin A IgY to protect hamsters from the enterotoxic activity of toxin A, histologic evaluations were performed on the ceca of hamsters from the study described in section (b) above.

Three groups of animals were sacrificed in order to prepare histological specimens. The first group consisted of a single representative animal taken from each of the 4 groups of surviving hamsters at the conclusion of the study described in section (b) above. These animals represented the 24 hr. timepoint of the study.

The second group consisted of two animals which were not part of the study described above, but were separately treated with the same toxin A+pre-immune IgY mixtures as described for the animals in section (b) above. Both of these hamsters developed diarrhea, and were sacrificed 8 hrs. after the time of administration of the toxin A+pre-immune IgY mixtures. At the time of sacrifice, both animals were presenting symptoms of diarrhea. These animals represented the acute phase of the study.

The final group consisted of a single untreated hamster from the same shipment of animals as those used for the two previous groups. This animal served as the normal control.

Samples of cecal tissue were removed from the 7 animals described above, and were fixed overnight at 4° C. using 10% buffered formalin. The fixed tissues were paraffin-embedded, sectioned, and mounted on glass microscope slides. The tissue sections were then stained using hematoxylin and eosin (H and E stain), and were examined by light microscopy.

The tissues obtained from the two 24 hr. animals which received mixtures containing either 10 $\mu$g or 30 $\mu$g of toxin A and anti-recombinant toxin A IgY were indistinguishable from the normal control, both in terms of gross pathology, as well as at the microscopic level. These observations provide further evidence for the ability of anti-recombinant toxin A IgY to effectively neutralize the in vivo enterotoxic activity of *C. difficile* toxin A, and thus its ability to prevent acute or lasting toxin A-induced pathology.

In contrast, the tissues from the two 24 hr. animals which received the toxin A+pre-immune IgY mixtures demonstrated significant pathology. In both of these groups, the mucosal layer was observed to be less organized than in the normal control tissue. The cytoplasm of the epithelial cells had a vacuolated appearance, and gaps were present between the epithelium and the underlying cell layers. The lamina propria was largely absent. Intestinal villi and crypts were significantly diminished, and appeared to have been overgrown by a planar layer of epithelial cells and fibroblasts. Therefore, although these animals overtly appeared to recover from the acute symptoms of toxin A intoxication, lasting pathologic alterations to the cecal mucosa had occurred.

The tissues obtained from the two acute animals which received mixtures of toxin A and pre-immune IgY demonstrated the most significant pathology. At the gross pathological level, both animals were observed to have severely distended ceca which were filled with watery, diarrhea-like material. At the microscopic level, the animal that was given the mixture containing 10 $\mu$g of toxin A and pre-immune IgY was found to have a mucosal layer which had a ragged, damaged appearance, and a disorganized, compacted quality. The crypts were largely absent, and numerous breaks in the epithelium had occurred. There was also an influx of erythrocytes into spaces between the epithelial layer and the underlying tissue. The animal which had received the mixture containing 30 μg of toxin A and pre-immune IgY demonstrated the most severe pathology. The cecal tissue of this animal had an appearance very similar to that observed in animals which had died from *C. difficile* disease. Widespread destruction of the mucosa was noted, and the epithelial layer had sloughed. Hemmorhagic areas containing large numbers of erythrocytes were very prevalent. All semblance of normal tissue architecture was absent from this specimen. In terms of the presentation of pathologic events, this in vivo hamster model of toxin A-intoxication correlates very closely with the pathologic consequences of *C. difficile* disease in hamsters. The results presented in this Example demonstrate that while anti-recombinant toxin A IgY is capable of only partially neutralizing the cytotoxic activity of *C. difficile* toxin A, the same antibody effectively neutralizes 100% of the in vivo enterotoxic activity of the toxin. While it is not intended that this invention be limited to this mechanism, this may be due to the cytotoxicity and enterotoxicity of *C. difficile* Toxin A as two separate and distinct biological functions.

From the above it is clear that the present invention provides compositions and methods for effective therapy against clostridial toxin disease therapy. It is also contemplated that these antitoxins be used for diagnostic purposes.

We claim:

1. A method of producing clostridial toxin comprising:
   a) providing a host cell overproducing a portion of *Clostridium difficile* toxin A encoded by the restriction fragments produced by restriction of *Clostridium difficile* genomic DNA comprising the *Clostridium difficile* toxin A gene with restriction enzymes SpeI and PstI; and
   b) purifying said portion of said toxin.

2. The method of claim 1 wherein said host cell is *Escherichia coli*.

3. The method of claim 1, wherein said host cell is capable of expressing said portion of *Clostridium difficile* toxin A at a level greater than one milligram per liter of host cell culture.

4. The method of claim 1, wherein said portion of said *Clostridium difficile* toxin A encoded by said restriction fragment is joined to the maltose binding protein.

5. The method of claim 1, wherein said portion of said *Clostridium difficile* toxin A encoded by said restriction fragment is joined to a polyhistidine tag.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GGAAATTTAG CTGCAGCATC TGAC        24

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TCTAGCAAAT TCGCTTGTGT TGAA        24

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CTCGCATATA GCATTAGACC        20

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

(x i) SEQUENCE DESCRIPTION: SEQ ID NO:4:

CTATCTAGGC CTAAAGTAT 19

(2) INFORMATION FOR SEQ ID NO:5:

(i) SEQUENCE CHARACTERISTICS:
    (A) LENGTH: 12 amino acids
    (B) TYPE: amino acid
    (C) STRANDEDNESS: single
    (D) TOPOLOGY: unknown (ii) MOLECULE TYPE: peptide (x i) SEQUENCE DESCRIPTION: SEQ ID NO:5:

Cys Gln Thr Ile Asp Gly Lys Lys Tyr Tyr Phe Asn
  1               5                   10